(12) United States Patent
Krull et al.

(10) Patent No.: US 6,503,711 B1
(45) Date of Patent: Jan. 7, 2003

(54) NUCLEIC ACID BIOSENSOR DIAGNOSTICS

(76) Inventors: Ulrich J. Krull, 1920 Sandown Rd., Mississauga Ontario (CA), L5M 2Z8; Paul A. Piunno, 963 Lovingston Crescent, Mississauga Ontario (CA), L4W 3V7; Robert H. E. Hudson, 389 Dundas St., Apartment 507, London Ontario (CA), N6B 3L5; Masad Damha, 3166 Pierre - Thomas Hurteau, St. Hubert Quebec (CA), J3Y 8N9; Andre H. Uddin, 3665 Adams Way, Suite 1608, Mississauga Ontario (CA), L5A 4A3

( * ) Notice: Subject to any disclaimer, the term of this patent is extended or adjusted under 35 U.S.C. 154(b) by 0 days.

(21) Appl. No.: 09/446,222

(22) PCT Filed: Apr. 30, 1998

(86) PCT No.: PCT/CA98/00402

§ 371 (c)(1),
(2), (4) Date: Feb. 16, 2000

(87) PCT Pub. No.: WO98/58079

PCT Pub. Date: Dec. 23, 1998

Related U.S. Application Data

(60) Provisional application No. 60/050,970, filed on Jun. 19, 1997.

(30) Foreign Application Priority Data

Jun. 18, 1997 (CA) .............................................. 2208165

(51) Int. Cl.[7] .......................... C12Q 1/68; C07H 21/02; G01N 21/29
(52) U.S. Cl. .......................... 435/6; 435/91.1; 435/91.2; 422/68.1; 422/82.05; 422/82.06; 422/82.08; 422/82.09; 250/458.1; 65/409; 536/23.1
(58) Field of Search .......................... 435/6, 91.1, 91.2; 422/68.1, 82.05, 82.07, 82.08, 82.09; 250/458.1; 65/409; 536/23.1

(56) References Cited

U.S. PATENT DOCUMENTS

| | | | |
|---|---|---|---|
| 4,582,809 A | | 4/1986 | Block et al. |
| 4,671,938 A | | 6/1987 | Cook |
| 5,001,051 A | | 3/1991 | Miller et al. |
| 5,135,717 A | | 8/1992 | Renzoni et al. |
| 5,156,810 A | | 10/1992 | Ribi |
| 5,175,209 A | * | 12/1992 | Beattie et al. ............ 525/54.11 |
| 5,242,797 A | | 9/1993 | Hirschfeld |
| 5,485,277 A | | 1/1996 | Foster |
| 5,494,798 A | * | 2/1996 | Gerdt et al. .................... 435/6 |
| 5,684,143 A | * | 11/1997 | Gryaznov et al. .......... 536/23.1 |
| 5,690,894 A | * | 11/1997 | Pinkel et al. ............... 422/68.1 |
| 5,822,073 A | * | 10/1998 | Yee et al. .................... 356/445 |
| 5,830,645 A | | 11/1998 | Pinkel et al. .................. 435/6 |
| 5,837,196 A | | 11/1998 | Pinkel et al. ................. 422/55 |
| 6,060,237 A | * | 5/2000 | Nygren et al. ................. 435/6 |
| 6,146,593 A | | 11/2000 | Pinkel et al. ............... 422/68.1 |

FOREIGN PATENT DOCUMENTS

| | | |
|---|---|---|
| EP | 0 070687 | 1/1983 |
| EP | 0 245 206 | 11/1987 |
| EP | 0 478 319 | 9/1991 |
| EP | 0 519 623 | 6/1992 |
| WO | 91/05261 | 4/1991 |
| WO | 93/06241 | 4/1993 |
| WO | 93/10266 | 5/1993 |
| WO | 93/20240 | 10/1993 |
| WO | 95/26416 | 10/1995 |
| WO | 96/26432 | 8/1996 |
| WO | 00/04390 | 1/2000 |

OTHER PUBLICATIONS

Bauer, G.J. et al. "Traveling waves of in vitro evolving RNA"(1989) *Proc. Natl. Acad. Sci.* USA vol. 86, pp. 7937–7941.

Charreyre, M–T et al. (1997) "Fluorescence energy transfer study of the conformation of oligonucleotides covalently bound to polystyrene latex particles" (1997) *Langmuir* vol. 13, pp. 3103–3110.

Downs, M.E.A. "Prospects for nucleic acid biosensors" (1991) *Biochem. Soc. Trans.* vol. 19(1), pp. 39–43.

Downs, M.E.A. "New DNA technology and the DNA biosensor" (1987) *Analytical Letts.* vol. 20(12), pp. 1897–1927.

Fotin, A.V. et al. "Parallel thermodynamic analysis of duplexes on oligodeoxyribonucleotide microchips" (1998) *Nucleic Acids Res.* vol. 26(6), pp. 1515–1521.

Graham, C.R. et al. "Gene probe assays on a fibre–optic evanescent wave biosensor" *Biosensors & Bioelectronics* (1992) vol. 7, pp. 487–493.

(List continued on next page.)

Primary Examiner—Jeffrey Fredman
(74) Attorney, Agent, or Firm—Greenlee, Winner and Sullivan, P.C.

(57) ABSTRACT

A biosensor for direct analysis of nucleic acid hybridazation by use of an optical fiber functionalized with nucleic acid molecules and fluorescence transduction is disclosed. Nucleic acid probes are immobilized onto the surface of optical fibers and undergo hybridization with complementary nucleic acids introduced into the local environment of the sensor. Hybridization events are detected by the use of fluorescent compounds which bind into nucleic acid hybrids. The invention finds uses in detection and screening of genetic disorders, viruses, and pathogenic micoorganisms. Biotechnology applications include monitoring of gene cultures and gene expression and the effectiveness (e.g. dose-response) of gene therapy pharmaceuticals. The invention includes biosensor systems in which fluorescent molecules are connected to the immobilized nucleic acid molecules. The preferred method for immobilization of nucleic acids is by in situ solid phase nucleic acid synthesis. Control of the refractive index of the immobilized nucleic acid is achieved by the support derivatization chemistry and the nucleic acid synthesis. The preferred optical fiber derivation yields a DNA coating of higher refractive index than the fiber core onto the fiber surface.

61 Claims, 44 Drawing Sheets

OTHER PUBLICATIONS

Hahnenberger, K.M. "Rapid detection of infectious agents with a biosensor–based nucleic acid hybridization assay," Final Report (Dec. 18, 1992) Contract No. N00014–91–C–0279 NTIS (ADA 259050).

Henke, L. et al. "Covalent immobilization of single–stranded DNA onto optical fibers using various linkers" (1997) Anal. Chim. Acta vol. 344, pp. 201–213.

Herne, T.M. and Tarlov, M.J. "Characterization of DNA probes immobilized on gold surfaces" (1997) J. Am. Chem. Soc. vol. 119, pp. 8916–8920.

Jakeway, S. et al. "Development of a long–chain alkyl tether for immobilization of oligonucleotides for use in an optical DNA biosensor," 44th Int'l Conf. on Analytical Sciences and Spectroscopy, Aug. 1998, Abstract #49, Kingston, Ontario, Canada.

Jenkins, Y. and Barton, J.K. "A sequence–specific molecular light switch: tethering of an oligonucleotide to a dipyridophenazine complex of ruthenium(II)" (1992) J. Am. Chem. Soc. vol. 114, pp. 8736–8738.

Krull, U.J. "Investigations of organized monolayer films for biosensor development" 1994 McBryde Medal Award Lecture (1995) Can. J. Chem. vol. 73, pp. 1239–1250.

Krull, U.J. et al. "A fiber optic DNA sensor for rapid detection of environmental E. coli" in Biosensors for Direct Monitoring of Environmental Pollutants in Field (1998) D.P. Nikolelis et.al (eds.) Kluwer Academic Publishers (The Netherlands), pp. 67–77.

Krull, U.J. et al. "A Fiber–Optic DNA Biosensor for Salmonella," Pittcon 1998, Mar. 1–5, p. 4.

Krull, U.J. et al. "Towards a Fiber–Optic DNA Biosensor for Detection of E. Coli," NATO ARW, Smolenice 1997, pp. 25–26.

Krull, U.J. et al. "Fluoresence Detection of DNA Hybridization on Optical Surfaces for Development of Environmental Biosensors for Pathogens," Pittcon 1998, Mar. 1–5, p. 1243.

Krull, U.J. et al. "Fiber Optic Chemoreception" in Fiber Optic Chemical Sensors and Biosensors vol. II (1992) Chapter 21 (Wolfbeis, ed.), CRC Press, Boston, pp. 315–340.

Krull, U. et al. "Immobilization of DNA on Optical Surfaces for Development of Biosensors for Pathogens," 81st Canadian Soc. for Chemistry Conf. and Exhibition, Whistler, British Columbia, Canada, Jun. 1998, Abstract #673.

Krull, U. et al. "Determination of the Average Density of ssDNA on Optical Fiber Biosensors as Prepared by Automated DNA Synthesis," 80th Canadian Soc. for Chemistry Conf. and Exhibition, Windsor, Ontario, Canada, Jun. 1997, Abstract #514.

Krull, U.J. et al. "Fiber Optic DNA Sensor for Fluorimetric Nucleic Acid Analysis," 41st Intl. Conf. on Analytical Sciences and Spectroscopy, Aug. 14–16, 1995.

Krull, U.J. et al. "Immobilization of Single–Stranded DNA for Control of Selectivity, Sensitivity and Response Speed of Hybridization Sensors," Abstract for Gordon Research Conf. on Bio/Analytical Sensors, Jul. 27–Aug. 1, 1997.

Kung, V. T. et al. "Picogram quantitation of total DNA using DNA–binding proteins in a silicon sensor–bases system" (1990) Analytical Biochem. vol. 187, pp. 220–227.

Leggett, K. "Laser Fibre Optic Multi–Probe Biosensor," Biophotonics International, Feb.–Jan. 1997.

Maskos, U. and Southern, E.M. "Oligonucleotide hybridisations on glass supports: a novel linker for oligonucleotide synthesis and hybridisation properties of oligonucleotides synthesized in situ" (1992) Nucleic Acid Res. vol. 20(7), pp. 1679–1684.

Millan, K.M. and Mikkelsen, S.R. "Sequence–selective biosensor for DNA based on electroactive hybridization indicators" (1993) Anal. Chem. vol. 65, pp. 2317–2323.

Olson, J.D. et al. "Quantitation of DNA hybridization in a silicon sensor–based system: application to PCR" (1991) Molecular and Cellular Probes vol. 5, pp. 351–358.

Piunno, P.A. et al. "A DNA based optical sensor for Salmonella" Abstract 850 76th CSC Conference Sherbrooke, Quebec (Mar. 30, 1993–Jun. 3, 1993).

Piunno, P.A.E. et al. "A fiber optic biosensor for fluorimetric detection of DNA hybridization"(1994) Anal. Chim. Acta vol. 288, pp. 205–214.

Piunno, P.A.E. et al. "Fiber–opticDNA sensor for fluorometric nucleic acid determination" (1995) Anal. Chem. vol. 67, pp. 2635–2643.

Piunno, P.A.E. and Krull, U.J. "Tethered Dye Gene Probes" (May 1997) Report for Defense Research Establishment Suffield National Defense (Ralston, Alberta, Canada) Report on Department of Supply and Service Contract #W7702–5–R533/01–XSG, Government of Canada Publications.

Piunno, P. et al. "Fluorimetric Analysis of Double and Triple Stranded Nucleic Acid Sequences Using a Fibre–Optic Biosensor," 79th Canadian Soc. for Chemistry Conf. and Exhibition, St. John's, Newfoundland, Canada, Jun. 1996, Abstract #107.

Piunno, P. et al. "Fluorimetric Analysis of TAT Triple–Stranded Nucleic Acid Formation Using a Fiber–Optic Biosensor," 14th Annual Graduate Student Symp., SUNY at Buffalo, Buffalo, New York, May 1996.

Piunno, P. et al. "A Fibre–Optic Biosensor for Fluorimetric Nucleic Acid Analysis," 78th Canadian Soc. for Chemistry Conf. and Exhibition, Guelph, Ontario, Canada, Jun. 1995.

Piunno, P. et al. "Fiber–Optic Biosensor for Fluorimetric Nucleic Acid Analysis," 13th Annual Graduate Student Symp., SUNY at Buffalo, Buffalo, New York, USA, May 1995.

Piunno, P. et al. "A DNA Based Optical Biosensor for Salmonella," 76th Canadian Society for Chemistry Conf. and Exhibition, Sherbrooke, Quebec, Canada, Jun. 1993.

Shchepinov, S.C. et al. "Steric factors influencing hybridisation of nucleic acids to oligonucleotide arrays" (1997) Nucleic Acids Res. vol. 25(6), pp. 1155–1161.

Su, H. et al. "Network analysis: acoustic energy transmission detection of polynucleotide hybridization at the sensor––liquid interface" (1993) Analyst vol. 118, pp. 309–312.

Tombler, E. R. and Deutsch, D. G. "Spectrofluorometric assay for hybridization of oligonucleotides using ethidium dimer" (1993) BioTechniques vol. 15(6), pp. 1060–1064.

Uddin, A.H. et al. "A fiber optic biosensor for fluorimetric detection of triple–helical DNA" (1997) Nucleic Acids Res. vol. 25, pp. 4139–4146.

Uddin, A.H. "Synthesis and studies on branched and 2'–5'–linked oligonucleotides" Thesis (Ph.D.) McGill University. Made publicly available via the McGill University Library system on Jun. 17, 1997.

Abel, A.P. et al. (1996), "Fiber–Optic Evanescent Wave Biosensor for the Detection of Oligonucleotides," Anal. Chem. 68:2905–2912.

Kleinjung, F. et al. (Sep. 1997), "Fibre–optic genosensor for specific determination of femtomolar DNA oligomers," Anal. Chim. Acta 35:51–58.

Love, W.F. et al. (1991), "Optical Characteristics of Fiberoptic Evansecent Wave Sensors. Theory and Experiment," *Biosensors with Fiberoptics*, Wise and Wingard, (eds.) The Humana Press, Inc., pp. 139–179.

Maskos, U. and Southern, E.M. (1992), "Oligonucleotide hybridizations on glass supports: a novel linker for oligonucleotide synthesis and hybridization properties of oligonucleotide synthesized in situ," Nucl. Acids Res. 20(7):1679–1684.

Maskos, U. and Southern, E.M. (1993), "A study of oligonucleotide reassociation using large arrays of oligonucleotides synthesized on a glass support," Nucl. Acds. Res. 21(20): 4663–4669.

O'Donnell, M. et al. (Jul. 1997), "High–Density, Covalent Attachment of DNA to Silicon Wafers for Analysis of MALDI–TOF Mass Spectrometry," Anal. Chem. 69:2438–2443.

Piunno, P.A.E. et al. (1999), "Considerations for the quantitative transduction of hybridization of immobilized DNA," Anal. Chim. Acta 400:73–89.

Piunno, P.A.E. et al. (2000), "A Critical Review of Nucleic Acid Biosensor and Biochip Technologies," in *Recent Advances in Environmental Chemical Sensors and Biosensors*, O. Sadik and A. Mulchandani,, eds., ACS Symposium Series 762:257–291.

Shchepinov, M.S. et al. (Mar. 1997), "Steric factors influencing hybridization of nucleic acids to oligonucleotide arrays," Nucl. Acids Res. 23:1155–1161.

Thompson, R.B. and Ligler, F.S. (1991), "Chemistry and Technology of Evanescent Wave Biosensors," in *Biosensors with Fiberoptics*, Wise and Wingard (eds.), The Humana Press, Inc., pp. 111–138.

Beier, M. and Hoheisel, J. D., "Versatile derivatisation of solid support media for covalent bonding on DNA–microchips"(May 1999) Nucleic Acids Research 27(9):1970–1977.

Blonder, R. et al., "Application of Redox Enzymes for Probing the Antigen–Antibody Association at Monolayer Interfaces: Development of Amperometric Immunosensor Electrodes" (1996) Anal. Chem. 68:3151–3157.

Bresaluer, K.J., "Extracting Thermodynamic Data From Equiliprium Melting Curves for Oligonucleotide Order–Disorder Transitions" (1994) *Methods in Molecular Biology* S. Agrawal, Ed. Humana Press N.J. Chapter 14, p347.

Burger, D.R., "Novel Antisense Technology: Therapeutic and Diagnostic Applications" (1993) J. Clinical Immunoassay 16:224–230.

Caruso, F. et al., "Quartz Crystal Microbalance Study of DNA Immobilization and Hybridization for Nucleic Acid Sensor Development" (1997) Anal.Chem.69:2043–2049.

Chalikian, T.V. et al., "A more unified picture for the thermodynamics of nucleic acid duplex melting: A Characterization by calorimetric and volumetric techniques" (Jul. 1999) Proc. Nat'l Acad. Sci. USA 96:7853–7858.

Chee, M. et al., "Accessing Genetic Information with High-Density DNA Arrays" (Oct. 1996) Science 274:610–614.

Englisch, U. et al., "Chemically Modified Oligonucleotides as Probes and Inhibitors" (Jun. 1991) Angew. Chem. Int. Ed. Eng. 30(6):613–722.

Foder, S.P.A. et al., "Light–Directed, Spatially Addressable Parallel Chemical Synthesis" (Feb. 15, 1991) Science 251:767–773.

Goodchild, John., "Conjugates of Oligonucleotides and Modified Oligonucleotides: A Review of Their Synthesis and Properties" (May–Jun. 1990) J. Bioconjugate Chem. 1:165.

Granzow, R. and Reed, R., "Interactions in the Fourth Dimension" (Apr. 1992) Biotechnology 10:390–393.

Konig, B. and Gratzel, M., "A Piezoelectric Immunosensor for hepatitis viruses" (1995) Anal. Chim. Acta 309:19–25.

Lesnik et al., "Oligodeoxynucleotides Containing 2'–O–Modified Adenosine: Synthesis and Effects on Stability of DNA:RNA Duplexes" (1993) Biochemistry 32:7832–7838.

Levicky, R. et al., "Using Self–Assembly to Control the Structure of DNA Monolayers on Gold: A Neutron Reflective Study" (1998) J. Am. Chem. Soc. 120:9787–9792.

Marshall, E., "Emphasis Turns From Mapping To Large–Scale Sequencing" (Jun. 1995) Science 268:1270–1271.

Meier, C. and Engles, J. W., "Peptide Nucleic Acids (PNAs)—Unusual Properties of Nonionic Oligonucleotide Analogues" (1992) Angew. Chem. Int. Ed. Eng. 31(8):1008–1010.

Millan, K.M. et al., "Voltammetric DNA Biosensor for Cystic Fibrosis Based on a Modified Carbon Paste Electrode" (1994) Anal. Chem. 66:2943–2948.

Nielsen et al., "Peptide nucleic acids (PNAs): Potential anti–sense and anti–gene agents" (1993) Anti–Cancer Drug Design 8:53–63.

Saha, A.K. et al., "1,1'–Carbonylbis(3–methylimidazolium) Triflate: An Efficient Reagent for Aminoacylations" (1989) J. Am. Chem. Soc. 111:4856–4859.

Schena, M. et al., "Parallel human genome analysis: Microarray–based expression monitoring of 1000 genes" (1996) Proc. Nat'l. Acad. Sci. USA 93:10614–106191.

Sosnowski, R.G. et al., "Rapid determination of single base mismatch mutations in DNA hybrids by direct electric field control" Proc. Nat'l. Acad. Sci. USA 94:1119–1123.

Su, H. et al., "Interfacial Nucleic Acid Hybridization Studied by Random Primer [32]P Labeling and Liquid–Phase Acoustic Network Analysis" (1994) Anal. Chem. 66:(6)769–777.

Su, H. et al., "Platinum Anticancer Drug Binding to DNA Detected by Thickness–Shear–Mode Acoustic Wave Sensor" (1995) Anal. Chem. 67:1010–1013.

Thompson, M. and Furtado, L.M., "High density oligonucleotide and DNA probe arrays for the analysis of target DNA" (Aug. 1999) Analyst 124:1133–1136.

Uhlmann, E. et al., "Oligonucleotide Analogs Containing Dephospho–Internucleoside Linkages" (1993) Protocols for Oligonucleotides and Analogs, Methods in Molecular Biology 20, ed. Sudhir Agarwal, Humana Press, N.J. USA pp. 335–389.

Wang, S. et al, "Ultratrace Measurements of Nucleic Acids by Baseline–Corrected Adsorptive Stripping Square–Wave Voltammetry" (May 1999) Anal. Chem. 71:1910–13.

* cited by examiner

Step 1.
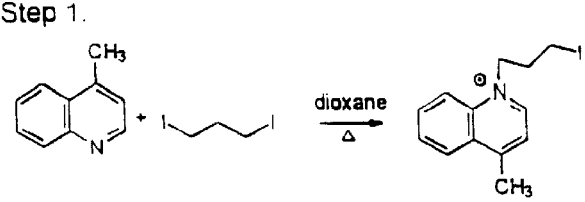
Step 2.
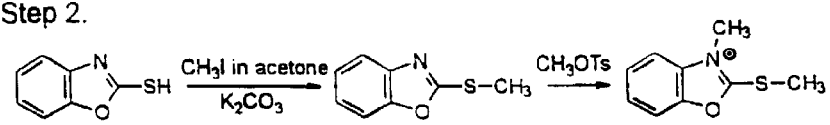
Step 3.
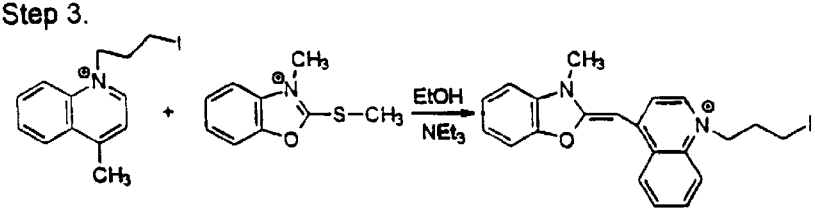
Step 4.
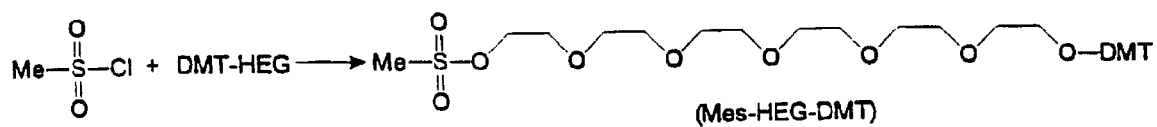
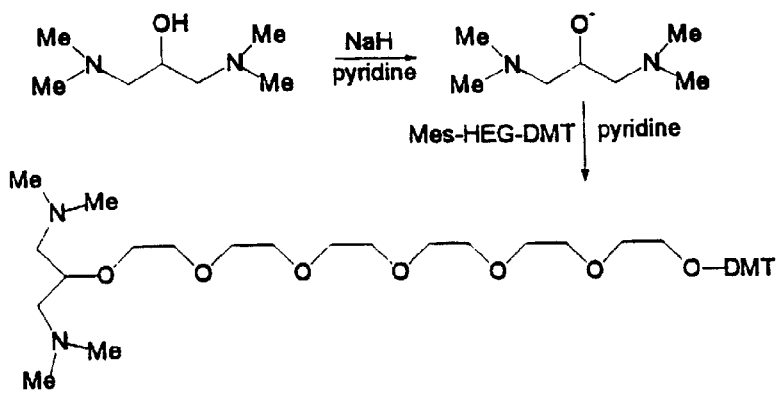
Figure 3(b)   (to be continued)

Step 5:

\* - Injection of cDNA

Prism

Wafer

NUCLEIC ACID BIOSENSOR DIAGNOSTICS

This application claims benefit of Ser. No. 60/050,970 filed Jun. 19, 1997.

FIELD OF THE INVENTION

The present invention is directed generally to biosensors that are useful in the identification and analysis of biologically significant nucleic acids. The biosensors of the present invention and their applied methods provide a means for the direct analysis of nucleic acid hybridization and, therefore, have application to a myriad of biological fields including clinical diagnostics.

BACKGROUND OF THE INVENTION

The detection and identification of microorganisms is a problem common to many areas of human and veterinary health. For example, the detection of pathogenic species such as *Salmonella typhimurium*, *Listeria monocytogenes*, and *Escherichia coli*, which are causative agents of major food borne epidemics, is a great concern within the food industry with respect to the quality and safety of the food supply. In other areas of human and veterinary health care, detection and identification of infectious diseases caused by pathogenic microorganisms and viruses is a first step in diagnosis and treatment. For example, it is estimated that 10–15 million office visits per year are for the detection and treatment of three major pathogens—Chlamydia ssp., *Trichomonas vaginalis* and *Gradenerella vaginitis*. Infections of these organisms annually effect 3.75 million, 0.75 million and 1.5 million patients, respectively.

Classical techniques routinely used for the detection and identification of microorganisms are often labor intensive, involving plating procedures which require lengthy analysis times. To illustrate, the method currently employed for the detection of *Listeria monocytogenes* in food and feed commodities involves a three stage analysis. The analysis begins with enrichment of the sample to be analyzed in a nutrient broth for 2 to 4 days. After the enrichment period, plating of the sample onto selective agar media is done and the sample is allowed to incubate for 2 days in order to obtain colonies for biotyping and serotyping, which may take as long as 20 days to complete (McLauchlin et al., 1988, Microbiology Review, 55: 578).

Detection processes based on culturing require analysis times which are too lengthy for effective monitoring and timely intervention to prevent the spread of biohazardous materials or treat disease. In addition, although these methods have been improved over the last decade, the chance of obtaining false negative results is still considerable, and many microorganisms are difficult to culture. Thus, plating/culture methods are limited with respect to their sensitivity, specificity, and lengthy analysis times that are required.

In order to shorten the time required to detect and identify pathogenic bacteria, viruses and genetic diseases, rapid tests such as enzyme immunoassays (EIA) have been developed (Olapedo et al., 1992). Although immunoassay techniques can be very sensitive and effective, there are practical drawbacks which have restricted the use of these methods. Such drawbacks include the need for highly skilled personnel, lengthy analysis and preparation times, and the large quantities of costly reagents that are required to do such analysis.

With the advent of nucleic acid amplification techniques (the polymerase chain reaction), the in-vitro amplification of specific sequences from a portion of DNA or RNA is now possible. Detection of very low numbers of microorganisms has been demonstrated (Rossen et al., 1991; Golsteyn et al., 1991; Wernars, K., et al., 1991). The polymerase chain reaction technique is sensitive and specific but involves complex manipulations in carrying out the tests and is not particularly well-suited for large numbers of samples. Due to the sensitivity of Polymerase Chain Reaction (PCR) technology, special rooms or areas for sample preparation and analysis are required to prevent contamination. In many tests PCR results must be confirmed by additional hybridization analysis. RNAs are difficult to assay by PCR but are very important for human viral detection. In general, PCR needs to be automated for acceptance as a practical diagnostic tool. Hybridization methods require as much as three or four days to complete results. Although the actual hybridization step can be as short as 18 hours, the entire detection process of a DNA/DNA hybrid can take as long as three days with a radioisotope marker.

Thus, there is a great need for simpler, faster and more cost-effective means for detecting specific biologically important RNA and DNA sequences in the fields of human and veterinary in-vitro diagnostics, food microbiology, and forensic applications.

Biosensors developed to date begin to overcome drawbacks associated with the current state of the art in detecting and identifying microorganisms. A biosensor is a device which consists of a biologically active material connected to a transducer that converts a selective biochemical reaction into a measurable analytical signal (Thompson et al., 1984. Trends in Analytical Chemistry, 3: 173; Guilbault, 1991, Current Opinion in Biotechnology, 2: 3). The advantages offered by biosensors over other forms of analysis include the ease of use (by non-expert personnel), low cost, ease of fabrication, small size, ruggedness, facile interfacing with computers, low detection limits, high sensitivity, high selectivity, rapid response, and reusability of the devices.

Biosensors have been used to selectively detect cells, viruses, other biologically significant materials, biochemical reactions and immunological reactions by using detection strategies that involve immobilization of enzymes, antibodies or other selective proteins onto solid substrates such as quartz and fused silica (for piezoelectric and optical sensors) or metal (for electrochemical sensors) (Andrade et al., 1990, Biosensor Technology: Fundamentals and Applications, R. P. Buck, W. E. Hatfield, M. Umana, E. F. Bowden, Eds., Marcel Dekker Inc., NY, pp. 219; Wise, 1990, Bioinstrumentation: Research, Developments and Applications, Butterworth Publishers, Stoneham, Mass.). However, such sensors are not widely available from commercial sources due to problems associated with the long-term stability of the selective recognition elements when immobilized onto solid surfaces (Kallury et al 1992, Analytical Chemistry, 64: 1062; Krull et al, 1991, Journal of Electron Microscopy Techniques, 18: 212).

An alternative approach is to create biosensors with long-term chemical stability. One such approach takes advantage of the stability of DNA. With the recent advent of DNA probe technology, a number of selective oligomers which interact with the DNA of important biological species, for instance salmonella, have been identified (Symons, 1989, Nucleic Acid Probes, CRC Press, Boca Raton, Fla.; Bock et al., 1992, Nature, 355: 564; Tay et al., 1992, Oral Microbiology and Immunology, : 344; Sherman et al., 1993, Bioorganic & Medicinal Chemistry Letters, 3: 469). These have been used to provide a new type of biorecognition element which is highly selective, stable, and can be easily synthesized in the laboratory (Letsinger et al., 1976, Journal of the American Chemical Society, 98: 3655; Beaucage et al., 1981, Tetrahedron Letters, 22: 1859; Alvarado-Urbina et al., 1981, Science, 214: 270).

Until recently, the only other research group in existence which has published work done on the fluorimetric detection of nucleic acid hybridization immobilized onto optical substrates is that of Squirrell et al. (C. R. Graham, D. Leslie, and D. J. Squirrell, Biosensors and Bioelectronics 7 (1992) 487–493.) In this work, single-stranded nucleic acid sequences ranging in length from 16-mer oligonucleotides to 204-base oligomers functionalized with an aminohexyl linker at the 5' terminus were covalently attached to optical fiber sections functionalized with 3-aminopropyl triethoxysilane via a gluteraldehyde linkage. All investigations of nucleic acid hybridization were done by monitoring fluorescence intensity in an intrinsic mode configuration using complementary strands which had been previously labeled with a fluorescein moiety. This yielded a reusable assay system in which signal generation was observed to occur within minutes and nanomolar detection was achieved. However, this optical sensor technology developed by Squirrell et al. does not contain a transduction element which can transduce the binding event in a reagentless manner. For this assay to function, the target strands must be labeled prior to doing the assay in order for detection, making this technique unsuitable for practical applications.

Abel and co-workers (Abel, A. P.; Weller, M. G.; Duveneck, G. L.; Ehrat, M. and Widmer, H. M. Anal. Chem. 1996 68, 2905–2912) of Norvartis Ltd. (formerly Ciba-Geigy Ltd.) have recently reported an automated optical biosensor system. Their device utilizes 5'-biotinylated-16-mer oligonucleotide probes bound to an optical fiber functionalized with avidin to detect complementary oligonucleotides pre-labeled with fluorescein moieties in a total internal reflection fluorescence (TIRF) evanescent wave motif similar to that of Squirrell. Each assay consisted of a 3 minute pre-equilibration, 15 minute hybridization time, 10 minute washing procedure followed by a 5 minute regeneration cycle (chemical or thermal). A chemical denaturation scheme was observed to be the preferred embodiment for sensor regeneration as exposure of the oligonucleotide functionalized optical sensor to temperatures exceeding 52° C. caused irreversible damage to the device, owing to denaturation of the avidin used for immobilization. This limitation renders the device function labile against sterilization techniques, such as autoclaving, and also indicates that rigorous cleaning of the sensor surface, such as by sonication, would also compromise the integrity of the sensor via denaturation of the affinity pair used to anchor the probe oligonucleotide. In order to detect nucleic acids not pre-labeled with fluorescein, and to overcome the limitation of Squirrell, a competitive binding assay was employed by Abel and co-workers. Detection of the unlabelled analyte was done by pre-treatment of the sensor with fluorescein labeled "tracer-DNA" followed by monitoring decreases in the fluorescence intensity of the sensor upon exposure to and subsequent displacement of the tracer-DNA by complement analyte nucleic acid. The dose-response curves reported by Abel et al. show a detection limit of 132 pmol ($8 \times 10^{13}$ molecules) for this detection strategy. However, in addition to high detection limits and the inability of the device to withstand sterilization, this device cannot be classified as a biosensor technology due to the necessity for external treatment with tracer-DNA in order to achieve transduction.

The prior art with respect to patent literature contains many examples of "sensor" devices which are based on nucleic acid molecules immobilized on waveguide supports and transduction strategies based on evanescent excitation. The technology of Gerdt and Herr (David. W. Gerdt, John. C. Herr "Fiber Optic Evanescent Wave Sensor for Immunoassay", U.S. Pat. No. 5,494,798) describes detection of nucleic acid hybridization based on alterations in the quantity of light transmitted from one optical fiber in a coupled fiber system (similar to that of a Mach-Zehnder interferometer) to the second fiber of the waveguide system. The quantity of light transferred is a function of the refractive index of the media on or surrounding the waveguides. Refractive index alterations affect the penetration depth of the evanescent wave emitted from the first waveguide into which optical radiation is launched. This standing wave of electromagnetic radiation subsequently propagates into (and thus transfers optical radiation to) the second waveguide. Therefore, the device is sensitive to refractive index alterations occurring within a volume surrounding the first waveguide with a thickness of ca. one wavelength of the light propagating within that waveguide. One of the arms of the waveguide may be functionalized with immobilized nucleic acid molecules which serves to provide selective binding moieties. The change in refractive index of the thin film of nucleic acids on the first waveguide upon the occurrence of hybridization with target nucleic acid sequences alters the quantity of light transferred to the second waveguide, thereby providing a means of signal transduction. Hybridization events may then be identified based on changes in the output ratios of the two waveguide arms in the coupled fiber system. One limitation of this technology lies in the fact that any alterations in refractive index near the surface of the waveguides will provide alterations in the output ratios of the two fibers. Therefore, non-specific binding events (such as protein adsorption) will provide false positive results.

In order to avoid the problem of interferents providing false positive results, a transduction strategy which is sensitive to the structure of the binding pair (i.e. recognition element and target) is required. The technologies of Fodor, Squirrell (David James Squirrell "Gene Probe Biosensor Method" International Application Number PCT/GB92/01698, International Publication Number WO 93/06241, International Publication Date: Apr, 1, 1993.), Sutherland et al. (Ranald Macdonald Sutherland, Peter Bromley and Bernanrd Gentile "Analytical Method for Detecting and Measuring Specifically Sequenced Nucleic Acid." European Patent Application Number 87810274.8, Publication Number 0 245 206 A1, Date of Filing: Apr, 30, 1987.), Hirschfeld (Tomas B. Hirschfeld, "Nucleic Acid Assay Method" U.S. Pat. No. 5,242,797, Date of Patent: Sept. 7, 1993.), and Abel et al. (Andreas P. Abel, Michael G. Weller, Gert L. Deveneck, Markus Ehrat, and H. Michael Widmer, *Analytical Chemistry*, 1996, 68, 2905–2912.) overcome this limitation by using fluorescent probes which associate with the binding pair or are attached to selective binding moieties capable of binding to a portion of the binding pair. These inventions provide methods to measure nucleic acid hybridization on waveguide surfaces based on evanescent excitation and TIRF. In each embodiment, an oligonucleotide probe capable of selective binding to a target sequence is covalently immobilized on a waveguide surface. For the cases of Squirrell and Abel et al., each define two preferred embodiments for the detection of hybridization events. The first embodiment of Squirrell and Abel et al. are essentially identical wherein the target nucleic acid is functionalized with a fluorescently detectable agent (by chemical or enzymatic methods) as a first step prior to detection. Upon hybridization between the labeled target and immobilized nucleic acid, the fluorescent agent is then bound in close proximity to the waveguide surface where it may be excited by evanescent wave formation and emission from the fluorophore collected and quantitatively measured. In the second preferred embodiment of Squirrell, hybridization between the immobilized oligonucleotide and the target sequence is first done. Subsequent to the first hybridization event, a fluorescently labeled oligonucleotide present in the system may then undergo hybridization with all or a portion of the remainder of the target sequence not hybridized with the immobilized sequence. The binding of the third (labeled) oligonucleotide provides a fluorescent species bound in close proximity to the waveguide which may furnish transduction via evanescent excitation and collection of the emitted radiation. In the second embodiment of Abel et al, a method for the detection of nucleic acids not pre-labeled with a fluorescent moiety via a competitive binding assay is described. Detection of the unlabelled analyte was done by first pre-treating the optical sensor with immobilized probe nucleic acid with fluorescein labeled "tracer-DNA". The quantity of tracer-DNA may be monitored via the evanescent excitation and collection motif. Binding of the analyte could be followed by monitoring decreases in the fluorescence intensity from the sensor as a function of the displacement of the tracer-DNA via competitive binding with non-fluorescent analyte nucleic acid in a dose-response convention.

In the methods of Sutherland et al. and Hirschfeld, transduction of hybridization events is provided by fluorescent intercalating dyes (e.g. ethidium bromide). Following hybridization between the single-stranded target and immobilized probe nucleic acids, intercalant fluorescent dye molecules from solution insert into the base stacking regions of the immobilized double-stranded nucleic acid. An increase in the fluorescence quantum efficiency, fluorescence lifetime, stokes shift of the fluorescent intercalant probes often occurs upon association with double-stranded nucleic acid. It is claimed by the inventors that these enhanced features may be monitored by evanescent excitation and collection of fluorescence emission.

Fodor et al. have employed light-directed chemical synthesis to generate miniaturized, high density arrays of oligonucleotide probes. DNA oligonucleotide arrays have been fabricated using high-resolution photolithography in combination with solid-phase oligonucleotide synthesis. This form of DNA chip technology may be used for parallel DNA hybridization analysis, directly yielding sequence information from genomic DNA segments. Prior to sequence identification, the nucleic acid targets must be fluorescently labeled, either prior to or after hybridization to the oligonucleotide array, via direct chemical modification of the target strand or by use of an intercalant dye subsequent to hybridization on the DNA chip. The hybridization pattern, as determined by fluorescence microscopy, is then deconvolved by appropriate chemometric processing to reveal the sequence of the target nucleic acid. Rather than focusing on selective detection of trace quantities of a particular nucleic acid sequence, this technology has focused on sequence analysis of nucleic acids in suitably high copy number so as to sufficiently occupy the oligonucleotide array.

Notwithstanding the indubitable accomplishments of the aforementioned prior art, there yet exists limitations in these technologies for which further improvements are most desirous. Although the strategies employed by Sutherland et al. and Hirschfeld overcome the limitations of Gerdt and Herr with regard to signal origin and the generation of false positive results, these assay methods are limited by the amount of signal which can be generated by evanescent excitation. For multimode waveguides, less than 0.01% of the optical radiation carried within the waveguide is exposed to the outer medium in the form of an evanescent wave (R. B. Thompson and F. S. Ligler, "Chemistry and Technology of Evanescent Wave Biosensors" in *Biosensors with Fiberoptics*, Eds.: Wise and Wingard, Humana Press Inc., New Jersey,1991, pp.111–138.). In the case where monomodal waveguides are used, ca.10% of the radiation carried by the waveguide is exposed to the outer medium in the form of an evanescent wave (David. W. Gerdt, John. C. Herr "Fiber Optic Evanescent Wave Sensor for Immunoassay", U.S. Pat. No. 5,494,798). In the classic total internal reflection fluorescence (TIRF) evanescent wave configuration, the critical angle ($\theta_c$) for the waveguide/solution interface ($\theta_c^{W/S}$) is larger than $\theta_c$ for the waveguide/biological film interface ($\theta_c^{W/B}$), only the evanescent component of the propagated radiation will enter the biological film. The principle of optical reciprocity states that light coupled back into a waveguide as a plane wave will be in the same way as the primary process when a plane wave generates an evanescent wave (Ranald Macdonald Sutherland, Peter Bromley and Bernanrd Gentile "Analytical Method for Detecting and Measuring Specifically Sequenced Nucleic Acid" European Patent Application Number 87810274.8, Publication Number 0 245 206 A1, Date of Filing: Apr 30, 1987, p.13.). Thus, for the fluorophores excited by evanescent waves created from modes propagating at or near $\theta_c^{W/S}$, none of the fluorescence emission can be coupled back into the waveguide in the same propagation mode as $\theta_c^{W/S}$ would be >90° (U. J. Krull, R. S. Brown and E. T. Vandenberg, "Fiber Optic Chemoreception" in *Fiber Optic Chemical Sensors and Biosensors*, vol.2, Ed. O. S. Wolfbeis, CRC Press, Boca Raton, 1991, pp.315–340.). Hence a large portion of the signal would be lost to the surroundings for systems in which fluorescence emission originates from thin films of a lower refractive index than that of the waveguide onto which they are immobilized. It has been shown by Love et al. that under optimal conditions, only 2% of the light emitted by the fluorophore in the medium of lower refractive index may be captured and guided by the fiber (W. F. Love, L. J. Button and R. E. Slovacek, "Optical Characteristics of Fiberoptic Evanescent Wave Sensors: Theory and Experiment" in Biosensors with Fiberoptics Eds.: Wise and Vingard, Humana Press Inc., New Jersey, 1991, pp. 139–180.).

SUMMARY OF THE INVENTION

The present invention concerns biosensors for direct detection of nucleic acids and nucleic acid analogs. The device comprises a light source, a detector, and an optical element for receiving light from the source and conveying it to an interaction surface of the optical element. A nucleic acid or nucleic acid analog for a particular nucleic acid sequence or structure (i.e. which is complementary to the target nucleic acid(s)), is immobilized onto the interaction surface of the optical element. Fluorescent ligands are provided that will bind into or onto the hybridized nucleic acid complex and fluoresce when stimulated by the light source. Subsequent to excitation by electromagnetic radiation of suitable wavelength bound within the optical element, the resultant fluorescence is collected within the optical element and guided to the detector to signal that the target nucleic acid(s) has complexed with the immobilized probe and thus indicate the presence of the target in the sample. An interaction surface is defined to mean a surface of the optical element on which nucleic acid is immobilized, and at which the fluorescent molecules interact with the light.

This invention provides biosensors in which the interaction surface is functionalized with nucleic acid probe sequences such that the index of refraction of the immobilized layer (Substrate Linker/Nucleic Acid/Fluorescent Ligand) is equal to or greater than the refractive index at the surface of the waveguide such that the organic coating becomes an extension of the waveguide. The index of refraction of the immobilized layer is dependent, at least in part, on the loading of immobilized molecules and linkers on the surface and the chemical nature of the immobilized molecules and any linkers.

Preferred biosensors which offer high-sensitivity and low-detection limits may be realized by activating the interaction surface of an optical element with substrate linker molecules of at least about 25 Å (Angstrom) in length followed by attachment of a selected probe nucleic acid sequence to that linker. (A probe nucleic acid is, at least in part, complementary to a target nucleic acid.) The preferred method for attachment of the probe nucleic acid to the substrate linker is by in-situ synthesis of the nucleic acid sequence onto the linker terminus using solid-phase nucleic acid synthesis methods or routine modifications of thereof. Such methods of in-situ synthesis are particularly useful for immobilization of nucleic acids of 50 or fewer bases and more particularly useful for nucleic acids of 30 or fewer bases.

The fluorophore may be tethered to the immobilized DNA, for example, by use of a hydrocarbon tether. The use of tethered probes can significantly reduce biosensor response time as the response mechanism is not diffusionally controlled. The associated fluorophore provides for internal calibration of optical source intensity and detector drift. It also provides for calibration of photobleaching, and provides for internal calibration by monitoring bound against free dye by use of, for example, time-resolved fluorescence measurements.

The optical element preferably comprises an optical waveguide which also conveys the fluorescent light to the detector. The optical waveguide preferably conveys the emitted light by total internal reflection to the detector. The optical waveguide can comprise an optical fiber, a channel waveguide, or a substrate that confines light by total internal reflection. The fluorescent molecules preferably provide sufficient Stokes shift such that the wavelength of the light source and the wavelength of the fluorescent light are easily separated. The fluorescent molecules can be provided in a solution in which the optical element is immersed, or by a tether to the nucleic acid that is immobilized to the linker.

In the practice of the present invention, the light source can be any suitable source such as a gas laser, solid state laser, semiconductor laser, a light emitting diode, or white light source. The detector can be any suitable detector such as a photomultiplier tube, an avalanche photodiode, an image intensifier, multi-channel plate, or semiconductor detector. The biosensor system can be a multi-wavelength, multi-fluorescent system. The light coupling of the system can also be modified to allow a multitude of disposable biosensors to be analyzed either sequentially or in parallel.

The biosensor system of the present invention can be constructed and used to detect each of a mixture of target nucleic acids (for example, Chlamydia and Gonorrhea in urogenital infections or *E. coli* and Salmonella during food processing). This may be done by using a plurality of fluorophores (which, for example, fluoresce at different wavelengths), each of which is tethered to an immobilized nucleic acid probe that is characteristic of or specific for detection of a given species or strain. In this example, the observed wavelength(s) of fluorescence emission will then be specific for hybridization of a given target nucleic acid to its complementary immobilized probe.

The biosensors of the present invention have an improved detection limit and sensitivity with respect to the prior art and are shown to be stable over prolonged storage and severe washing and sterilization conditions. Sensors stored over 1 year in vacuo, in 1:1 ethanol/water solutions, absolute ethanol, or dry at −20° C. provide identical response characteristics to those freshly prepared. Adsorbed fluorescent contaminants accumulated through storage can be removed (as confirmed through fluorescence microscopy investigations) by sonicating the biosensors in 1:1 ethanol/water where the sensitivity of the device has consistently been observed to increase by a factor of c.a. 2.5 from this pre-treatment with respect to that of freshly prepared biosensors not cleaned before use. Unlike those of the prior art (e.g. Abel et al.), the optical biosensors of the present invention have also shown to be thermally stable wherein device function is maintained after sterilization by autoclaving (20 minutes, 120° C., 4 atmospheres over-pressure). The ability to clean and sterilize a biosensor device so that it may be usable in an on-line configuration and/or in clinical applications is a significant advantage yet realized only by the technology reported herein. Biosensors of this invention also allow for more rapid sample analysis with improved response time for signal generation.

The present invention also provides a recyclable or disposable biosensor for detecting a target nucleic acid, which biosensor includes an optical element for receiving and conveying light to an interaction surface of the optical element and nucleic acid, for a particular nucleic acid sequence which is complementary to the target nucleic acid, immobilized onto the interaction surface of the optical element. The recyclable or disposable biosensor preferably comprises an optical waveguide, which preferably conveys the light by total internal reflection to the interaction surface of the optical waveguide when the organic coating is of equal or higher refractive index in comparison to the surface of the waveguide. The optical waveguide preferably comprises an optical fiber. Fluorescent molecules are provided in a solution in which the recyclable or disposable biosensor is immersed that will bind upon hybridization of the immobilized nucleic acid with complementary target nucleic acid and fluoresce when stimulated by light. Alternatively, the fluorescent molecules are provided bound by a tether to the immobilized nucleic acid.

The present invention provides biosensors for direct analysis of nucleic acid hybridization by use of an optical substrate such as an optical wafer or an optical fiber, and nucleic acids or nucleic acid analogs which have been immobilized onto the optical substrate. Generation of a fluorescence signal upon hybridization to complementary nucleic acids and nucleic acid analogs in a sample may be achieved in a number of different ways. Biosensors of this invention are sufficiently sensitive to directly detect very small quantities of target nucleic acids in a sample without the need to employ nucleic acid amplification methods such as PCR techniques. Biosensors of this invention can have detection limits for target nucleic acids below $10_8$ molecules.

The optical biosensor comprises nucleic acid strands or nucleic acid analogs of a specific selected sequence immobilized onto activated optical supports. The selected immobilized sequences are capable of binding to target sequences, including sequences characteristic of and selective for viruses, bacteria, or other microorganisms as well as of genetic disorders or other conditions. Biosensors having such characteristic or selective immobilized sequences are useful for the rapid screening of genetic disorders, viruses, pathogenic bacteria and in biotechnology applications such as the monitoring of cell cultures and gene expression. One important avenue which has been widely ignored by the nucleic acid biosensor community is the investigation of multi-stranded ($\geq 3$) nucleic acid formation. For example, triple-helical oligonucleotides have been reported to offer potential use as: sequence-specific artificial nucleases ({a} Moser, H. E.; Dervan, P. B. *Science*, 1987, 238, 645. {b} Strobel, S. A.; Doucettestamm, L. A.; Riba, L.; Housman, D. E.; Dervan, P. B. *Science*, 1991, 254, 1639.), DNA-binding protein modulators/gene expression regulators ({a} Cooney, M.; Czernuszewicz, Postel, E. H.; Flint, S. J.; Hogan, M. E. *Science*, 1988, 241, 456. {b} Durland, R. H.; Kessler, D. J., Gunnel, S., Duvic, M.; Pettit, B. M.; Hogan, M. E.; *Biochem.*, 1991, 30, 9246. {c} Maher, L. J.; Dervan, P. B.; Wold, B.; *Biochemistry*, 1992, 31, 70. {d} Maher, L. J. *BioEssays*, 1992, 14, 807. {e} Maher, L. J. *Biochemistry*, 1992, 31, 7587. {f} Duvalvalentin, G.; Thoung, N. T.; Hélène, C. *Proc. Nat. Acad. Sci. USA*, 1992, 89, 504. {g} Lu, G.; Ferl, R. J. *Int. J. Biochem.*, 1993, 25, 1529.), materials for genomic mapping ({a} Ito, T., Smith, C. L.; Cantor, C. R. *Proc. Natl. Acad. Sci. U.S.A.*, 1992, 89, 495. {b} Ito, T., Smith, C. L.; Cantor, C. R. *Nucleic Acids Res.* 1992, 20, 3524.), and highly selective screening reagents to detect mutations within duplex DNA (Wang, S. H., Friedman, A. E., Kool, E. T. (1995) *Biochemistry* 34, 9774–9784.). The present invention can also be used to detect the formation of multi-stranded nucleic acid hybrids (for example, formation triple-helical nucleic acids), and therefore could, for example, operate to monitor the effectiveness, dose dependence and intracellular concentration of nucleic acid pharmaceuticals used in gene therapy applications or as an assay to identify multi-strand formation associated with any of the aforementioned potential applications associated with triple-helical oligonucleotides.

The invention is a biosensor system for detecting a target nucleic acid, which consists of at least three layers, two of which are a waveguide, wherein one layer includes a nucleic acid or nucleic acid analog capable of hybridizing to the target nucleic acid, and wherein a fluorophore is tethered to the nucleic acid or nucleic acid analog and wherein the biosensor functions according to direct excitation. The invention also relates to a biosensor for detecting a target nucleic acid, which comprises an inner layer, a middle layer and an outer layer, wherein the inner layer has refractive index $n_1$, the middle layer includes a nucleic acid or nucleic acid analog capable of hybridizing to the target nucleic acid and has refractive index $n_2$, which is greater than or equal to refractive index $n_1$, and the outer layer has refractive index $n_3$ which is less than refractive index $n_2$.

and wherein a fluorophore is tethered to the nucleic acid or nucleic acid analog of the middle layer and wherein the biosensor functions according to direct excitation.

In a preferred embodiment, the inner layer is an optical fiber or optical wafer and the outer layer is an ambient. The outer layer is an aqueous based solution. The biosensor is useful for detection of triplex formation or multi-stranded nucleic acid formation. The triplex formation preferably involves a branched antisense nucleic acid which inhibits expression of a target nucleic acid sequence by triplex formation with the sequence.

The biosensor is useful for detection of nucleic acids of bacteria, viruses, fungi, unicellular or multicellular organisms or for the screening of nucleic acids of cells, cellular homogenates, tissues or organs.

Preferably, a fluorophore is tethered to a nucleic acid or nucleic acid analog which is one of the layers of a biosensor having at least three layers and the biosensor functions according to direct excitation. The invention also includes the use of a fluorophore for detecting a target nucleic acid.

The invention also relates to a method of detecting a target nucleic acid, comprising:

pre-treating a sample so that target nucleic acids characteristic of or selective for said sample are available for hybridization;

contacting the sample with the middle layer of the biosensor of claim 2, such that the target nucleic acids can hybridize to the nucleic acids or nucleic acid analogs of the middle layer;

allowing the fluorophore tethered to the nucleic acids of the middle layer to bind upon hybridization of the target nucleic acids with the nucleic acids or nucleic analogs of the second layer;

illuminating the fluorescent molecules with light such that fluorescence is stimulated; and detecting the emitted fluorescence, whereby the presence of the target nucleic acid is detected.

BRIEF DESCRIPTION OF THE DRAWINGS

FIG. 1(*b*). Synthetic scheme of Brennan et al. used to create alkylamine substrate linker molecules on hydroxylated fused silica surfaces.

FIG. 1(*c*). Synthetic scheme of Maskos and Southern used to functionalize hydroxylated fused silica surfaces with GOPS followed by extension with HEG.

FIG. 1(*d*). Possible closed loop structure formation as a consequence of the synthesis scheme used in FIG. 1(*c*).

FIG. 1(*e*). Synthetic scheme used to extend GOPS functionalized substrates with DMT-HEG via a base catalyzed mechanism.

FIG. 1(*f*). Synthetic scheme used to covalently link DMT-HEG onto hydroxylated fused silica surfaces via activation with methanesulfonyl chloride.

FIG. 3(*b*). Synthetic scheme used to create a polyether-tethered phosphoramidite analogue of Ethidium Bromide.

FIG. 3(*b*). Synthetic scheme used to create a polyether-tethered analogue of the bis-intercalative fluorescent probe YOYO-1. Removal of the DMT protecting group followed by treatment with β-cyanoethyl-N,N-diisopropyl phosphityl chloride will yield the tethered YOYO-1 phosphoramidite synthon.

FIG. 4(*b*). Schematic diagram an example of a dedicated instrument for analysis of nucleic acid samples by the fiber-optic nucleic acid biosensor of the present invention.

FIG. 4(*c*). Schematic representation of a biosensor system in which light from a suitable source is directed through a dichroic mirror beam splitter and focused onto a fiber or waveguide coupler and then into an optical fiber having single-stranded nucleic acid bound to the surface thereof, and in which any resultant fluorescent light travels back through the coupler, and passes through the beam splitter and is directed to a photomultiplier detector.

DETAILED DESCRIPTION OF THE INVENTION

Figure 1A:
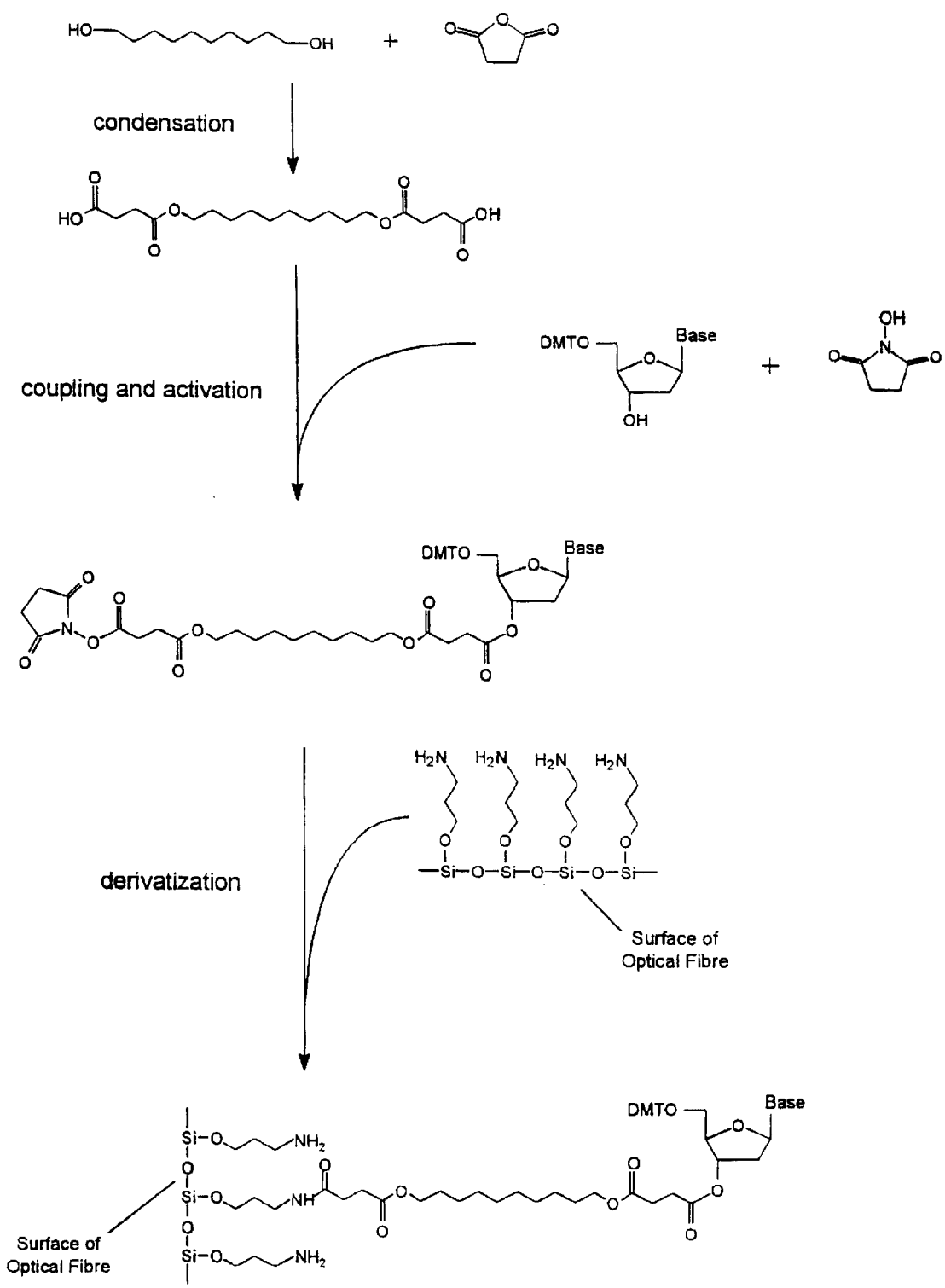
FIG. 1(*a*). Synthetic scheme of Arnold et al. used to activate the glass or fused silica surfaces with long chain aliphatic spacer molecules terminated with 5'-O-dimethoxytrityl-2'-deoxythymidine.

The invention relates to a biosensor which functions according to an intrinsic mode of operation. Using the chemistries as disclosed in this patent application) for attaching linker molecules onto optical waveguide supports (preferably optical fibers) and an automated DNA synthesizer, control over the orientation and a wide range of oligonucleotide packing densities on the waveguide is afforded. In this way, immobilized films of oligonucleotides of desired refractive index may be constructed on waveguide supports so that the oligonucleotide film is made to be an extension of the waveguide. This intrinsic mode of operation provides a highly efficient means of signal generation and collection where fluorescence excitation and emission occur within the waveguide itself, providing an expected enhancement in sensitivity and lowering of detection limits by six orders of magnitude.

The second major improvement provided by our technology is the use of fluorescent dyes tethered to or otherwise associated with the immobilized oligonucleotide. Thompson and Krull ({a} M. Thompson and U. J. Krull, *Trends in Analytical Chemistry*, 3 (1984) 173–178. {b} M. Thompson and U. J. Krull, *Analytical Chemistry*, 63 (1991) 393A–405A.) teach that biosensors may be defined as devices which consists of a biorecognition element and a transduction element. The biorecognition element may be a biological material capable of participating in highly selective binding to a target, usually a biologically significant molecule. The transduction element converts the selective binding reaction into a measurable analytical signal. The transduction strategy of Gerdt is too non-selective for the technology to be classified as a biosensor whereas the devices of Fodor, Squirrell, Abel et al., Sutherland et al. and Hirschfeld do not contain a transduction element at all. In addition to the requirement for external reagent treatment, in the cases of Fodor, Sutherland et al., and Hirschfeld, there also exists the extra shortcoming that all intercalant dyes are known or suspected mutagens. Therefore, the troublesome issues of collection and disposal of hazardous chemical waste exists subsequent to each analysis. By associating the transduction element with the biorecognition element, the device may function without the need for external reagent treatment and obviated the need to collect and dispose of hazardous waste. Such a technology then readily lends itself to automated and in-line analysis and precludes the need for skilled technicians to partake in the analysis procedure or disposal of waste (provided the sample itself is not biohazardous).

The other advantage provided by the incorporated dye is internal calibration. More specifically, three key advantages may be realized: 1) the associated dye provides a means to determine the quantity of fluorophore and immobilized nucleic acid on the waveguide; 2) the fluorophore in the presence of single-stranded nucleic acid provides a baseline signal to which all signals can be referenced, hence providing meaningful analytical data; and 3) the useful lifetime of the device can be determined from alterations in the background fluorescence signal from the incorporated fluorophore over time. Therefore, by including the associated fluorescence transduction unit, an internal reference marker and diagnostic tool for the device status is included as an integral part of the optical biosensor.

Nucleic acid oligomers are covalently immobilized onto optical fibers by first activating the surface of the optical fiber with a long chain spacer arm terminated by a chemically protected terminus, normally a dimethoxytrityl (DMT) moiety, followed by automated solid-phase DNA synthesis. Detection of nucleic acids or nucleic acid analogs at the fiber surface after hybridization between immobilized nucleic acid and its complementary nucleic acid is achieved by measuring enhanced fluorescence emission of the fluorophore.

The optical fiber may be activated with a number of different compounds. The method of Arnold and co-workers (Arnold et al., 1989, *Collect Czech. Chem. Commun.*, 54: 523) may be used for the activation of the fused silica wafers, optical waveguides, and optical fibers whereby 25 atom-long spacer molecules terminated by a dimethoxytrityl protected nucleoside are immobilized onto the cleaned optical fiber substrate, as illustrated in FIG. 1(a). In this method, the length of the spacer between the substrate and the first nucleoside is sufficiently long so that the environment of the terminal nucleoside is fluid enough to permit efficient coupling with successive nucleotide monomers during automated phosphoramidite synthesis of the immobilized nucleic acid probe. This is in accord with the report of Beaucage et al. (1992, Tetrahedron, 48: 2223–2311) wherein it was stated that substrate linkers of lengths of at least 25 atoms are required to achieve high ($\geq 99.5\%$) synthon coupling yields. The synthetic scheme of Arnold et al. requires inexpensive chemicals, is facile to perform, and is done as a one pot procedure wherein product isolation and purification is obviated. Because the linker is terminated by a protected nucleoside, any reactive sites on the support which would lead to the production of unwanted side products during automated synthesis can be eliminated by treating the derivatized supports with acetic anhydride prior to synthesis. Lastly, the coverage of linker on the support is easily determined by determining the amount of trityl cation released during the first trichloroacetic (TCA) deprotection step of the automated synthesis. This methodology does however place limits on the types of nucleobase protecting chemistries can be used as treatment with strong base will cleave the succinate bond between the substrate linker and the oligonucleotide probe.

Figure 1B:
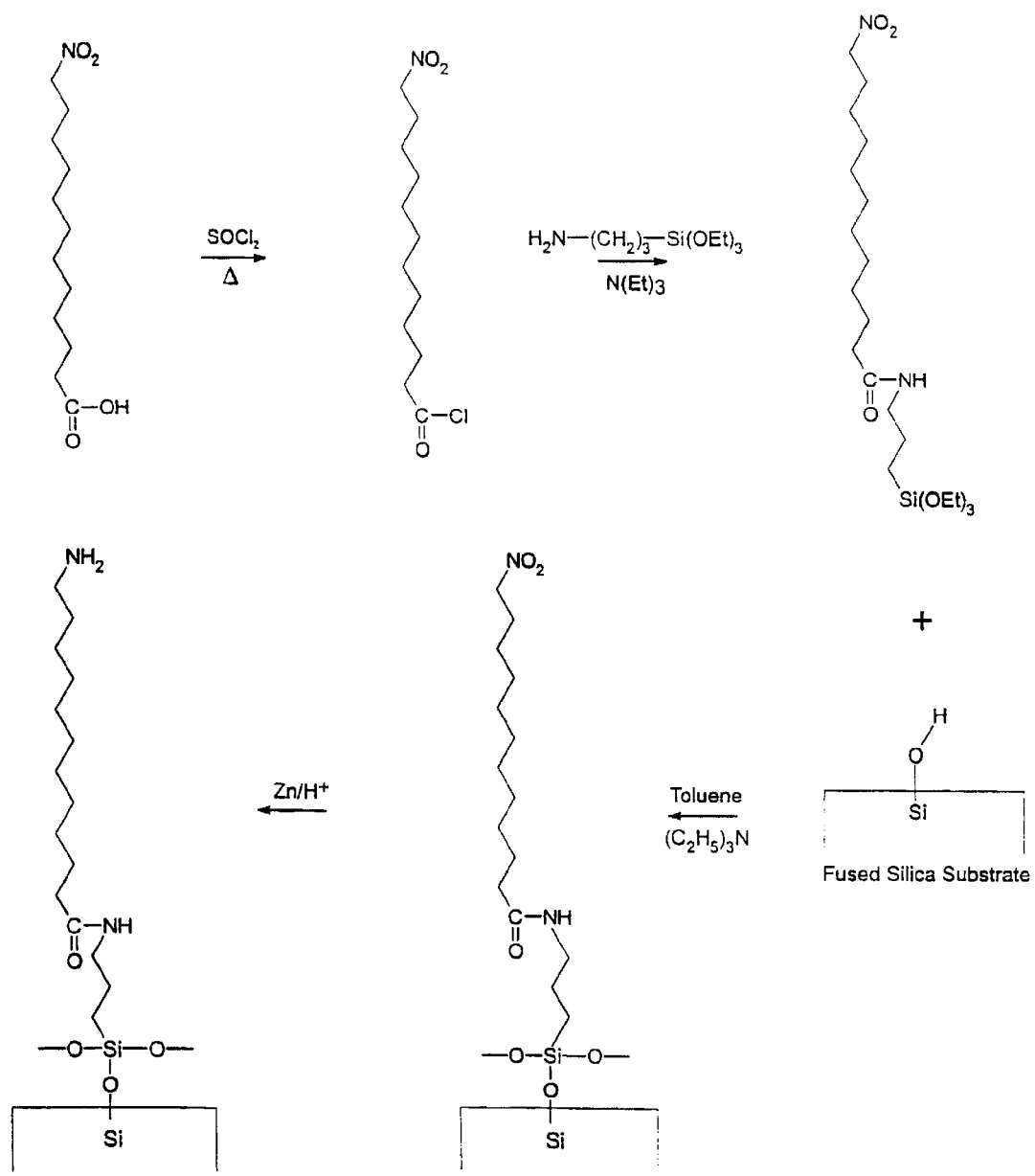

An amine-terminated solid support suitable for automated oligonucleotide synthesis may be prepared according to the method of Brennan et al. (1993, Sensors and Actuators B, 11: 109). A bifunctional amphiphilic support derivatization agent is created by condensing γ-aminopropyltriethoxysilane (APTES) with 12-nitrododecanoic acid. The resulting long chain spacer molecule is covalently immobilized onto the surface of the optical fibers by an $S_N2$ reaction between the hydroxyl groups present at the surface of the fiber and the silane moiety of the amphiphile. With the terminus of the substrate linker in the non-reactive nitro-form, the support may then be capped using standard methods employed during automated synthesis (acetic anhydride), or with chlorotrimethylsilane (R. T. Pon *Methods in Molecular Biology*, Vol.20: Protocols for Oligonucleotides and Analogs, S. Agrawa, Ed, 1993, Humana Press, Inc. Totowa N.J.), thereby masking other sites of reaction which may produce unwanted side products during oligonucleotide synthesis. Reduction of the terminal nitro-functionalities is then achieved by treatment of the derivatized support with an acidic zinc solution. The resulting amine headgroups may then be used directly for automated synthesis wherein an ammonolysis/base resistant phosphoramidate linkage is made between the activated support and the first nucleotide. An outline of a synthetic procedure used to immobilize alkyl amine monolayers covalently onto fused silica substrates is depicted in FIG. 1(b).

Figure 1C:
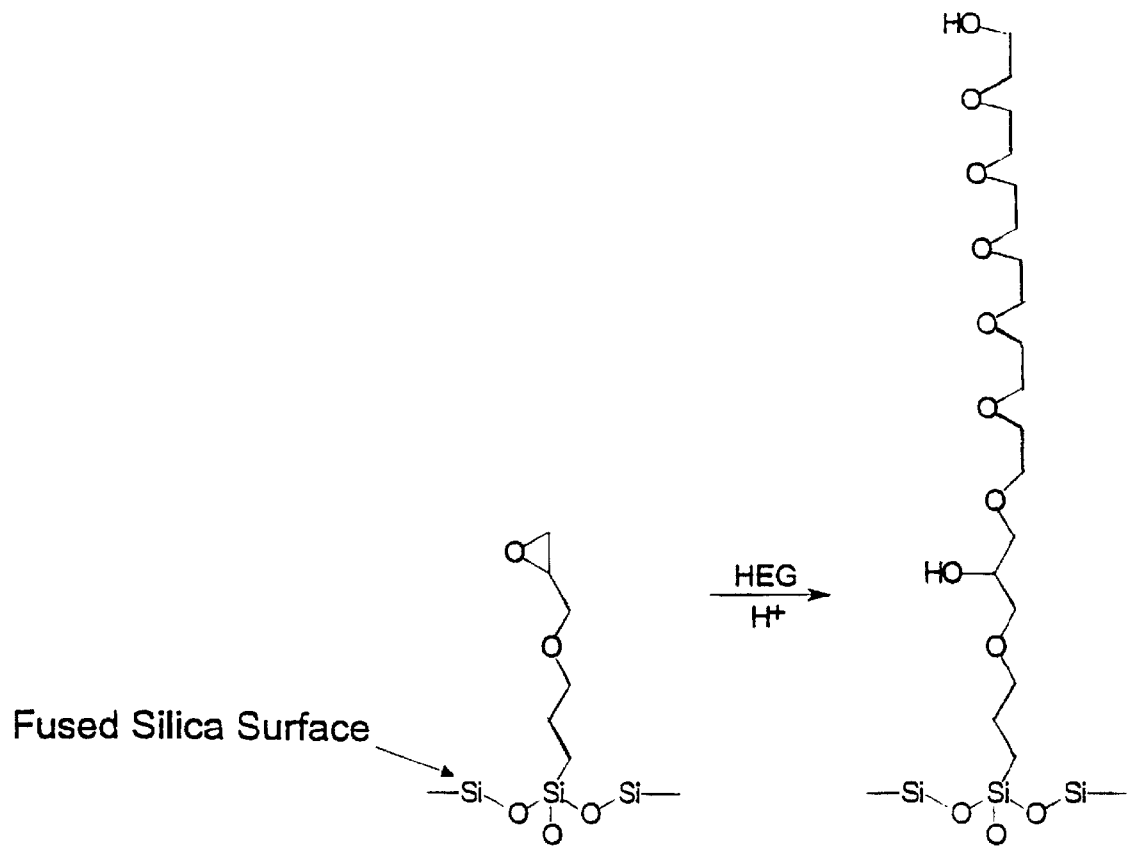

The hydrolysis resistant linkage of Maskos and Southern may also be employed to provide waveguides functionalized with substrate linkers. Analogous to the natural internucleotidic linkage, a phosphodiester linkage between the substrate linker and first nucleotide is completely resistant to ammonolysis under the conditions which remove standard base-protecting groups. This linkage is produced by derivatization of optical fibers with the bifunctional silylating reagent 3-glycidoxypropyltrimethoxy silane via silyl-ether bond formation with the hydroxylated waveguide surface. This yields a substrate derivatized with short spacer molecules with terminal epoxide moieties. The length of the spacer arm is then extended by nucleophilic attack of a polyether, such as hexaethylene glycol (HEG), in an acid catalyzed expoxide ring-opening reaction, yielding a stable ether linkage (U. Maskos and E. M. Southern, 1992 Nucl. Acids Res., 20(7). 1679), as shown in FIG. 1(c). Polyether chains provide for hydration, flexibility for molecular motion, and improved biocompatibility in terms of minimization of non-selective binding to biological compounds. By extending the spacer molecule ensemble to one composed of at least 25 atoms, optimal phosphoramidite synthon coupling efficiencies are realized (Beaucage et al., 1992 Tetrahedron, 1992 48, 2223). This support, terminated with a hydroxyl functionality, is then used directly for automated oligonucleotide synthesis, obviating the need for tedious nucleotide functionalization of the support.

Figure 1D:
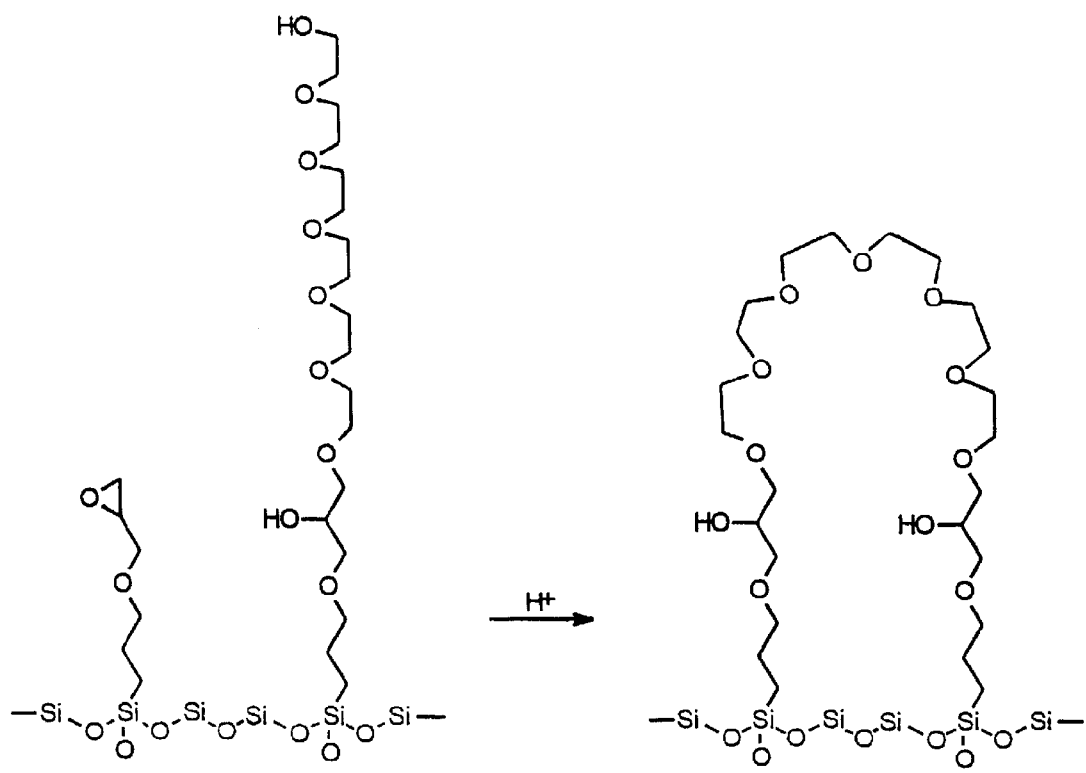
Figure 1E:
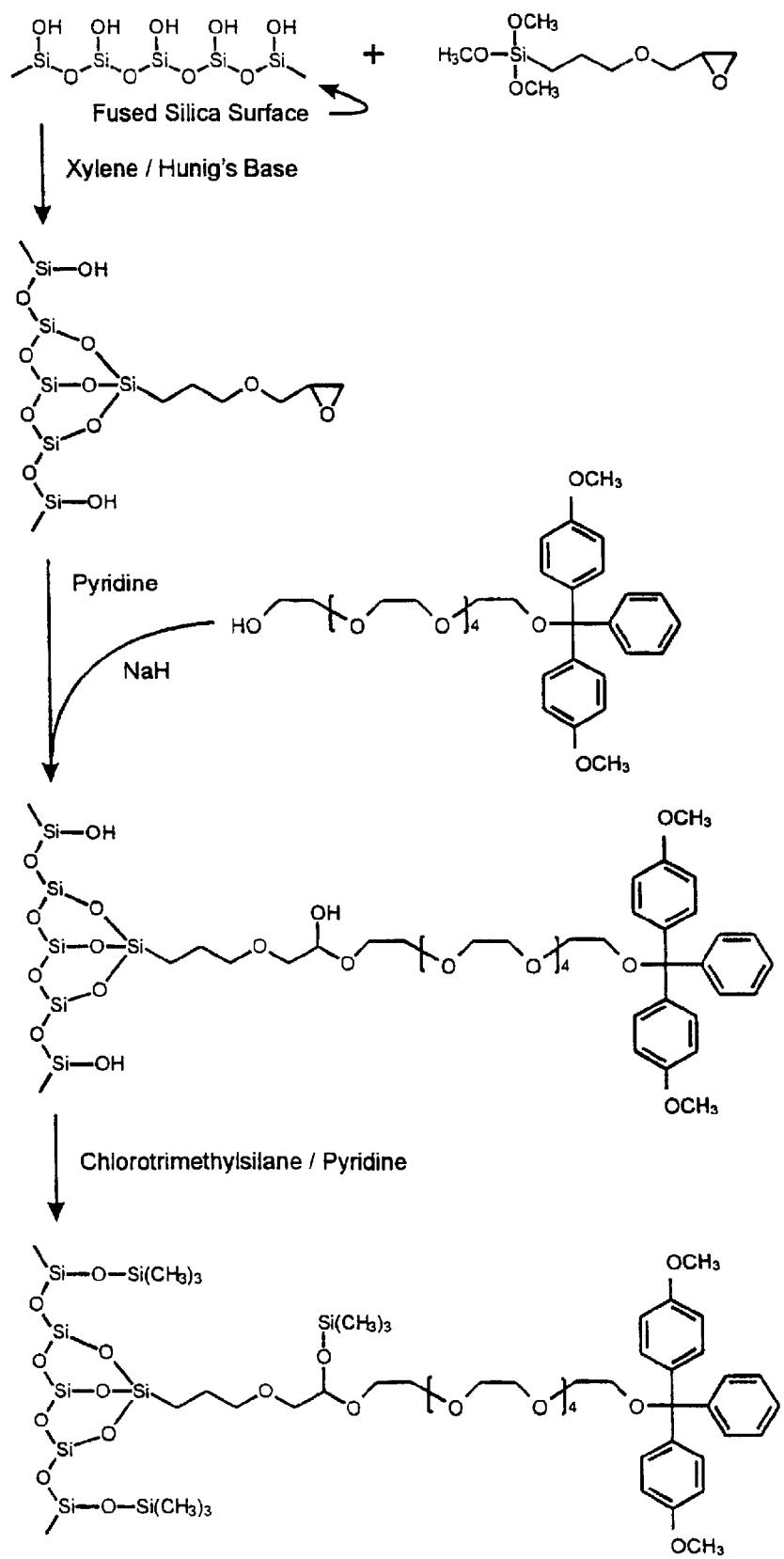
Figure 1F:
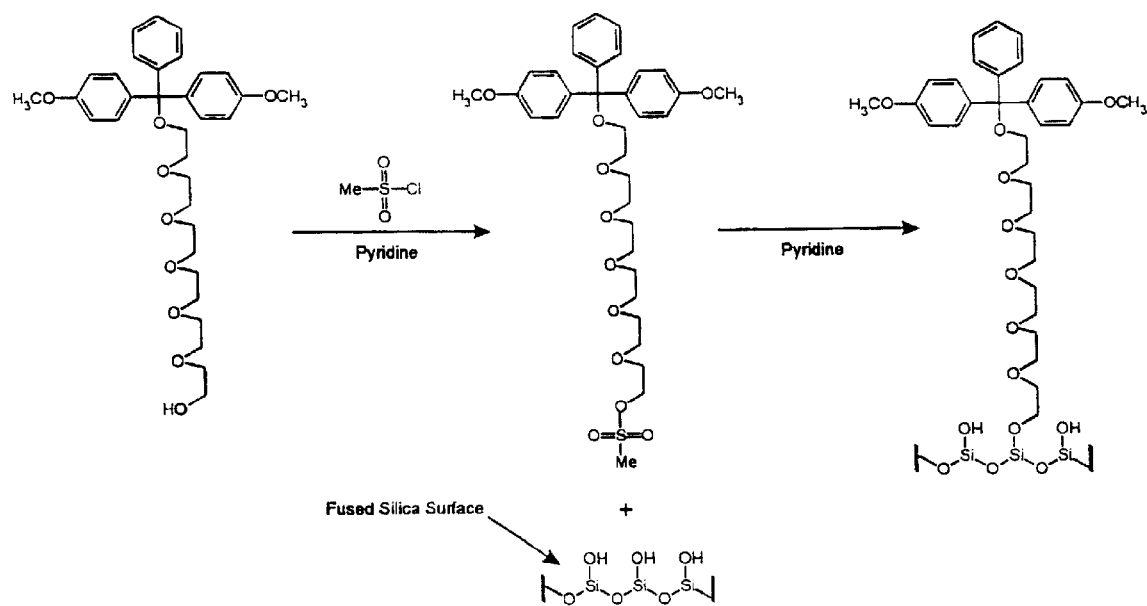
Figure 2:
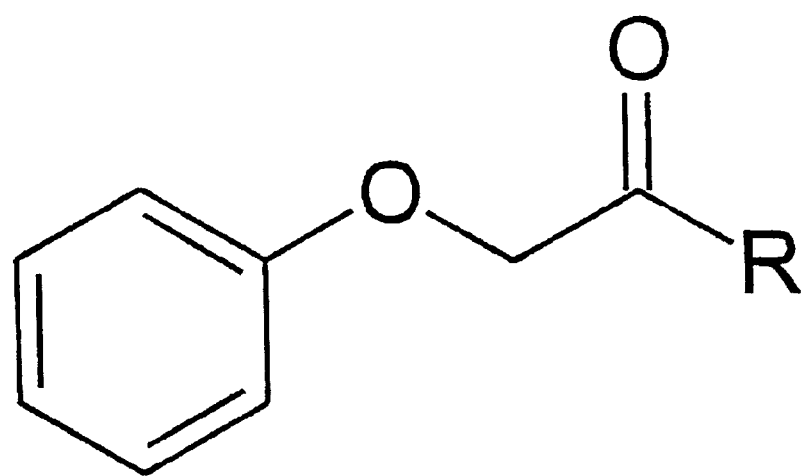
FIG. 2. The phenoxyacetyl protecting group used for exocyclic amine (R) protection on nucleoside phosphoramidite synthons.

Since polyethylene glycols are bifunctional, there exists the possibility of creating non-reactive closed-loop structures which may significantly decrease the amount of loading of oligonucleotides on the surface of an optical fiber, as shown in FIG. 1(d). To eliminate any such problem and improve upon the prior art, one terminus of the polyether is protected with a suitable blocking group, for example, with a DMT functionality, prior to extension of the glycidoxypropyltrimethyl silane. In the case where a chromophoric protecting group is used (such as DMT), an additional advantage is provided wherein facile determination of the amount of support linkers may be determined by monitoring the absorbance of the deprotection solution (e.g. 504 nm for DMT$^+$). Mono-dimethoxytrityl protected polyethylene glycols may be introduced onto the surface of fused silica waveguides by a number of methods. Waveguides first functionalized with GOPS, as in the method of Maskos and Southern, may then be treated with a solution of mono-dimethoxytritylated polyethylene glycol over sodium hydride to afford linkage of the polyether to the terminal epoxide moiety of the immobilized GOPS via a base catalyzed epoxide ring-opening reaction as shown in FIG. 1(e). Mono-dimethoxytritylated polyethylene glycols (such as DMT-HEG) can also be directly linked to the surface of fused silica waveguides by activation of the terminal hydroxyl moiety of the polyether with methane sulfonyl chloride or β-cyanoethyl N,N-diisopropyl phosphityl chloride, as shown in FIGS. 1(e) and 1(f), respectively. In the later case, the polyether substrate linker is attached as a phosphoramidite synthon which can be done as part of the automated oligonucleotide synthesis procedure; thereby making the entire biosensor fabrication protocol completely automated after cleaned waveguide pieces are introduced into the synthesis column of the automated synthesizer.

The biorecognition element to be bound onto the terminus of the substrate linker in configuration of the described biosensor can include immobilized nucleic acids (DNA and RNA), modified nucleic acids, and nucleic acid analogs prepared by well-known methods or by straight-forward extension or modification of those methods. The term nucleic acid includes polynucleotides, oligomers, relatively short polynucleotides (up to about 50 bases), longer polynucleotides ranging up to several hundred bases, and doubled-stranded polynucleotides. There is no specific size limit on nucleic acids used for immobilization in this invention. However, problems due to self-hybridization and reduced selectivity may occur with longer nucleic acids. As used herein, the term "nucleic acid analogs" includes modified nucleic acids. As used herein, the term "nucleotide analog" includes nucleic acids where the internucleotide phosphodiester bond of DNA or RNA is modified to enhance bio-stability of the oligomer and "tune" the selectivity/specificity for target molecules (Ulhmann, et al, 1990, Angew. Chem. Int. Ed. Eng., 90: 543; Goodchild, 1990, J. Bioconjugate Chem., I: 165; Englisch et al, 1991, Angew, Chem. Int. Ed. Eng., 30: 613). Such modifications may include and are not limited to phosphorothioates, phosphorodithioates, phosphotriesters, phosphoramidates or methylphosphonates.

In the present invention, nucleic acid sequences are covalently attached to the surface of the optical fiber. In a preferred embodiment, an automated DNA synthesizer is used to grow nucleotide oligomers onto the surface of activated optical fibers via the well established β-cyanoethylphosphoramidite method. Any commercially available automated DNA synthesizer can be used. The use of an automated synthesizer to grow nucleic acids or nucleic acid analogs on the optical fiber substrates provides many advantages over conventional techniques of DNA immobilization. Conventionally, nucleic acid strands are adsorbed onto a suitable support (usually nitrocellulose) with little known about strand orientation. The use of an automated oligonucleotide synthesizer provides full control of the oligomer sequence, strand orientation, and packing density in association with activation of the optical fiber substrates. Control over these parameters is critical to the development of a nucleic acid detection method based on hybridization as the alignment of the immobilized strands with respect to the availability of target nucleotides for hybridization and intermolecular interactions (electrostatic and steric) between oligomers will have direct ramifications on the kinetics and thermodynamics of hybrid formation and dissociation. The use of a gene machine, in addition to the chemistry used to activate the surface of the optical fibers, allows for the creation of membranes of desired density and structural order to permit rapid and reversible hybridization, and to control refractive index.

The use of the phosphoramidite method of oligonucleotide synthesis has been widely reviewed and has become the synthetic method of choice owing to the high coupling efficiencies and robustness of the reagents, in addition to the fact that the necessity of numerous product isolation and purification steps (which are required for liquid phase methods) are avoided. There are two readily available types of phosphoramidites which may be used to synthetically grow oligonucleotides, namely, methylphosphoramidites and β-cyanoethylphosphoramidites. The method utilizing β-cyanoethyl phosphoramidites is preferable as complete deprotection of the oligonucleotides can be done using aqueous ammonia (as opposed to thiophenol) for the case where oligonucleotides were grown onto controlled pore glass (CPG). Triethylamine is used to deprotect the β-cyanoethyl protected oligonucleotides grown onto fused silica wafers or optical fibers without liberating the oligonucleotides from the support. An overview of the β-cyanoethylphosphoramidite synthesis is as follows:

The first step in each cycle of solid phase automated phosphoramidite synthesis involves the removal of the dimethoxytrityl protecting group on the immobilized nucleotide. Detritylation is done by introducing a solution of 3% trichloroacetic acid (TCA) in 1,2 dichloroethane (DCE) onto the synthesis column in order to yield a 5'-hydroxyl functionality onto which the next nucleotide monomer may be coupled. TCA is the reagent of choice for detritylation due to its rapid reaction rate so that the oligonucleotide is only exposed to the acid for short periods of time, thereby avoiding the acid catalyzed removal of the adenine and guanine moieties from the nucleotide sugar groups by the process of depurination. Once the reaction has been completed, the acid is removed by flushing the column with acetonitrile. The eluent containing the released trityl cation is sent to a fraction collector so that the coupling efficiency of the synthesis may be monitored by absorption spectroscopy.

Coupling is the next stage of the synthesis cycle. The contents of the synthesis column are dried by alternatively washing with acetonitrile and flushing with dry argon. This ensures that the support is anhydrous and free of nucleophiles. The desired phosphoramidite and tetrazole are then sent into the synthesis column. Tetrazole is a weak acid ($pK_a$=4.8) which is used to activate the phosphoramidite. Nucleophilic attack by the 5'-hydroxyl group on the activated phosphoramidite moiety forms an internucleotide linkage. A ten-fold molar excess of phosphoramidite in an excess of tetrazole is added to the synthesis column to ensure that high coupling yields are achieved.

The next step of the synthesis is the capping step. This is done to eliminate further growth of sequences onto which coupling did not occur. The failed sequences are rendered unreactive by introducing acetic anhydride in the presence of dimethylaminopyridine in order to acetylate any remaining unprotected 5'-hydroxyl moieties.

Because the trivalent internucleotide phosphite moieties are labile to both acidic and basic conditions, a solution of aqueous iodine is added after flushing the capping reagents from the column. This is done in order to oxidize the trivalent internucleotide phosphite moieties to the more stable pentavalent phosphate moieties found in naturally occurring nucleic acids. This procedure is termed the oxidation step.

Following the oxidation step, one cycle of nucleotide addition is complete. The process may be repeated many times until oligonucleotides of desired length and base sequence have been constructed. After addition of the last nucleotide, a final detritylation step is usually done in order to yield a 5'-hydroxyl group on the completed sequence.

Triethylamine is used for the removal of β-cyanoethyl protecting groups on the internucleotidic phosphotriester moieties of oligonucleotides grown onto optical substrates. This procedure is known to cause quantitative loss of the phosphate protecting groups via a β-elimination mechanism while not cleaving the single-stranded nucleic acids from the optical fibers. Ammonia treatment of the immobilized oligonucleotides is avoided by choosing an all-thymine base sequence. Thymine does not contain a primary amine functionality which would require protection during oligonucleotide synthesis. This approach is not limited to the use of phosphoramidite synthons, but is compatible with all commercially available solid-phase synthesis such as the H-phosphonate chemistry (Froehler, B. C., 1986, Tetrahedron Letters, 27: 5575; Stein et al, 1990, Analytical Biochemistry, 188: 11).

Contrary to the conventional preparation of oligonucleotides by solid-phase synthesis, post-synthesis removal of the product from the support is not desired. In order to prevent cleavage of the oligonucleotide from the support (optical fiber) while removing the protecting groups of the nucleobases, two modifications to the usual synthetic protocol can be made. The approach involves the combination of a hydrolysis resistant linkage between the oligomer and support along with the use of labile base protecting groups. Thus, an oligomer of any sequence can be prepared and deprotected yet remain attached to the support, available for hybridization.

The phenoxyacetyl (PAC) family of protecting groups represents a convenient method for blocking the exocyclic amino functions of guanine, adenine and cytosine residues (thymine or uracil require no nucleobase protection). The half-time of deprotection with concentrated ammonium hydroxide at 20° C. is 8 min, 7 min and 2 min, respectively (Wu et al, 1989). Under these conditions, the cyanoethyl phosphate protecting groups are removed within seconds (Letsinger and Ogilvie, 1969), whereas the linkage which joins the oligomer to the surface of the fused silica fiber (e.g., a phosphodiester or phosphoramidate) is completely stable under these conditions. Alternative labile protecting groups are derivatized phenoxyacetyl groups including alkyl substituted PAC groups, more specifically t-butylphenoxyacetyl groups. The t-butylphenoxyacetyl group can be quickly removed compared to hydrolysis of the linkage to the spacer thereby reducing the possibility of cleavage of the immobilized sequence from the surface. N-phenoxyacetyl deoxynucleoside 3'-cyanoethylphosphoramidites and the analogous t-butylphenoxyacetyl phosphoramidites are commercially available. It has been reported by Polushin and Cohen (N. N. Polushin and J. S. Cohen, Nucleic Acids Research, 1994, 22, 5492–5496) that the t-butylphenoxyacetyl nucleobase protecting groups can be quantitatively be removed by treatment with ethanolamine for 10 minutes at room temperature or by treatment with a mixture of hydrazinelethanolamine/ MeOH (1:1:5 v/v/v) for 3 minutes. Beaucage and co-workers (J. H. Boal, A. Wilk, N. Harindranath, E. E. Max, T. Kempe and S. L. Beaucage, Nucleic Acids Research, 1996, 24, 3115–3117.) also report the rapid and quantitative removal of t-butylphenoxyacetyl protecting groups by treatment of the support-bound protected nucleic acid with gaseous amines ({a} anhydrous ammonia gas, 10 bar, 25° C., 35 min. or, {b} methylamine, 2.5 bar, 25° C., 2 min.)

Other possible labile protecting groups could include the "FOD" (fast oligonucleotide deprotection available from Applied Biosystems Inc.) based on N,N-dialkylformamidines (Vinayak et al, 1992, Nucleic Acids Research, 20: 1265–1269). Kuijpers et al (Tetrahedron Lett., 1990, 31 6729–6732 and Nucleic Acids Res., 1993, 21, 3493–3500) have described a method of nucleobase protection using 2-(acetoxy-methyl) benzoyl (AMB) moieties which can be removed by treatment with anhydrous potassium carbonate in methanol for 90 minutes at room temperature. Use of protecting groups that can be selectively removed under conditions that will not cleave the oligomer from the support, such as the levulinyl group (removed by hydrazine treatment) (Letsinger et al, 1968, Tetrahedron Letters, 22: 2621–2624; Hassner et al, 1975, J. Amer. Chem. Soc., 97: 1614–1615) are also contemplated by the present invention. Even synthesis without nucleobase protecting groups is possible for nucleic acid oligomers of up to 20 nucleobases in length using the phosphoramidite approach (Gryaznov et al, 1991, J. Amer. Chem. Soc., 113: 5876) or H-phosphonate chemistry (Kung et al, 1992, Tetrahedron Letters, 33: 5869). Any of these approaches circumvents difficulties in removing nucleobase protecting groups while leaving the oligomer attached to the support.

Free short strands of nucleic acids can also be covalently attached to the optical fiber directly or via linker molecules. This approach allows the use of DNA or RNA isolated from natural sources, amplified nucleic acids or their analogs, or synthetic samples provided in the fully deprotected form. Protocols provide end-attached oligomers of a well defined orientation. Chemically stable linkages between the support and oligonucleotide may be employed to enhance the robustness of the biosensor.

Quartz (or interchangeably fused silica) optical fibers derivatized with linker molecules terminated with either hydroxyl or amino groups can serve as substrates for carbodiimide-mediated coupling with terminally phosphorylated single-stranded nucleic acids. Coupling to the hydroxyl fiber produces a phosphodiester bond while coupling to an amine fiber yields a phosphoramidate bond. Oligonucleotides can be phosphorylated, in solution, either chemically via a modification of Ouchi's method (Sowa et al Bull. Chem. Soc., Japan 1975, 48 2084) or enzymatically.

Covalent attachment of free short strands of single-stranded nucleic acid to the optical fibers can be achieved by a slight modification of the method Ghosh and Musso (Ghosh and Musso, 1987, Nucl. Acids Res. 15: 5353). Coupling of a 5'-aminohexyl derivatized oligomer with activated carboxyl fibers affords end-attached oligomers. This method is known to minimize reaction at the amino groups of the DNA bases (which would potentially compromise the hybridization event) and affords surfaces with excellent nucleic acid coverage. The synthesis of the 5'- or 3'-terminally modified oligomers can be achieved readily by standard methods (Ghosh and Musso, 1987; Beaucage and Iyer, 1993).

RNA may be assembled on the support or prepared separately and linked to the support post-synthesis. RNA monomers are commercially available, as are some 2'-O-modified synthons. The 2'-O-methyl, allyl and 2'-deoxy-2'-fluoro RNA analogs, when incorporated into an oligomer show increased biostability and stabilization of the RNA/DNA duplex (Lesnik et al, 1993, Biochemistry, 32: 7832).

As used herein, the term "nucleic acid analogs" also include alpha anomers ($\alpha$-DNA), L-DNA (mirror image DNA), 2'-5' linked RNA, branched DNA/RNA or chimeras of natural DNA or RNA and the above-modified nucleic acids. Back-bone replaced nucleic acid analogs can also be adapted to use in the biosensor of the present invention.

For purposes of the present invention, the peptide nucleic acids (PNAs) (Nielsen et al, 1993, Anti-Cancer Drug Design, 8: 53; Engels et al, 1992, Angew, Chem. Int. Ed. Eng., 31: 1008) and carbamate-bridged morpholino-type oligonucleotide analogs (Burger, D. R., 1993, J. Clinical Immunoassay, 16: 224; Uhlmann, et al, 1993, Methods in Molecular Biology, 20, "Protocols for Oligonucleotides and Analogs," ed. Sudhir Agarwal, Humana Press, NJ, U.S.A., pp. 335–389) are also embraced by the term "nucleic acid analog." Both exhibit sequence-specific binding to DNA with the resulting duplexes being more thermally stable than the natural DNA/DNA duplex. Other back-bone replaced nucleic acids are well-known to those skilled in the art and may also be used in the present invention (See e.g., Uhlmann et al 1993, Methods in Molecular Biology, 20, "Protocols for Oligonucleotides and Analogs," ed. Sudhir Agrawal, Humana Press, NJ, U.S.A., pp. 335).

Optical substrates such as planar wafers and optical fibers may be used in the present invention. A preferred embodiment utilizes optical fibers. Optical fibers are particularly advantageous as membrane supports due to their small size, high light transmission capability, and ability to allow total internal reflection (TIR) of light. Optical fibers also provide a compact an rugged sensing device, and offer the ability to do remote spectroscopic measurements (Love et al, 1991, Biosensors with Fiberoptics, D. L. Wise and L. B. Wingard (Eds.), Humana, NJ, pp. 139–180).

There are two fundamental configurations in which alterations in fluorescence parameters from fluorescently doped membranes on optical fibers may be monitored, namely, extrinsic mode and intrinsic mode. Extrinsic mode configurations are those in which the waveguide is simply used as a light pipe or conduit. End-on extrinsic mode investigations are usually done using optical fibers. In a biosensor which uses end-on extrinsic mode configurations, the fluorescent dyes and selective chemistry are located on or near the distal end of the fiber. The fiber is used as a light-pipe or conduit, where the excitation or emission radiation is simply guided from the sampling region to the detector. Fluorescence is stimulated by coupling excitation radiation into the near end of a fiber, and emission can be monitored by placing light sensing equipment directly opposite the distal end of the fiber.

Alternatively, the detector is placed at the near end of the fiber as some of the fluorescence may be coupled back into the fiber and totally internally reflected back to the near end. The side-on extrinsic mode approach is typically used for investigations carried out on planar supports, but may also be used for fibers. The immobilized single-strand nucleic acid and fluorophore are placed along the length of the optical fiber waveguidelwafer. The fiber is illuminated by a light source located normal to the length of the fiber and fluorescence emission is also monitored by equipment placed normal to the fiber. Extrinsic configurations provide the advantage that simple and inexpensive equipment, including conventional light sources and detectors, are used (Krull et al, 1991, Fiber Optic Chemical Sensors and Biosensors, Vol. II, O. S. Wolfbeis, Ed., CRC Press, Boca Raton, pp. 315). However, the extrinsic sampling configuration provides poorer sensitivity owing to the short path length and sensitivity to interferents present in the surrounding media. In a preferred embodiment, an intrinsic mode arrangement, based on careful control of refractive index is used to monitor fluorescence emission from the surface of optical fibers.

Fluorophores present at either the surface or just below the surface of the fiber may be excited through the formation of a standing wave electric field which propagates normal to the surface of the fiber upon total internal reflection of radiation in the fiber. The process of TIR occurs when the angle of incidence, $\theta$, at the interface between a fiber of high refractive index, $n_1$, and the external medium of lower refractive index, $n_2$, is larger than a critical angle, $\theta_c$, defined as:

$$\mathrm{Sin}\,\theta_c = \frac{n_2}{n_1} \tag{1}$$

The amplitude of the electric field of the reflecting radiation decreases exponentially as a standing wave into the medium having the lower refractive index. This decaying radiation is referred to as an evanescent wave and can be used to excite fluorophores located near the boundary for TIR. The propagation intensity, I, of the evanescent wave depends on the reflection angle, $\theta$, the wavelength of the transmitted radiation, $\gamma$, and a Fresnel transmission factor, T:

$$I = T(\theta) \cdot \exp\left(\frac{-2x}{d_p}\right) \quad (2)$$

where x represents distance normal to the boundary for TIR, and $d_p$ is the penetration depth which is given by (Krull et al, 1990, Talanta, 37: 801–807):

$$d_p = \frac{\lambda}{4\pi\sqrt{n_1^2\sin^2(\theta) - n_2^2}} \quad (3)$$

The penetration depth is defined as the distance at which the intensity of the evanescent field has decayed to 1/e of the intensity at the reflection boundary. Typically, the evanescent wave propagates into a thin zone beyond the surface of a fiber with a penetration depth ranging from about 200 nm to 400 nm for visible light.

Fluorophores within the evanescent wave propagation zone are excited by that evanescent wave to emit fluorescence. Fluorophores further from the interface with the optical fiber will experience lower intensity of light at the excitation frequency and a resultant concomitant decrease in intensity of emitted fluorescence.

A major limitation of the evanescent wave excitation is that less than 0.01% of all of the excitation radiation on a fiber actually leaks beyond the fiber as an evanescent wave, and less that 2% of the fluorescence caused by the evanescent wave is actually recovered back into the fiber for transmission to the detector by total internal reflection (Love et al, 1991, Biosensors with Fiberoptics, D. L. Wise and L. B. Wingard (Eds.), Humana, N.J., pp. 139–180). As such, the evanescent wave mode of excitation and fluorescence signal recovery is very inefficient and not the preferred mode of operation for optical sensor devices.

For the case where the refractive index of the immobilized layer is effectively the same or greater than the index of refraction of the substrate for immobilization (e.g., the silica surface of the optical element) the boundary for TIR effectively becomes the interface between the immobilized layer and the solution. Fluorophores bound to nucleic acid in the immobilized layer are directly exposed to the electromagnetic radiation bound within the waveguide thereby providing a vastly improved excitation efficiency and, as a consequence, emit increased intensity fluorescence. For example, the index of refraction of a monolayer of organic media ($n_{monolayer}$=1.46 to 1.5; Ducharme et al, 1990, J. Phys. Chem. 94: 1925) is very similar to that of fused silica or fused silica ($n_{quartz}$=1.46; O'Hanian, H. C. 1985, Physics, W. W Norton & Co. N Y. p. 835). Fluorophores in the immobilized layer then emit fluorescence radiation within the waveguide itself to provide a much improved probability for transmission of the fluorescence signal by total internal reflection to the detector, yeilding increased sensitivity and lower target nucleic acid detection limits.

Fluorescence is the analytical method chosen for the transduction of hybridization events into a measurable analytical signal, since fluorescence techniques have long been known to provide high sensitivity (comparable to radioisotopic methods) and detailed information about structure at the molecular level (Lakowicz, 1983, Principles of Fluorescence Spectroscopy, Plenum Press, NY). Changes in the polarity, pH, temperature, microviscosity, or orientation of molecules in the local environment of a fluorophore may result in alteration of the electronic structure or collisional probabilities of the fluorophore. Such environmental changes may be detected by monitoring fluorescent signal parameters such as intensity, wavelength, lifetime, or polarization. For example, it is not uncommon for the efficiency of fluorescence emission (quantum yield) and fluorescence lifetime of an intercalant fluorophore to increase by an order of magnitude or more when inserted into the rigid and hydrophobic base stacking region of a double-stranded nucleic acids with respect to that of the unbound dye in solution.

The present invention utilizes, and is not limited to, the fluorescence intensity response of the bound fluorophore via monitoring in a total internal reflection configuration along the optical fiber substrate to quantify the presence of hybridized nucleic acids at the surface of the fiber. The fluorescence intensity is directly proportional to the amount of target nucleic acid or nucleic acid analog initially present in solution. It is also possible to use the time dependence of the rate of change of the fluorescence intensity increase upon hybridization to determine the concentration of target nucleic acid.

The fluorophore of the present invention can be for example ethidium bromide (EB). The ethidium cation (3,8-diamino-6-phenyl-5-ethyl-phenanthridium) is a fluorescent compound which strongly associates with double stranded nucleic acids by intercalation into the base-stacking region and, in some cases, the major groove of the double helical structure (Monaco et al., 1993, Journal of Bimolecular Structure and Dynamics, 10: 675). The ethidium cation is particularly well suited for investigations of nucleic acid hybridization for a number of reasons. Firstly, the quantum yield of the dye is known to increase as much as 100-fold when intercalated into the base stacking region with respect to that of the unbound dye in aqueous solution (Bauer et al, 1989, Proceedings of the National Academy of Science USA, 56: 7937). Secondly, the binding affinity and the fluorescence enhancement of the dye are independent of base composition (Cuniberti et al, 1990, Biophysical Chemistry, 38: 11). Thirdly, intercalation of the ethidium cation is known to increase duplex stability as the two 3,8-amino substituents hydrogen bond with the internucleotide phosphate groups on each of the DNA strands (whereas other intercalators are known to significantly decrease duplex stability) (Cuniberti et al, 1990, Biophysical Chemistry, 38: 11). The absorption maximum of ethidium bromide is 510 nm, which is sufficiently close to the output wavelength of 488 nm of an Ar$^+$ laser which may be used to excite the fluorophore. The dye has an emission maximum of 595 nm when bound to DNA which is a sufficiently large Stoke's shift to make separation of the emission radiation from the excitation radiation straight forward, and to prevent inner filter effects, by the use of a dichroic mirror or other standard optical components (Haugland, 1992, Molecular Probes: Handbook of Fluorescent Probes and Research Chemicals, 5th Ed:, USA: Molecular Probes Inc.). Due to the above mentioned reasons, the use of EB has been shown to provide a sensitive means to detect the presence of nucleic acid duplexes for this application.

Figure 3A:
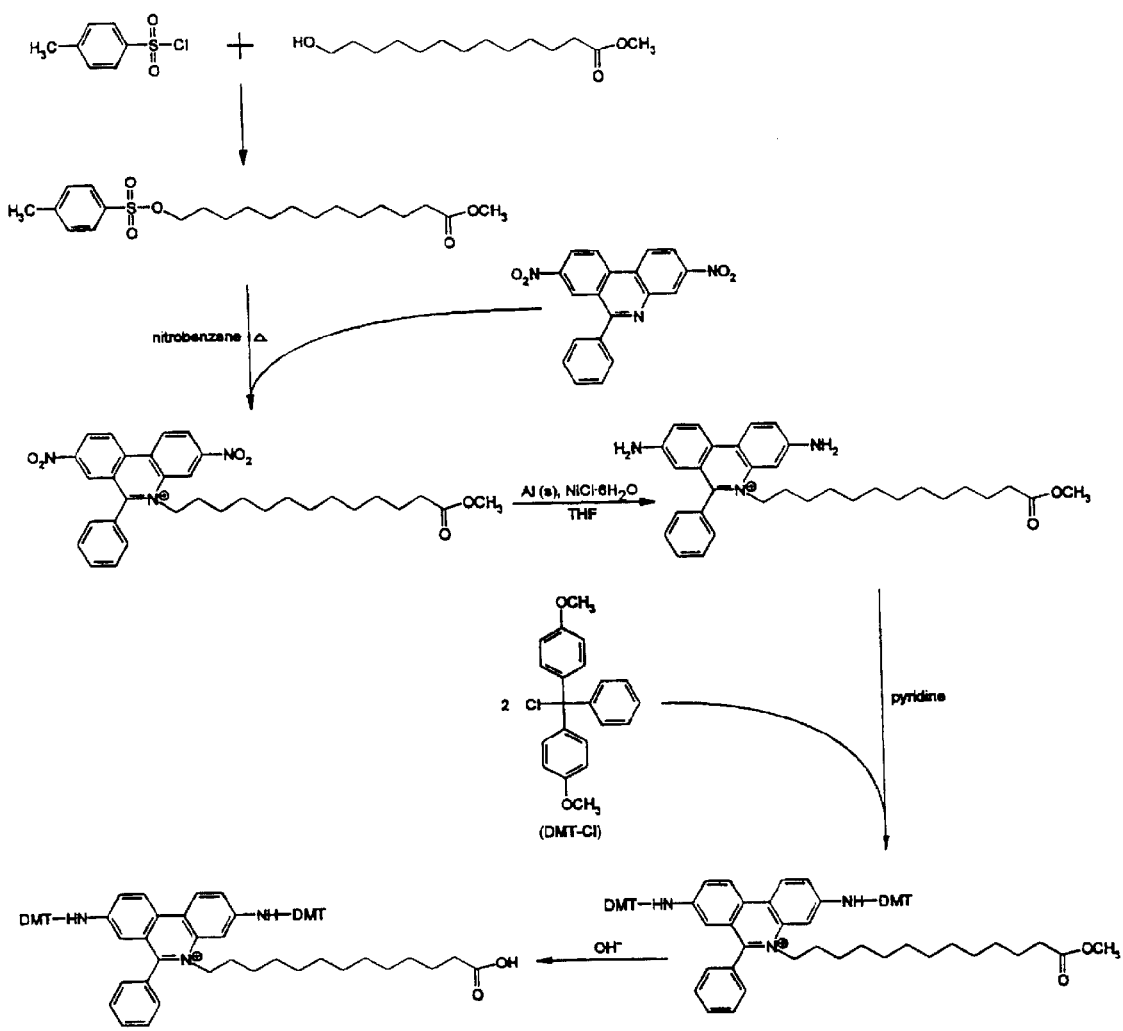
FIG. 3(*a*). Synthetic scheme used to create a hydrocarbon-tethered analogue of Ethidium Bromide.
Figure 3B:
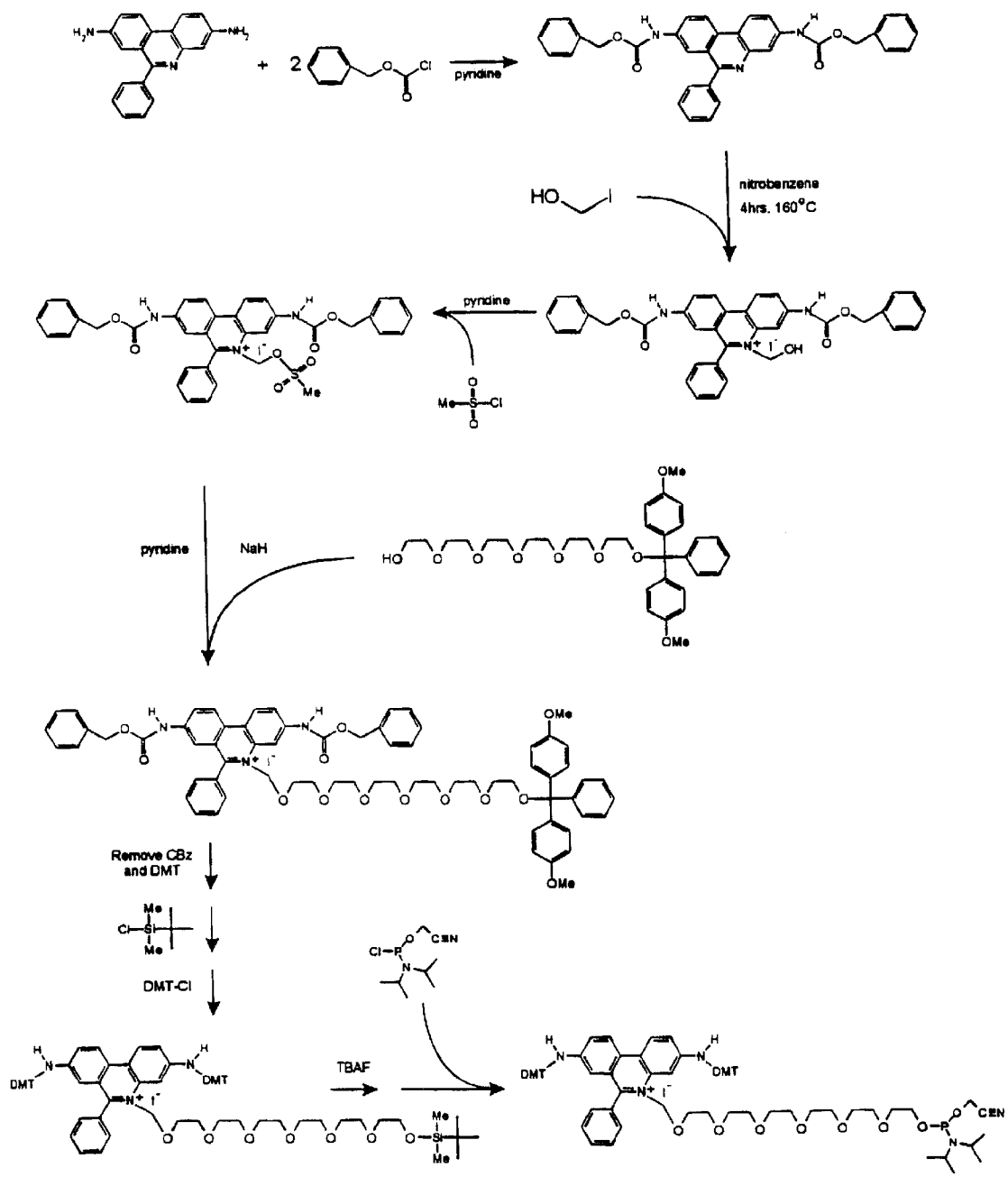
Figure 3B:
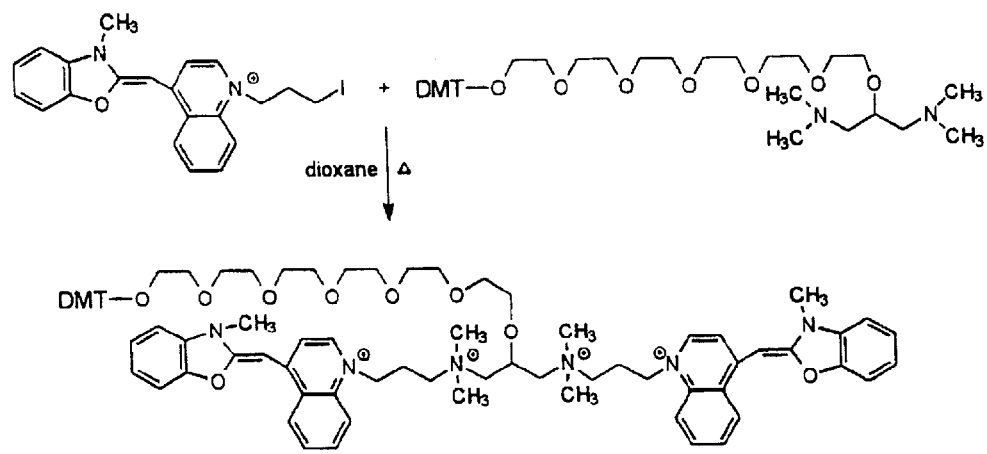

A specific example of a tethered fluorophore is illustrated in the synthetic schemes of FIG. 3a,b, and c. In this case a modified ethidium-type dye with tether, here $C_{13}$ acid moiety, is synthesized as shown (FIG. 3a). The ethidium analogue with acid tether is attached to 5'-hexylamine functionalized oligonucleotides immobilized on the surface of an optical fiber to generate the biosensor with the tethered fluorophore probe. For the case where the nucleotides are grown on the support via solid phase phosphoramidite synthesis, the 5'-hexylamine functionalization can readily be achieved through the use of the commercially available reagent Aminolink 2®.

The fluorophore or reporter group may be attached to the 5'- or 3'-end of the oligomer by not only a hydrocarbon tether but other types of tethers such as polyether, mixed aliphatic/aromatic, or peptidic. The tether need not be restricted to the 3'- or 5'-ends of the oligomer but may be attached to a terminal or internal ribo-residue via the 2'-hydroxyl (Yamana et al, 1991, Tetrahedron Letters, 32: 6347). Similarly, a tether can be attached to a terminal or internal nucleobase using pyrimidines (Pieles et al, 1990, Nucleic Acids Research, 18: 4355) or purines (Roduit et al, 1987, Nucleosides and Nucleotides, 6: 349). Furthermore, the internucleotidic linkage can be a site for tether attachment (Agrawal et al, 1990, Nucleic Acids Research, 18: 5419). Obviously, any combination of these methods could be used to site specifically incorporate multiple reporter groups.

The choice of fluorophores which may be tethered to the oligonucleotide include organic intercalating complexes, such as the commonly used nucleic acid stain ethidium bromide, thiazole orange and analogs thereof as prepared by L. G. Lee et al (1986, Cytometry 7: 508) and the YOYO, BOBO, and TOTO series of cyanine based intercalant fluorophores which are commercially available from Molecular Probes Inc. (Eugene, Ore.). Inorganic coordination complexes, such as the "molecular light switch" Ru(phen')$_2$ dppz PF$_6$ developed by Jenkins et al. (1992, J. Amer. Chem. Soc. 114: 8736) may also be used as well as groove binding dyes, such as Hoechst 33258 and Hoechst 33342, which are commercially available from Aldrich Chemical Co. (Milwaukee, Wis.). These fluorophores are chosen such that the fluorescent probe is quenched (non-emissive) when in the presence of single-stranded nucleic acids and provides intense luminescence when in the presence of double stranded nucleic acids. This change in observed luminescence occurs via changes in the relative rates of radiative and non-radiative relaxation processes of the probe when the external environment changes from aqueous solution to a hydrophobic and highly structured one in the base stacking region of double-stranded nucleic acids.

Other examples of classes of fluorophores which can be used in the present invention include acridine dyes, phenanthrides, phenazines, phenothiazines, quinolines, alfatoxin, polycyclic hydrocarbons, oxirane derivatives, actinomyces, anthracyclinones, thiaxanthenones, anthramycin, mitomycin, platinum complexes, polyintercalators, norphilin-A, fluorenes and fluorenones, furocoumarins, benzodipyrones and monostral fast blue. Preferred dyes are also those that provide large Stoke's shifts, can be excited at long wavelengths and have large differences in fluorescence lifetime, quantum efficiency, and/or wavelength of excitation and emission when in solution as compared to when bound to hybridized nucleic acids.

Light emitted from fluorophores (after direct excitation) at the surface of the fiber is preferentially coupled back into the fiber and can be monitored by a photomultiplier tube (PMT) or any other suitable light detection equipment. Increasing the length of coated fiber results in a greater optical path length and better sensitivity (Krull et al, 1991, Fiber Optic Chemical Sensors and Biosensors, Vol. II, O. S. Wolfbeis, Ed. , CRC Press, Boca Raton, pp. 315). Direct excitation of fluorophores in an immobilized layer extending from the biosensor results in improved signal to noise ratio as interferences from background fluorescence in the bulk environment are avoided.

Figure 4A:
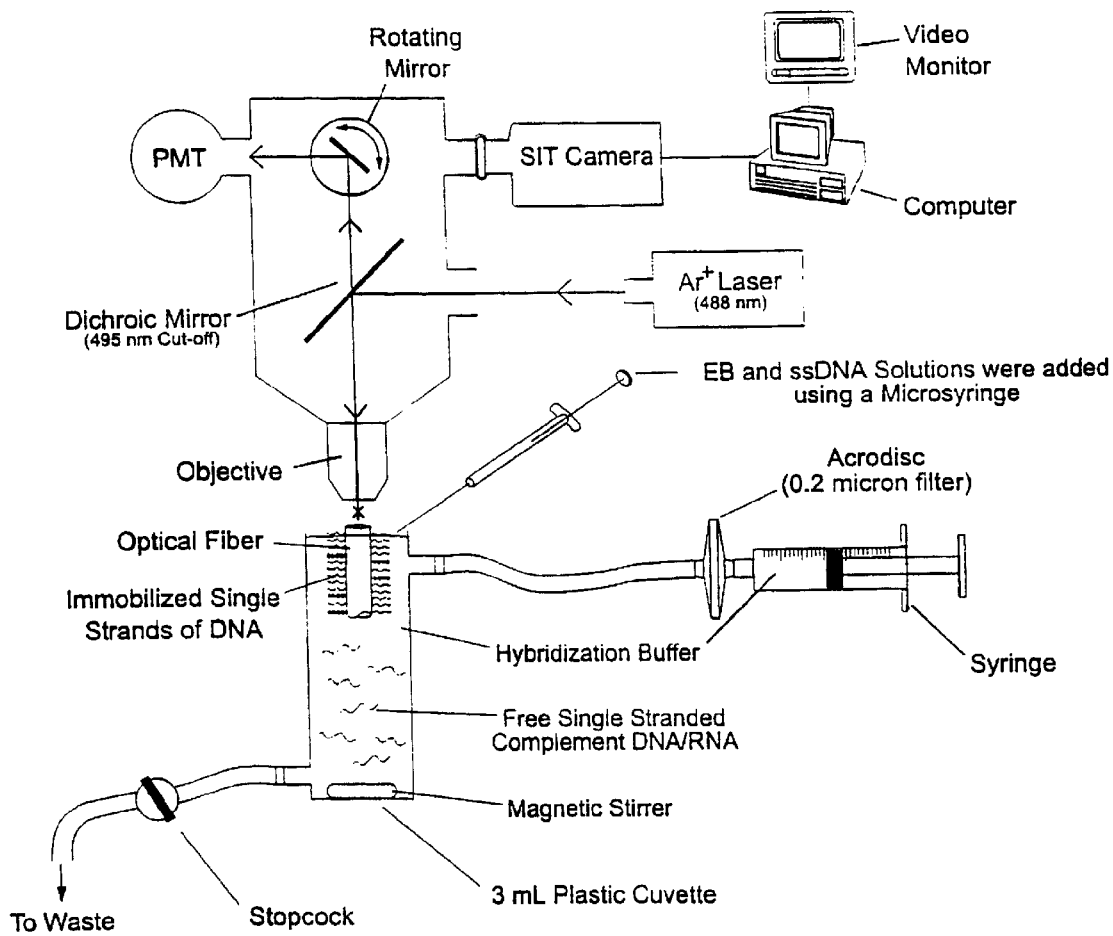
FIG. 4(*a*). Schematic diagram of one embodiment of an apparatus used to measure fluorescence intensity from optical fibers coated with immobilized DNA.
Figure 4B:
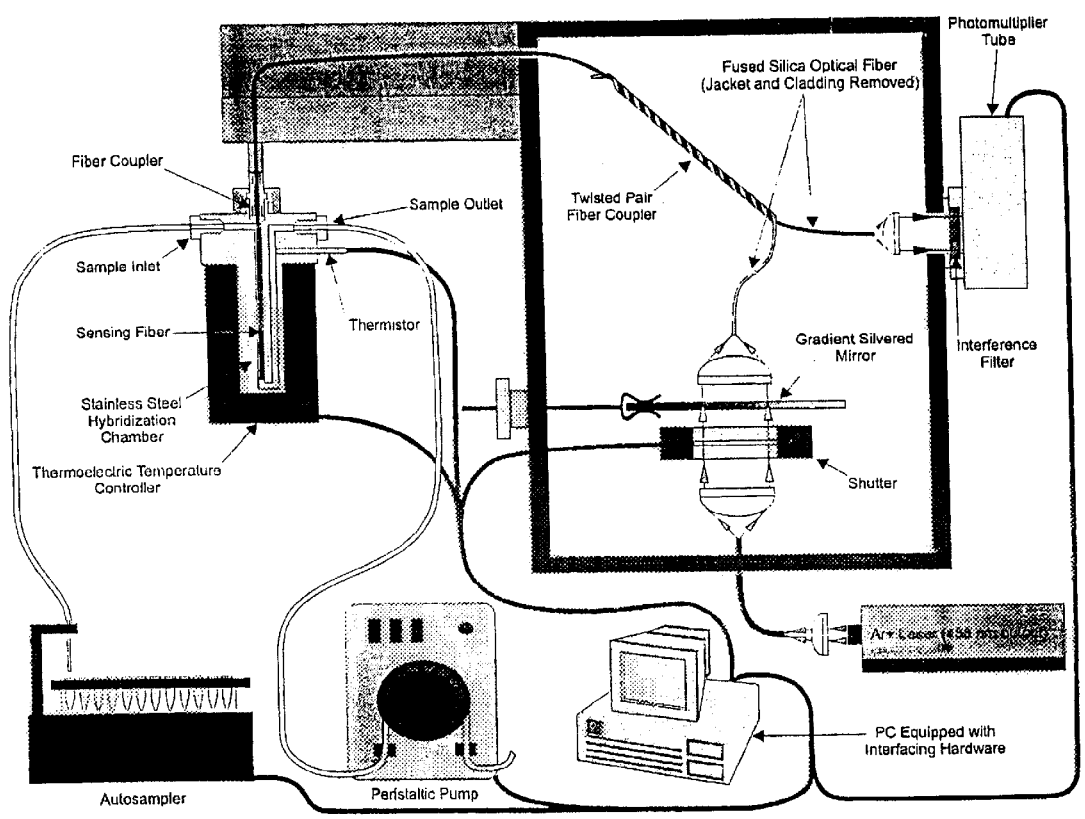

One instrument used for fluorescence intensity measurements is based on a fluorescence microscope as described elsewhere (Brennan et al, 1990, Anal, Chim. Acta., 237: 253) and shown in FIG. 4(a). An instrument as shown in FIG. 4(b) may also be used in which the output from a suitable light source, for example an argon ion laser, is directed into an optical fiber via a lens with a numerical aperture which is equal to or greater than the numerical aperture of the nucleic acid functionalized waveguide when in the hybridization buffer solution used for analyte detection. The excitation radiation may be coupled into a delivery fiber via a twisted optical fiber waveguide assembly such that all modes carried by the first fiber into which the excitation radiation was first coupled would be delivered to the second fiber to provide optimal excitation of fluorophores associated with the biosensor. The excitation radiation may be totally internally reflected along the length of the delivery fiber to a sensing fiber functionalized with immobilized oligonucleotide and fluorophore. Coupling of the radiation between fibers may be achieved by abutting the distal terminus of the delivery fiber to the proximal terminus of the sensing fiber in a suitable non-fluorescent fiber coupler. The terminus of the coupler is preferentially designed as a compression-fit end which provides a solution-tight seal to prevent contaminants from diffusing into the fiber coupler and causing drift in the analytical signal. The sensing fiber is situated within in a small volume, stop-flow, hybridization chamber made of a suitable inert material with good thermal conductivity (e.g. stainless steel or titanium). The temperature of the hybridization may be controlled by use of a suitable thermoelectric housing to provide rapid thermostating to the desired temperature and computer control. The temperature of the solutions in the hybridization cell may be accurately determined (±0.2° C.) by use of a glass encapsulated thermistor incorporated into the hybridization cell. Solutions delivery to the hybridization cell and sensing fiber may be done by use of a computer controlled pump (e.g. peristaltic pump) where all solutions originate from a computer controlled autosampler. Fluorescence emission from fluorophores associated with immobilized nucleic acid complexes was totally internally reflected within the sensing fiber. The portion of the light coupled back into the delivery fiber was directed towards an interference filter with the appropriate bandpass window for the emission of the fluorophore used with the optical sensor. Fluorescence radiation traversing the interference filter then enters a photomultiplier tube to provide a quantitative measure of the fluorescence intensity. In alternative embodiments, the radiation source can be a frequency doubled laser, a semiconductor laser, bright lamp or LED. Coupling into the waveguide can be accomplished with fiber couplers, and the detector can be an avalanche diode rather than a PMT.

Figure 5:
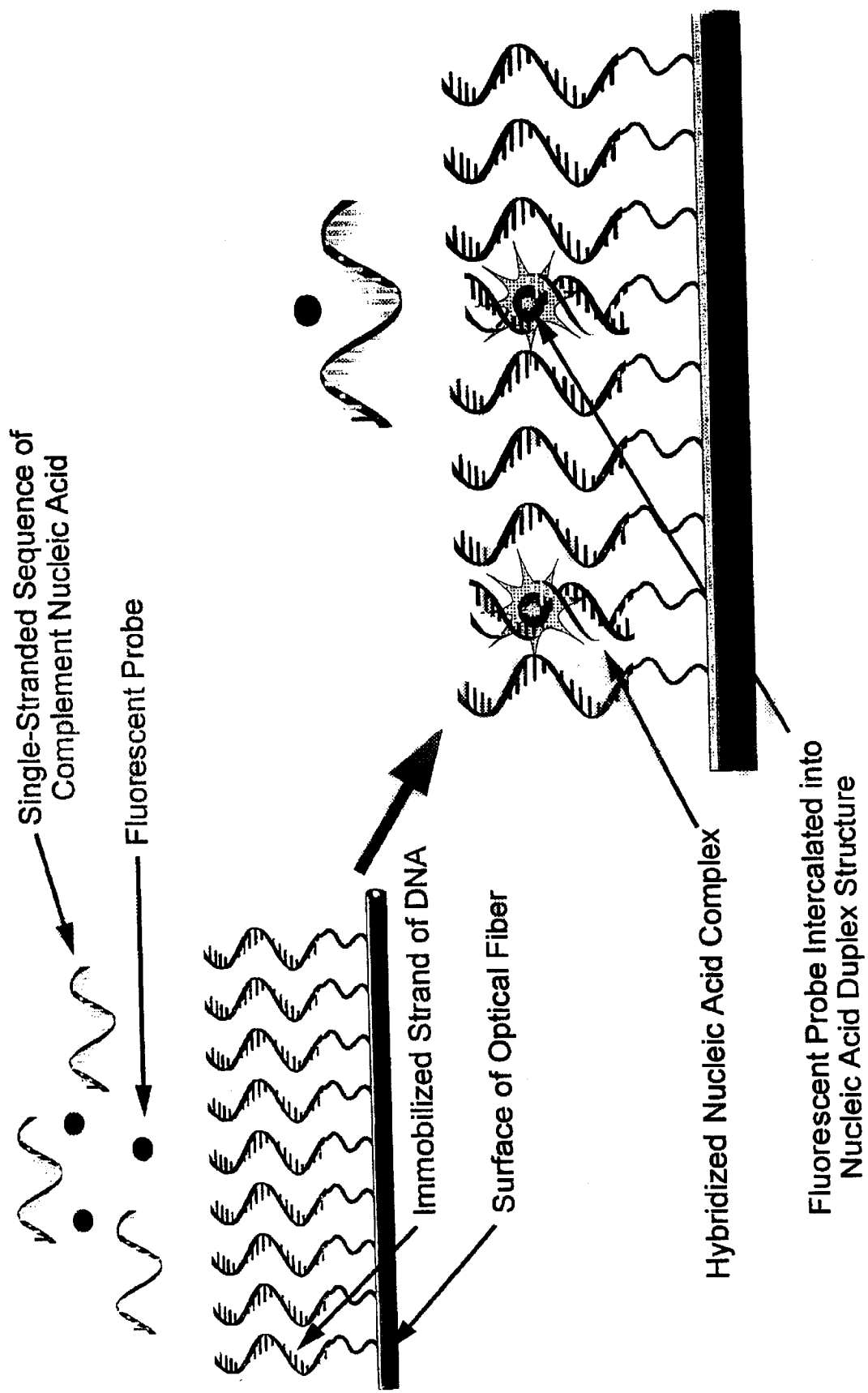
FIG. 5. Illustration of the operating principles of the fiber-optic nucleic acid biosensor. Hybridization of complement single-stranded oligonucleotide from solution with immobilized nucleic acid probe on biosensor is followed by intercalation of the tethered fluorescent ligand which provides transduction of the selective binding process into a measurable analytical signal.

In one embodiment of the invention the biosensor operates as follows. The optical fiber with attached fluorescently labeled single-stranded nucleic acid is placed in a flow through cell and immersed in hybridization buffer solution. When single-stranded nucleic acids or nucleic acid analogs which are complementary to the immobilized strands are introduced to the flow cell, hybridization occurs followed by intercalation (or other suitable ligand binding motif) and enhanced fluorescence emission of the attached fluorescent probe, as illustrated in FIG. 5. Fluorescence intensity is monitored in a total internal reflection configuration wherein the optical fiber and organic coating form a waveguide to provide excitation to the surface immobilized nucleic acid and fluorescent probe, as well as to collect fluorescence emission. By monitoring the fluorescence intensity from the fiber, a measure of the amount of target nucleic acid in solution can be determined.

Regeneration of the biosensor can be achieved by thermal methods such as by elevating the temperature within the flow-through hybridization cell or by chaotropic methods in which solutions of highly polarized salts alter the hydrogen bonding structure of the solution to affect denaturation of the hybridized complex. In either case, the complex stability in the system is reduced to the point where hybridization is not energetically favorable and the complement strands are dissociated from the covalently immobilized oligomers and may be flushed out of the flow cell. Regeneration methods as described herein can be employed to recycle biosensors.

Figure 6:
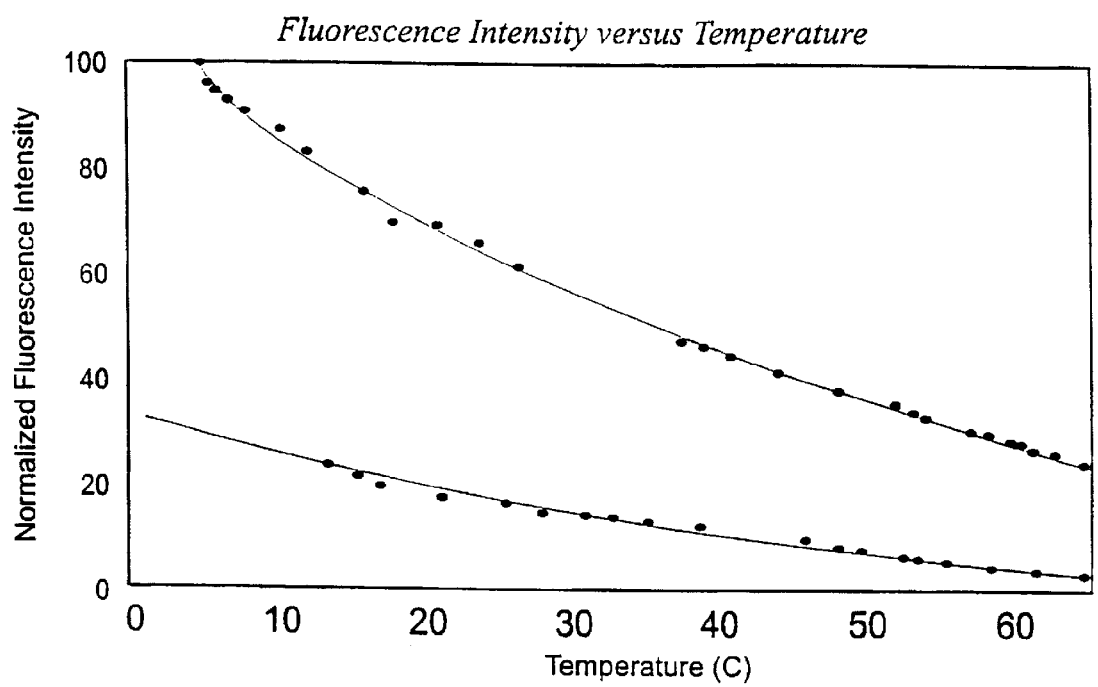
FIG. 6. Fluorescent intensity as a function of temperature for the mixed base sequence icosanucleotide functionalized fibers. Upper Curve: response of the optical sensor to 20 pmol of linear complement icosanucleotide in the presence of $2.5 \times 10^{-8}$ M ethidium bromide. Lower Curve: response of the optical sensor to $2.5 \times 10^{-8}$ M ethidium bromide.
Figure 7:
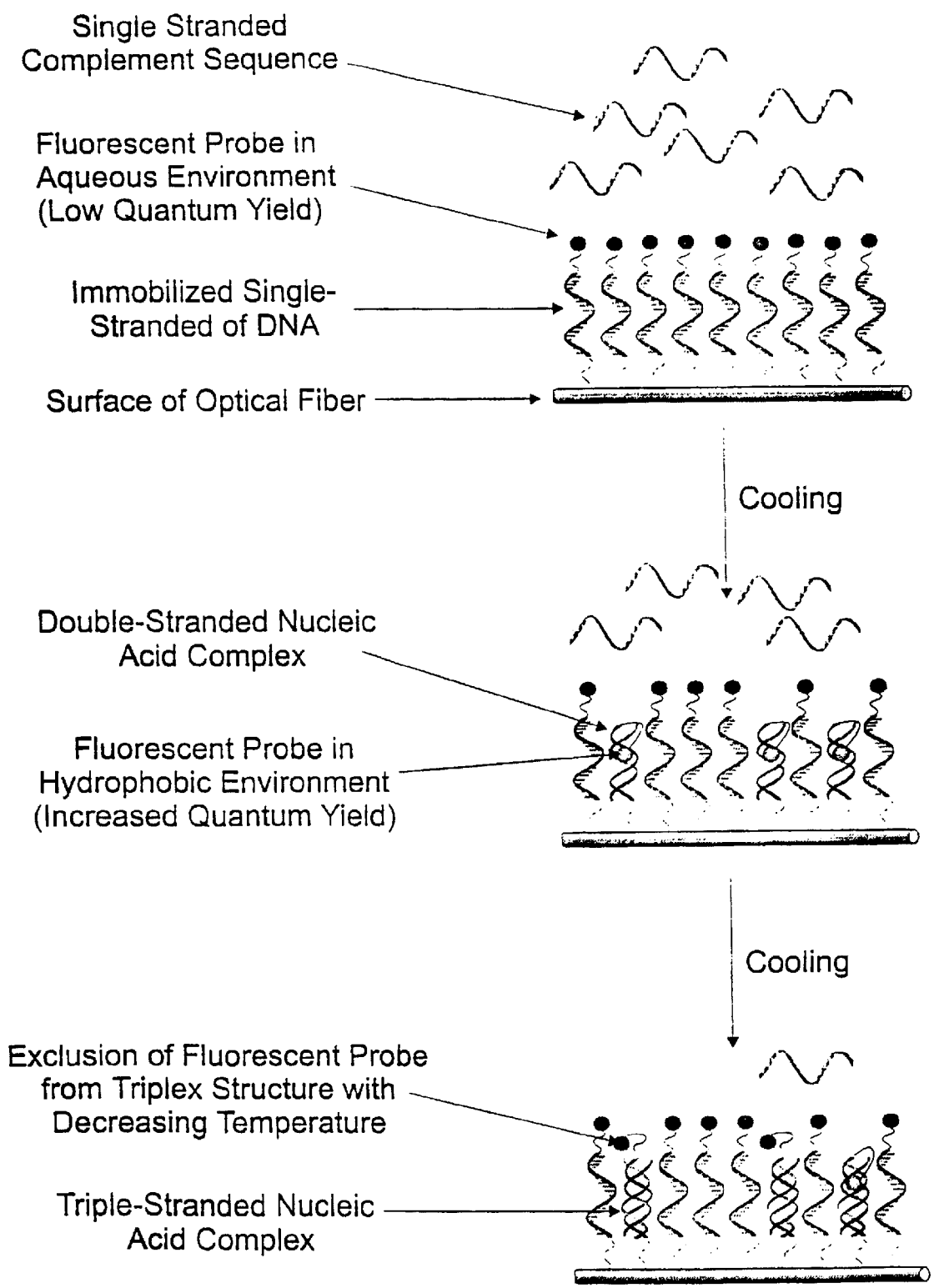
FIG. 7. (a) A Model of parallel (T*AT) triplex formation using $dT_{10}$ and an optical biosens or functionalized with immobilized $dA_{10}$. $dT_{10}{:}dA_{10}$ duplex is first formed upon cooling the system below the duplex $T_m$ followed by formation of the triple-stranded complex with further cooling below the $T_m$ for triplex formation. (b) The $dA_{10}$ of the optical sensor capturing the branched "V" compound 1 (see FIG. 15). Note how the fluorescent probe is excluded from the triplex as the temperature is cooled.
Figure 7:
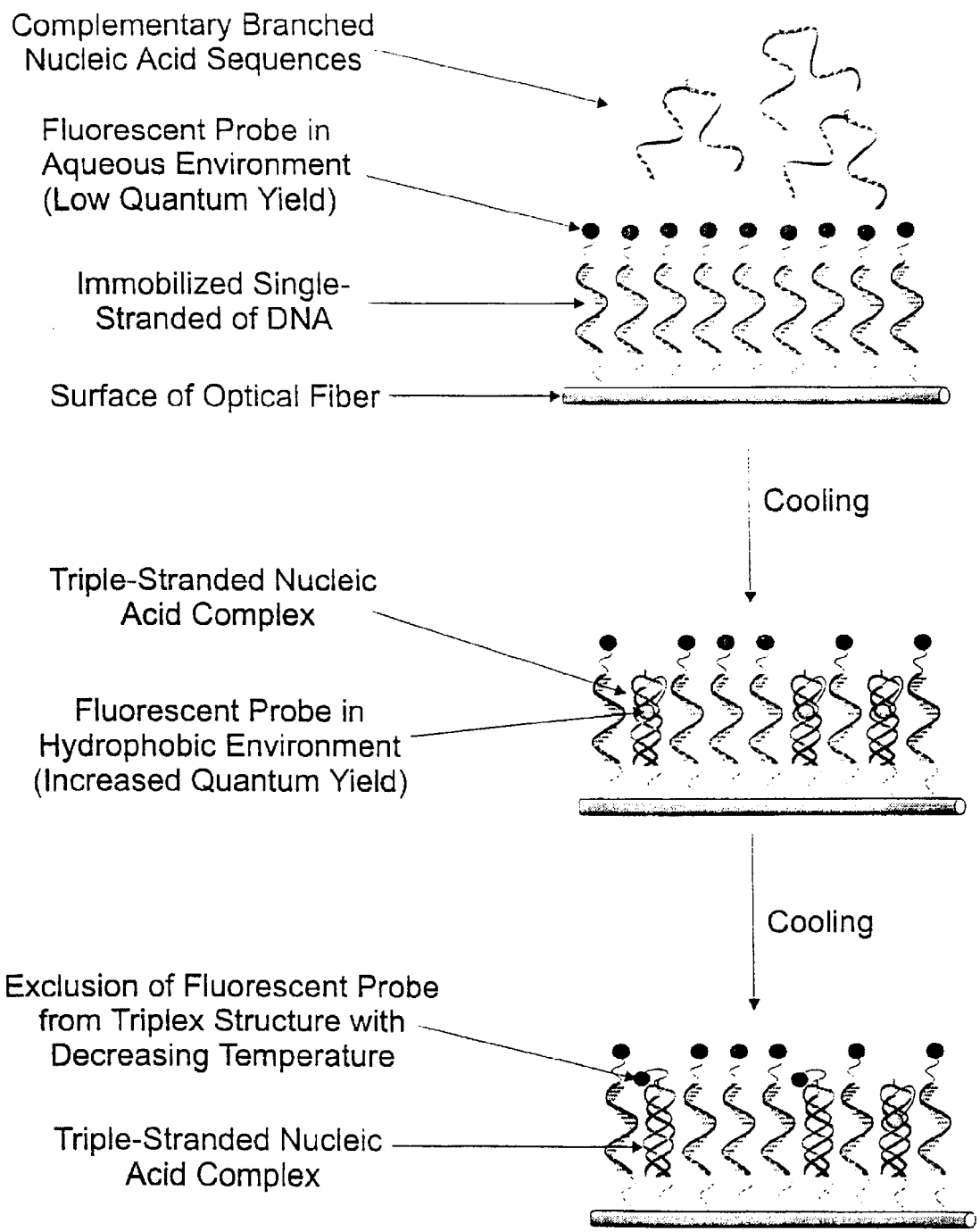

Formation of multi-stranded nucleic acids (i.e. nucleic acid complexes composed of 3 or more strands), such as triplex nucleic acids, may be determined from the temperature dependence of the fluorescent signal. Normally, the fluorescence efficiency of a fluorophore increases with decreasing temperature owing to the reduced collisional deactivation as a consequence of the reduced kinetic energy of the molecules surrounding the fluorophore. Fluorescence efficiencies with negative temperature coefficients are readily observed for fluorophores in solution and well as for fluorophores intercalated into nucleic acids, as illustrated in FIG. 6. When multi-strand formation occurs, (e.g. binding of a third strand in the major groove of a double-helical nucleic acid) exclusion of the bound ligand often follows as the partition coefficient for the fluorophore in the multi-stranded nucleic acid is often much reduced with respect to that of the same fluorophore in double-stranded nucleic acid. The ligand exclusion process will also show a temperature dependence where reduced ligand binding is observed as the temperature of the system is decreased. As such, a positive temperature coefficient of fluorescence intensity would be observed for fluorophores associated with multi-stranded nucleic acids as increasing amounts of fluorophore become excluded from the highly-structured environment within the nucleic acid complex into bulk solution where the probability for collisional quenching of fluorescence is far greater. A net positive temperature coefficient of fluorescence intensity would then be observed for a fluorescent nucleic acid binding ligand in a multi-stranded nucleic acid. The temperature at which multi-strand formation occurs could also be assayed from the maxima in a fluorescence intensity versus temperature plot where the temperature coefficient changes from negative (for the dye bound in double-stranded nucleic acid) to positive (for the dye being excluded from the multi-stranded nucleic acid complex). This process is illustrated in FIGS. 7(a & b) for triplex formation on the sensor surface with linear and branched nucleic acids.

The biosensor of the present invention provides for rapid clinical testing for viruses (e.g., HIV, T cell lymphotropic virus 1 and 2, hepatitis B and C), and pathogenic bacteria (e.g. *E. coli.*, Salmonella, Listeria, Chiamydia ssp., *Trichomonas vaginalis, Gradenerella vaginitis*) as well as other microorganisms. Detection of genetic disorders (e.g., cystic fibrosis and sickle-cell anemia) and diseases such as cancer is also done with the method and apparatus of the present invention as well as potential therapeutics to treat such diseases (e.g. branched antisense nucleic acids which inhibit expression of targeted nucleic acid sequences via triplex formation with that particular sequence, effectively shielding the genetic information from being read by transcription enzymes).

The biosensor is useful for the monitoring of the in-vivo response of bacteria to an antibiotic treatment to ensure the efficacy of the treatment regime. The physician, based on past experience, chooses both the antibiotic and the dosage to treat a bacterial infection. Samples of the infecting organism would be sent to the laboratory for MIC testing, Minimal Inhibitory Concentration for the lowest concentration of that particular antibiotic necessary to inhibit the growth of the infecting organism. If the MIC of the in-vitro test is less than the dosage given to the patient, the treatment is allowed to continue, otherwise an increased dose and/or a change of antibiotic would be ordered. The most significant problem of this approach is that of the time required, wherein 1 to 3 days are needed to acquire the MIC result. Secondarily, it is a test of an in-vitro response to reflect an in-vivo situation. Using larger doses than necessary is not a reasonable treatment, as most antibiotics are toxic to the patient as well. Further the use of inappropriate antibiotics or doses can encourage the development of drug resistance in the infectious organisms.

The biosensor described above overcomes these problems by determining the concentration of one or more species of bacteria present in the patient. Samples would be taken at intervals and tested for the bacteria's concentration. The change in the bacterial concentration over time would reflect the efficacy of the antibiotic treatment against the infectious organism or organisms. This ensures that an adequate amount of an appropriate antibiotic would be provided to the patient without providing excessive amounts of the antibiotic. The method described above may be used in a variety of situations to monitor response of organisms such as bacteria or fungi to drugs.

EXAMPLES

Example 1

Preparation of Fused silica Optical Fibers Derivatized with Long Chain Aliphatic Spacer Molecules Terminated with a 5'-0-dimethoxytrityl-2'-deoxythymidine Nucleoside Plastic-clad silica optical fibers with a diameter of 400 $\mu$m were purchased from 3M Specialty Optical Fiber (North York, ON, Canada). The cladding on the fibers was mechanically removed, and the fibers were cut to lengths of about 1 cm. One face on each fiber was polished by suspending the fiber over (and placing the end face of the fiber in contact with) the rotating plate of a Thermolyne type 37600 speed controlled mixer (Sybron Corporation, Dubuque, Iowa, USA) onto which 1200 grade emery paper was immobilized. All fused silica optical fibers were cleaned using a Harrick PDG-32G plasma cleaner (Harrick Scientific Corporation, Ossining, N.Y., USA) before activation with aminopropyltriethoxy silane (APTES).

The fibers were then washed with a 1:1 acetone/methanol mixture and stored in a vacuum desiccator The optical fibers were plasma cleaned for 5 minutes at low power (40 W) and were placed in a solution of 1:200 (v/v) aminopropyltriethoxy silane (APTES) in dry toluene This was done under a nitrogen atmosphere using glassware which was oven dried and previously treated with octadecyltrichlorosilane. The structure of the APTES coatings on fused silica substrates has previously been investigated by Vandenberg et al. (1991, J. Colloid and Interface Sci., 147: 103). The method of Arnold and co-workers (1989, Collect. Czech. Chem. Commun., 54: 523) was used to synthesize an aliphatic spacer arm terminated with 5'-O-dimethoxytrityl-2'-deoxythymidine. In this method 1,10-decanediol was condensed with succinic anhydride to form 1,10 decanediol bis-succinate, as illustrated in FIG. 1(a). The bis-succinate was reacted with N-hydroxysuccinimide and 5'-O-dimethoxytrityl-2'deoxythimidine in the presence of N,N'-dicyclohexyl-carbodiimide (DCC) and 4-dimethylaminopyridine (DMAP) to yield a nucleoside functionalized spacer molecule. The spacer was then attached to the surface of the APTES treated optical fiber via amide formation.

Example 2

Preparation of Fused silica Optical Fibers Derivatized with Glycidoxypropyltrimethoxysilane Extended with Mono-Dimethoxytritylated Hexaethylene Glycol Substrate Linker Molecules

In order to grow oligonucleotides onto the surface of silica substrates (such as fused silica) by automated solid phase synthesis, the surface is functionalized with spacer molecules of at least 25 Å in length which had either an amine or a hydroxyl functionality at the terminus of the spacer molecule. A chemically resistant, non-hydrolyzable spacer molecule is employed. The method used was a modification of that reported by U. Maskos and E. M. Southern supra wherein the silica surface was treated with glycidoxypropyltrimethoxysilane (GOPS), followed by extension via treatment with hexaethylene glycol (HEG) under acidic conditions. For the purpose of creating biosensors with higher sensitivity and lower detection limits, this method is advantageous over the use of hydrocarbon tethers. The water soluble HEG linker will provide a more fluid environment (which should not self-assemble) so as to improve the ability of the immobilized DNA strands to hybridize with complementary material in solution (in terms of energetics and kinetics). The hydrophilicity of the linker will also facilitate the removal of adsorbed contaminants (e.g. proteins, organics) which may occlude the surface and contribute to drift in the fluorescence intensity. However, as HEG is bifunctional, there exists the possibility of creating non-reactive closed-loop structures which may significantly decrease the loading of oligonucleotides on the surface of the fibers. In order to eliminate this problem, one terminus of the HEG is protected with a dimethoxytrityl functionality prior to extension with GOPS. This strategy permits facile determination of the amount of support linkers bound to the silica surface. Removal of the trityl protecting groups by treatment with acid yields the highly colored trityl cation, which can be quantitatively measured by monitoring $A_{(504\ nm)}$ of the deprotection solution. Knowing there is one trityl group released per linker molecule attached to the surface, the loading of HEG can easily be determined. Immobilization of a protected linker molecule provides the additional advantage that the hydroxyl groups produced after the attachment of the HEG to the epoxide moiety and all other surface silanols can be capped to prevent unwanted oligonucleotide growth at these sites. The presence of side product oligonucleotides, which are prematurely terminated due to the lack of a suitable support molecule, may decrease the sensitivity and selectivity of the sensor. The additional charge imparted from the anionic backbone of a side product strand may inhibit hybridization between the analyte strands and neighboring probe sequences. See: R. T. Pon *Methods in Molecular Biology*, Vol.20: Protocols for Oligonucleotides and Analogs, S. Agrawa, Ed, 1993, Humana Press, Inc. Totowa N.J. In conjunction with the use of non-hydrolyzable spacer molecules, t-butylphenoxyacetyl protected phosphoramidite synthons were employed. This labile protecting group can be quickly removed (15 min @ 55° C. or 120 min. at room temperature as compared to 12–16 hours @ 55° C. using 27% aqueous ammonia) thereby reducing the possibility of cleavage of the immobilized sequences by hydrolysis of the silyl ether bonds which ultimately anchor the strands to the fiber surface.

i) Gleaning of Silica Substrates Prior to Functionalization with GOPS:

The buffer coating was mechanically stripped from the pre-cut optical fiber pieces (400 μm diameter×44 mm) and the cladding was dissolved by treatment with acetone. The fused silica substrates, i.e., optical fibers or wafers, were added to a 1:1:5 (v/v) solution of 30% ammonium hydroxide/30% hydrogen peroxide/water and the mixture was stirred at 80° C. for five minutes. The substrates were then removed and treated with a solution of 1:1:5 (v/v) conc. HCl/30% hydrogen peroxide/water and the mixture stirred at 80° C. for five minutes. The substrates were then sequentially washed with methanol, chloroform and diethyl ether, respectively, and dried in-vacuo.

ii) Synthesis and Purification of mono-dimethoxytritylated hexaethylene glycol (DMT-HEG):

Dimethoxytrityl chloride (7.1 g) was dissolved in 10 ml of dry pyridine and added dropwise to a stirred solution of hexaethylene glycol (5.65 ml) in 5 ml of dry pyridine under an argon atmosphere. Stirring was continued for 16 hours after which time the reaction mixture was combined with 50 ml of dichloromethane. The dichloromethane solution mixture was twice shaken with 900 ml portions of 5% aqueous sodium bicarbonate and then with three 900 ml portions of water in order to remove unreacted HEG, pyridine, and pyridinium salts. The product was purified by liquid chromatography using silica gel and a solvent system of 0.1% triethylamine in 1:1 dichloromethane/diethyl ether. The identity of the product was confirmed by proton NMR spectroscopy (200 MHz).

iii) Functionalization of Fused Silica Substrates with 3-Glycidoxypropyltrimethoxysilane (GOPS):

The cleaned fused silica substrates were suspended in a stirred solution composed of 40 ml xylene, 12 ml GOPS, and a trace of Hünig's base at 80° C. overnight. The fibers were then sequentially washed with methanol, chloroform, ether, and then dried in-vacuo.

iv) Linkage of DMT-HEG to GOPS Functionalized Silica Substrates:

The GOPS functionalized fibers were suspended in a stirred solution of 1:4:8 (v/v) DMT-HEG/diethyl ether/toluene containing a catalytic amount of sodium hydride under an argon atmosphere. The reaction mixture was stirred for 14 days after which time the fibers were removed and washed sequentially with methanol, chloroform, ether, and then dried in vacuo.

v) Capping of Unreacted Silanol and Hydroxyl Functionalities with Chlorotrimethyl-silane:

The fused silica fibers functionalized with DMT-HEG were suspended in a solution of 1:10 (v/v) chlorotrimethylsilane/pyridine for 16 hours under an argon atmosphere at room temperature.

Example 3

Preparation of Fused Silica Optical Fibers Derivatized with Mono-Dimethoxytritylated Hexaethylene Glycol Substrate Linker Molecules via Mesylate Activation

The details of the preparation of the fused silica substrates and DMT-HEG synthesis are provided in example 2(i and ii). DMT-HEG (0.5 g) was suspended in 50 ml anhydrous pyridine. The solution was maintained under an anhydrous argon atmosphere and stirred. while 1.2 equivalents of methanesulfonyl chloride was added dropwise. The reaction allowed to proceed for 60 minutes at room temperature with stirring. The cleaned fused silica and silicon substrates were introduced into the solution containing the mesylated DMT-HEG and the substrate functionalization reaction allowed to proceed for 4 days with stirring at 40° C. under an argon atmosphere. Following the 4 day incubation period, the solution was decanted away from the functionalized substrates which were then washed with copious amounts of dichloromethane. Washings were continued until no discernible absorbance at 504 nm was observed from the wash solution made acidic by treatment with trichloroacetic acid. The functionalized substrates were then capped as per the methods of example 2(v) and stored in-vacuo and over $P_2O_5$ until needed.

Example 4

Preparation of Fused silica Optical Fibers Derivatized with Mono-Dimethoxytritylated Hexaethylene Glycol Phosphoramidite Substrate Linker Molecules via Standard β-Cyanoethylphosphoramidite Coupling on an Automated Synthesizer The details for the preparation of the fused silica substrates and DMT-HEG are provided in example 2(i) and 2(ii), respectively. DMT-HEG (0.5 g) was suspended in a solution consisting of 12 ml of anhydrous THF and 4 ml of anhydrous N,N-diisopropyl ethylamine. The solution was maintained under an anhydrous argon atmosphere and stirred at all times. 1.1 equivalents of 2-cyanoethyl-N,N-diisoproylamino-phosphochloridite was added dropwise to the DMT-HEG solution and the reaction allowed to proceed for 90 minutes at room temperature. TLC analysis (1:1 $CH_2Cl_2$/diethyl ether) indicated quantitative formation of the DMT-HEG phosphoramidite synthon ($R_f$=0.7). The reaction product was thrice extracted into ethyl acetate from a 5% sodium bicarbonate solution. The organic phase was separated from the aqueous layer, dried over $NaSO_4$, filtered and the solvent removed under reduced pressure. The product was then stored dry and at −20° C. under an anhydrous argon atmosphere until required. Functionalization of fused silica substrates was then done as part of a standard coupling cycle using the automated solid phase DNA synthesizer and a 0.1 M solution of the DMT-HEG phosphoramidite in anhydrous THF. The methods for automated oligonucleotide synthesis are detailed in example 5. The capping procedure detailed in example 2(v) was then done in order to block any undesired reactive sites on the substrates.

Example 5

Synthesis of Oligonucleotides onto Substrate Linker Functionalized Fused Silica Waveguides All DNA synthesis was done by the well established β-cyanoethylphosphoramidite method with an either an Applied Biosystems 381A or 391 EP DNA Synthesizer using susbtrate linker functionalized controlled-pore glass beads, fused silica optical fibers, planar fused silica wafers, or planar silicon wafers. Automated solid-phase DNA synthesis is well known and is described in detail elsewhere (Beaucage et al., 1992, Tetrahedron Letters, 48: 2223–2311; *Oligonucleotides and Analogues; A Practical Approach*, F. Eckstein, Ed. Oxford University Press, NY, 1991). The substrate linker functionalized optical fibers were placed into an emptied Applied Biosystems (ABI) Oligonucleotide Purification Cartridge column (OPC-column) or 10 μmol scale synthesis column with the dead volume being taken up by inert polyethylene pieces. The end filter papers were replaced (ABI) and the column ends were crimped closed using aluminum seals. Synthesis of oligomers onto the optical fibers was carried out at the 0.2 μmol. scale with a pulsed-delivery cycle in the "trityl off" mode. The β-cyanoethylphosphoramidite cycle was used as supplied by ABI with the exception of extended nucleoside coupling times (2–10 min.) and increased solution delivery times to accommodate the larger synthesis columns. With the exception of thymidine synthons, t-Butylphenoxyacetyl protected phosphoramidite synthons were used in conjunction with a t-butylphenoxyacetic anhydride capping solution as supplied by Millipore Inc.

In the case where polythymidilic acid oligonucleotides were grown on the optical fibers, deprotection of the phosphate blocking groups from the immobilized oligomer was achieved by standing the fibers in a solution of 2:3 triethylaminelacetonitrile at room temperature for 1.5 hours. This procedure caused the loss of the phosphate blocking group via β-elimination while not cleaving the singlestranded DNA (ssDNA) from the optical fibers. In the case where oligonucleotides containing bases other than thymine were grown, the following protocol was used for phosphate and nucleobase deprotection. A 30% ammonium hydroxide solution was drawn up into the synthesis column containing the optical fibers functionalized with immobilized oligonucleotides using a syringe and a male-to-male luer adapter. The fibers submerged in ammonia were allowed to stand for two hours at room temperature after which time the ammonia solution was expelled from the column and the contents of the column were washed five times with 5 ml portions of sterile water. The deprotection solutions and washings were collected and concentrated to a total volume of 1 ml. $A_{260\,nm}$ of the concentrated deprotection solution was measured in order to determine the quantity of DNA liberated from the fused silica substrates. Based on the results of the trityl cation assay and $A_{260nm}$ of the deprotection solution, it was found that ~20% of the oligomers remained attached to the surface following the ammonia deprotection procedure. In the case where oligonucleotides of mixed base sequence were grown onto optical fibers, the oligonucleotide sequence was (5'-TAG GTG AGA CAT ATC ACA GA-3'SEQ ID NO: 1), which is a nucleic acid probe for the E03 forward sequence of the *Candida albicans* genome.

Fibers coated in ssDNA were either stored dry or kept in a solution of 1:1 ethanol/water. All fibers were cleaned prior to use by sonication in a solution of 1:1 ethanol/water for 5 minutes in order to remove any fluorescent contaminants adsorbed to the surface of the fibers.

Example 6

Biosensor Characterization by Trityl Cation Assay

All oligonucleotide syntheses were evaluated by spectroscopic quantitation of trityl cation released during the trichloroacetic acid treatment steps of the automated synthesis. The collected fractions of trityl cation were diluted with 2.0 ml of 5% TCA in 1,2-dichloroethane immediately prior to making absorbance measurements. Absorption at 504 nm was measured in order to determine the concentration and the total number of trityl cation moieties released during each TCA deprotection step of the synthesis. In this way, the total number of oligomers successfully grown onto the solid supports was determined.

Figure 8:
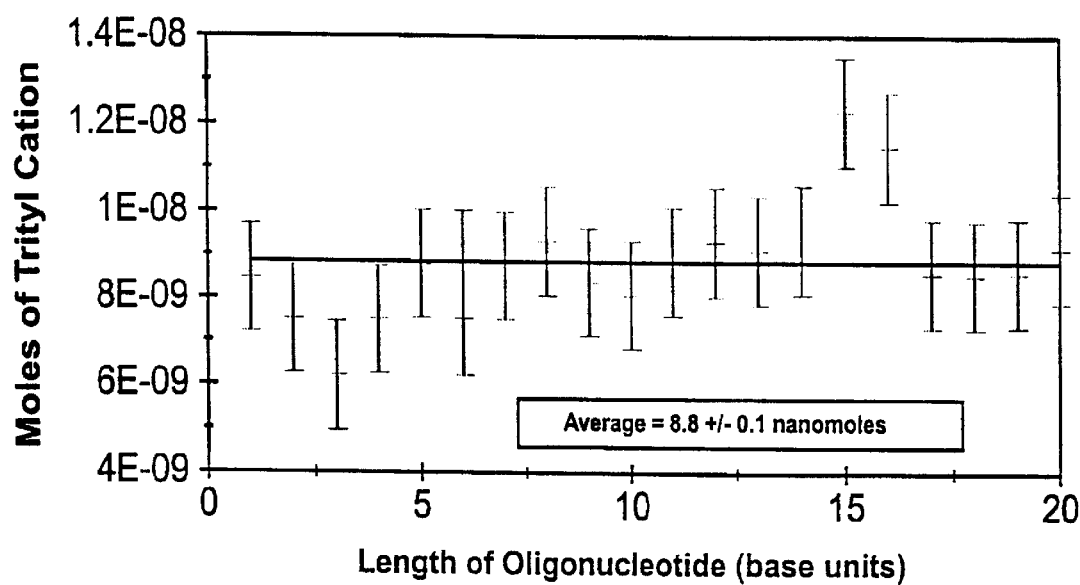
FIG. 8. Quantity of trityl cation released during each detritylation step of the automated phosphoramidite synthesis of $dT_{20}$ onto fused silica optical fibers functionalized by the protocols of examples 1 and 5.

As there exists no discernible decrease in the amount of trityl cation released during successive deprotection steps, it may be safely assumed that the coupling efficiency of 99.5% or better suggested by the manufacturer of the automated synthesizer (ABI) was achieved. The results of a trityl cation assay for a synthesis of $dT_{20}$ onto optical fibers by the methods given in Examples 1 and 5 are shown in FIG. 8.

Example 7

Generation of Complementary and Non-complementary Nucleic Acids

Synthesis of $dA_{20}$ and $rA_{20}$ was done using a conventional LCAA-CPG support with the β-cyanoethylphosphoramidite cycle supplied by ABI. A nonadecamer of random base composition ($dR_{19}$) was also prepared by simultaneously introducing all four phosphoramidite reagents to the column at each coupling step. Standard deprotection with aqueous ammonia (29%, 1.5 ml, 24 h) was used to liberate the oligomers from the solid support and remove the base protecting groups. For the case of the $rA_{20}$, deprotection of the phosphate blocking groups, base protecting groups and cleavage from the CPG support was done by treating the oligomers with 1.5 ml of a solution consisting of 4 parts aqueous ammonia and 1 part ethanol for 48 hours at room temperature. The aqueous solution containing the. oligonucleotides was then collected, evaporated to dryness, and the residue treated with 300 μl of an anhydrous solution of 1 M tetra-N-butyl ammonium fluoride in THF overnight at room temperature. After the incubation time, the reaction was quenched by adding 1 ml of water to the reaction mixture. Crude oligomer was purified by polyacrylamide gel electrophoresis and reverse phase liquid chromatography or size exclusion chromatography.

Example 8

Detection and Quantification of Complement DNA (cDNA), Complement RNA (cRNA) and Non-complement Nucleic Acid by the Optical Sensor Fabricated by the Procedures of Examples 1 and 5

An optical fiber functionalized with polythymidilic acid icosanucleotide was selected at random from the batch of fibers (ca. 25) created in example 1 and was positioned under the objective of the microscope, as illustrated in FIG. 4(*a*). In this orientation the incident laser radiation entered the proximal terminus and was totally internally reflected throughout the fiber. The majority of the fiber was submerged in a hybridization buffer solution consisting of 1.0 M NaCl and 50 mM sodium phosphate (pH 7.4) in sterile water contained within a 4 ml plastic cuvette. Hybridization buffer was passed through an acrodisc® filter immediately prior to introduction to the cuvette. Emitted fluorescent radiation, from the stimulated fluorescent molecules associated with the double-stranded nucleic acids, was directed back towards the microscope by total internal reflection. The emission from the fluorescent molecules was separated from the excitation radiation by a dichroic mirror and directed to a photomultiplier tube. The photomultiplier tube provided measurements of the intensity of fluorescence emission. Fluorescence intensity values are reported with the system at 25° C. to avoid inconsistencies cause by the temperature dependence on fluorescence quantum efficiency and as relative quantities, thereby obviating the need to control experimental parameters such as laser intensity, optical alignment and photomultiplier tube (PMT) gain which are beyond accurate control from day to day.

In order to affect hybridization with the immobilized nucleic acid strands, $dA_{20}$ ssDNA was added to the plastic cuvette containing the suspended fiber in fresh hybridization buffer at a temperature of 85° C. This temperature was chosen as it is sufficiently greater than the 60° C. duplex melting temperature ($T_m$, the temperature at which half of all the duplexes present are dissociated) and is well below the boiling point of the buffer. Incubation at temperatures below $T_m$ has been shown to cause incomplete hybridization wherein only a fraction of the bases on each strand interact to form partially hybridized complexes (Rubin et al, 1989, Nucleic Acid and Monoclonal Antibody Probes, B. Swaminathan and G. Prakash, Eds., Marcel Dekker, Inc., NY, pp. 185–219). Though covalent immobilization of ssDNA removes one degree of freedom from the oligomer, hybridization at temperatures initially above the duplex $T_m$ ensures the formation of duplexes with the greatest possible extent of overlap. In all cases, no appreciable intensity change from that of the baseline was observed after the 90 minute incubation period. The solution was allowed to stand and cool to room temperature (25° C.) between 30 and 90 minutes after which the fiber was flushed with 60 ml of hybridization buffer (25° C.) to remove the excess strands.

Intercalation of the fluorophore into the dsDNA was achieved by injecting 10 μl of a 1 mg·ml$^{-1}$ aqueous solution of ethidium bromide (EB) into the cuvette and allowing the solution to stand for 15 minutes followed by washing the fiber by flushing the cuvette with 60 ml of fresh hybridization buffer (25° C.).

Figure 9A:
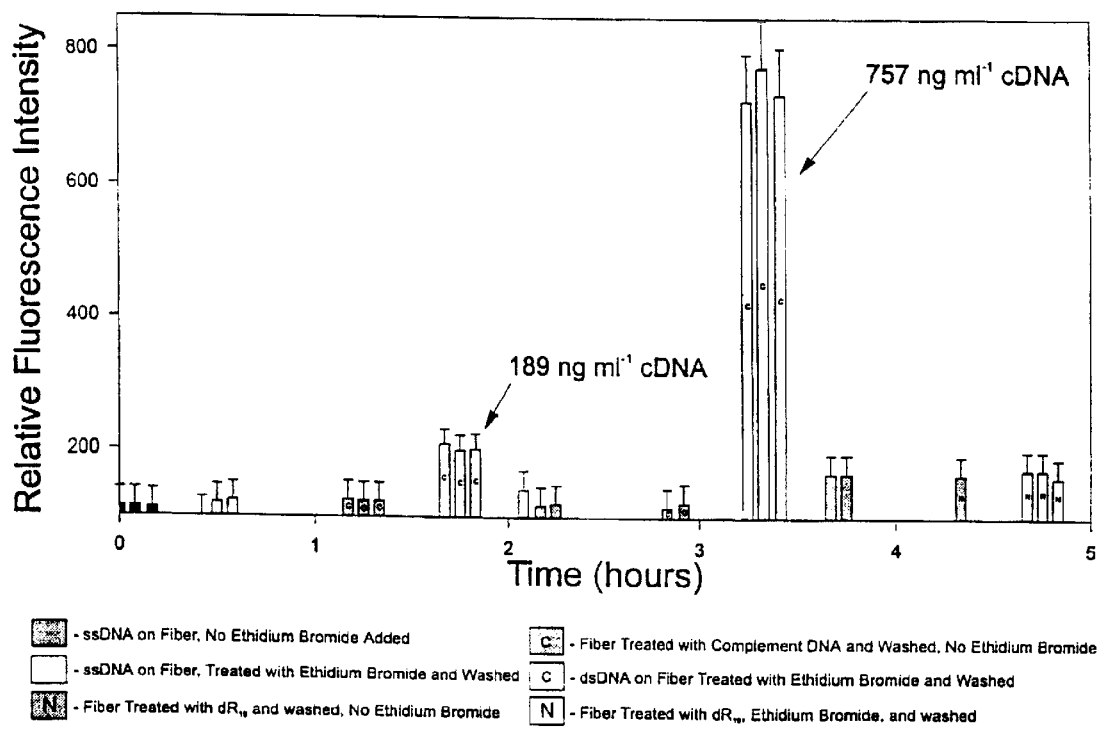
FIG. 9(a). Response characteristics of an optical biosensor to complement and non-complement DNA.
Figure 9B:
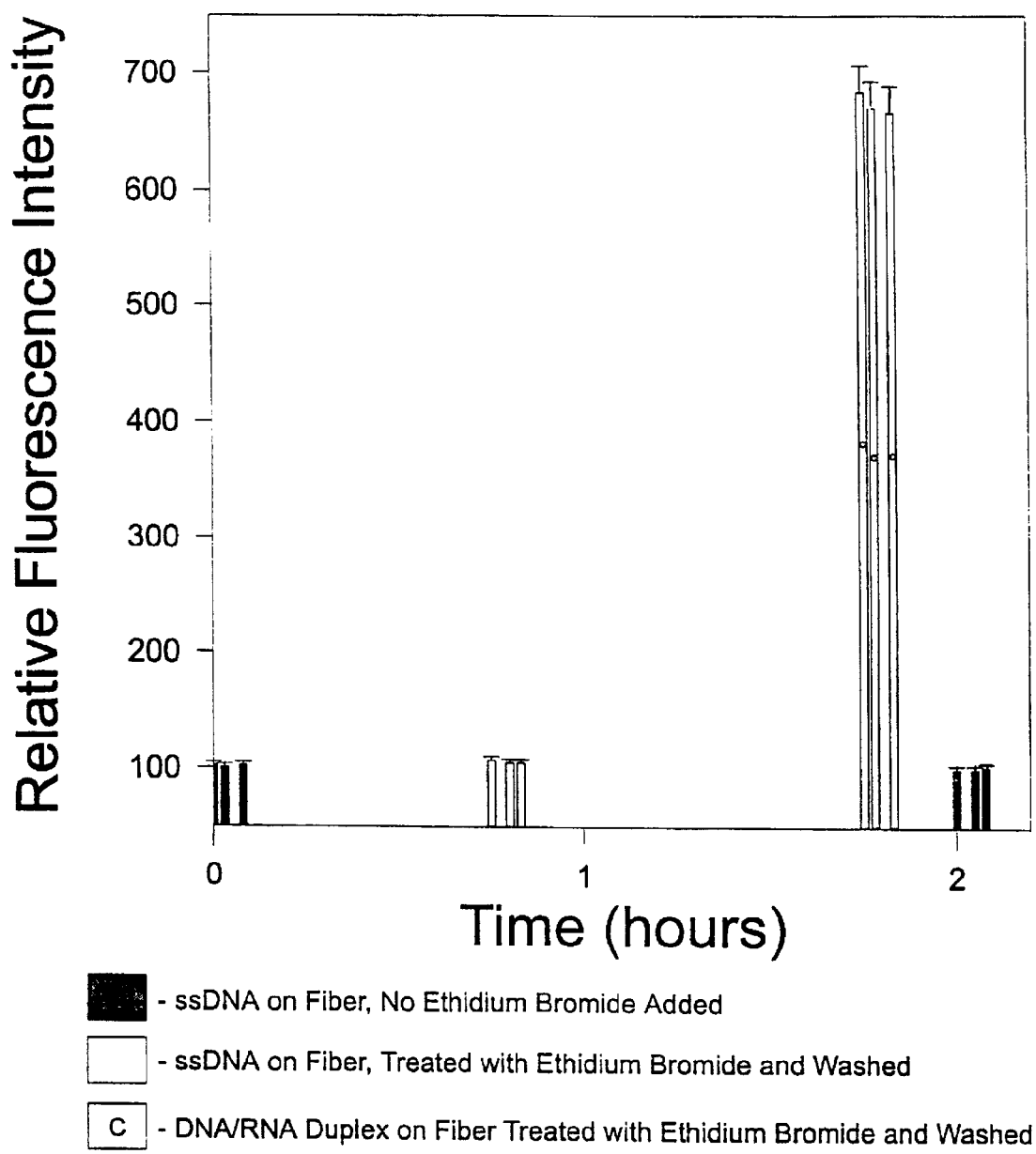
FIG. 9(b). Response characteristics of an optical biosensor to 570 ng·ml$^{-1}$ of complement RNA.

The response of the fiber optic DNA biosensor to EB and cDNA is shown in FIG. 9. As a control experiment, 10 μL of a 1 mg·ml$^{-1}$ aqueous solution of EB was added to the cuvette in which the fiber functionalized with ssDNA was suspended. After 15 minutes, 60 ml of fresh hybridization buffer (25° C.) was flushed through the cuvette in order to remove any non-specifically bound ethidium cation and no discernible increase in fluorescence intensity from the fiber was observed. A 104±15% increase in the fluorescence intensity was observed from the fiber which was exposed to 189 ng·ml$^{-1}$ of cDNA and stained with EB relative to the baseline value for the cleaned sensor with only ssDNA on the waveguide surface. The fiber was regenerated by flushing the cuvette and optical sensor 30 ml of hot (85° C.) buffer solution over a period of c.a. 30 seconds and the system allowed to stand for five minutes. After the five minute wait, an additional 30 ml of hot buffer was flushed through the cuvette to wash away the dissociated cDNA strands. This procedure is known to melt DNA duplexes as the buffer temperature was well above the $T_m$ of the dsDNA. The fluorescence intensity returned, within experimental uncertainty, to the initial intensity observed at the beginning of the experiment. The same hybridization experiment was repeated where the optical sensor was exposed to 757 ng·ml$^{-1}$ of cDNA during the hybridization procedure. This yielded an increase of 720±20% in the observed fluorescence intensity from the sensor with respect to the baseline value. In contrast, a similar concentration of non-complementary sequences (a nonadecamer of random base sequence) gave essentially no response, as shown in FIG. 9(*a*).

A 3.8 ng·μl$^{-1}$ solution of $rA_{20}$ (450 μl) was introduced into a cuvette containing hot hybridization buffer and the sensor to provide a 570 ng ml$^{-1}$ solution of cRNA. The same hybridization and staining procedure as used for cDNA was followed. The response profile for this hybridization procedure is shown in FIG. 9(*b*). A comparison of response of the biosensor with immobilized $dT_{20}$ to cDNA and cRNA agree to within experimental error.

Example 9

Effective of Ethidium Bromide (EB) Staining Time and Concentration

Figure 10:
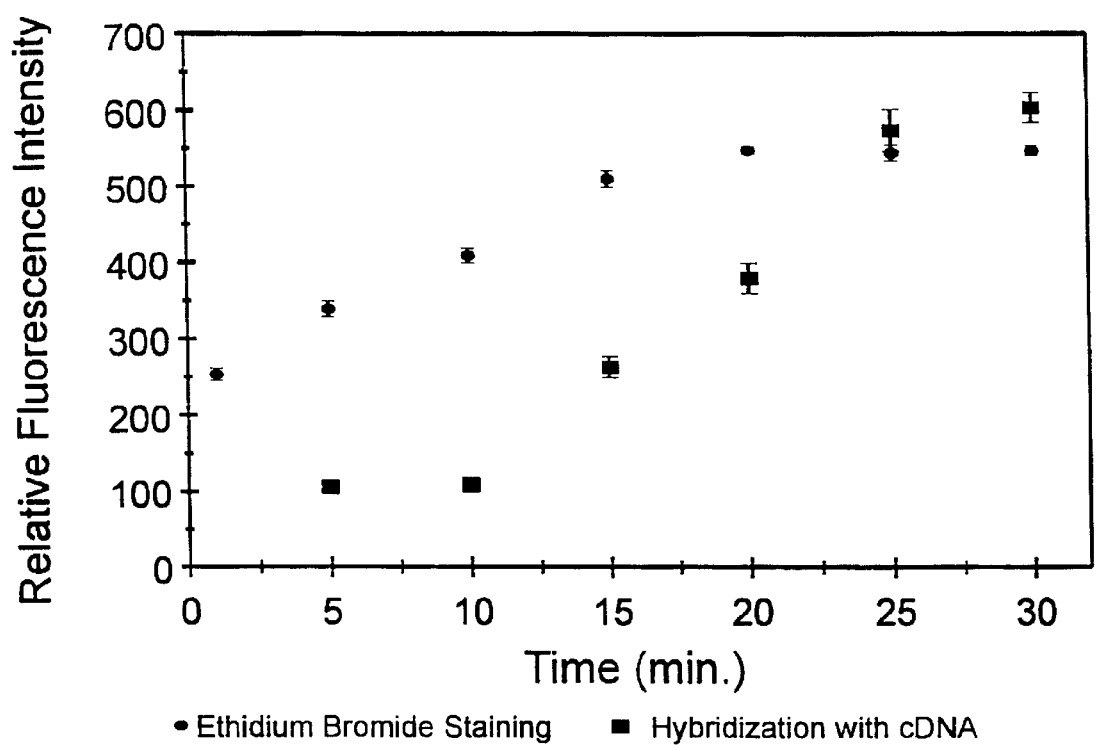
FIG. 10. Response time of the optical sensor constructed as per the protocols in examples 1 and 5 and effect of ethidium bromide incubation time.

The staining time of the sensor with EB, was changed after each hybridization with cDNA. For each determination, injections of 30 μl of 56.8 μg·ml$^{-1}$ solution of aqueous dA$_{20}$ were made and the hot hybridization buffer in the cuvette, which contained the cDNA strands, was allowed to cool to room temperature over a time of 30 minutes. A 1 mg·ml$^{-1}$ solution of EB in water (10 μl) was added to the cuvette after each hybridization to provide an EB concentration of 8.4–10$^{-3}$M. A staining time of 20 min. with 8.4×10$^{-3}$M EB was required to generate ≧99% of the full signal, as shown in FIG. 10(a).

To study the effect of EB concentration during dsDNA staining, all hybridization parameters were the same as those used to study staining time and a staining time of 20 min. was used. Staining with EB solutions of concentrations of 8.5×10$^{-3}$M or greater were required to generate ≧99% of the full staining in 20 min., as shown in FIG. 10(b).

Example 10

Long Term and Thermal Stability of the Nucleic Acid Sensor

Figure 11:
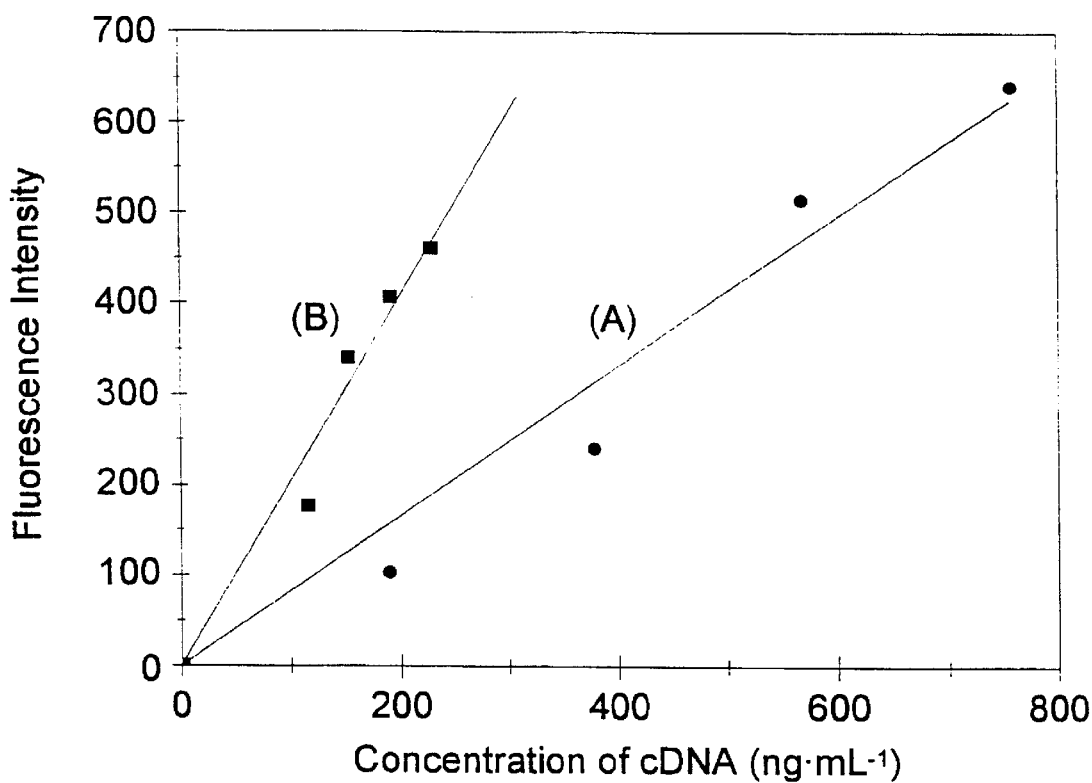
FIG. 11. Response of a DNA optical biosensor (a) after storage for one month used without cleaning and (b) after storage for eleven months and cleaned by sonication in ethanol for 10 minutes. Note: A 1-month-old sensor which had been cleaned by sonication (data not shown) provided a response similar to (b).

The robustness of the optical sensors, and DNA as a biorecognition element, was made evident by the maintenance of activity after long term storage and vigorous cleaning conditions. Fibers that were stored for over 1 year in vacuo, in 1:1 ethanol/water solutions, absolute ethanol, or dry at −20° C. provided identical response characteristics to freshly prepared fibers. Adsorbed fluorescent contaminants which were accumulated through long term storage were completely removed (as confirmed through fluorescence microscopy) by sonicating the fibers in a solution of 1:1 ethanol/water with full maintenance of activity and sensitivity. FIG. 11(a) shows the response of a 1 month old fiber (stored in vacuo) used with no cleaning of the surface and (b) an 11 month old fiber (stored dry at −20° C.) which had been cleaned by sonication in ethanol solution. It should be noted that the sensitivity of the cleaned 11 month old fiber is identical to that of 1 month old fibers cleaned by the same procedure (data not shown). Cleaning of the sensor by sonication prior to use has consistently been observed to increase the sensitivity of the device by a factor of c.a. 2.5. The sensors have provided femtomolar detection limits and a response which is linear with the concentration of cDNA (M.W.=6199 g·mol$^{-1}$). The regression lines shown in FIG. 11 show good fits to the data points with r$^2$ values of 0.965 and 0.968 for the 1 month and 11 month-old fibers, respectively. From this data, the sensitivity of the optical sensor (11 month-old, fabricated by the protocols of examples 1 and 5) was determined to be an increase in fluorescence intensity of 203% per 100 ng·ml$^{-1}$ of cDNA with a measured limit of detection of 86 ng·ml$^{-1}$. Maintenance of calibration has been observed for all experiments done thus far in which as many as 5 regenerations have been done over durations of up to 12 hours.

The ability to clean and sterilize a bioprobe or biosensor device so that it may be usable in an on-line configuration is a significant advantage. As the specific binding properties of nucleic acids are based on secondary structure, the use of nucleic acids in biosensor fabrication leads to devices which are not only stable to prolonged storage, but also to harsh washing conditions and sterilization. A summary of the effects of cleaning by sonication in absolute ethanol (15 minutes) and autoclaving (120° C. for 20 minutes at 4 atmospheres pressure in sterile water) on the response of the sensors to (~400 ng·mL$^{-1}$) is shown in the Table which follows. Both sonication in ethanol and autoclaving are observed to improve the response of the sensor, most likely through the removal of contaminants on the surface of the sensor (stored dry for 11 months, or stored in ethanol).

TABLE 1

Effect of storage conditions, cleaning, and sterilization on sensor response to 400 ng · ml$^{-1}$ cDNA.

| Storage Conditions | Cleaning/Sterilization Conditions | Relative Fluorescence Intensity Increase (%) |
| --- | --- | --- |
| 1:1 Ethanol/Water (25° C.) | — | 333 ± 20 |
| 95% Ethanol (25° C.) | — | 395 ± 20 |
| Dry (−20° C.) | — | 341 ± 20 |
| 1:1 Ethanol/Water (25° C.) | Autoclave | 430 ± 20 |
| 1:1 Ethanol/Water (25° C.) | Sonication | 453 ± 20 |

Example 11

Thermal Denaturation Studies of the cDNA: Immobilized DNA Complex on the Sensors Created from the Protocols of Examples 1 and 5 and Comparison to that of the Same Oligonucleotide Complex in Solution i) Thermal Denaturation Investigations of Aqueous dT$_{20}$ with Aqueous dA$_{20}$.

Equimolar amounts of each oligomer in hybridization buffer (1 M NaCl, 10 mM PO$_4$, pH=7.0) were mixed so that the final concentration was approximately 1 μM in each strand. Prior to thermal melt studies the oligonucleotide mixture was heated briefly to 80° C. and slowly cooled to 20° C. in order to hybridize all of the strands. The samples were held at the low temperature limit for 15 minutes prior to initiating melt studies, to allow for thermal equilibration. The temperature was then ramped at 0.5° C. intervals at a rate of 0.5° C./min. while the absorbance was recorded at 260 nm.

ii) Melt-Curve Investigations of Immobilized dT$_{20}$ with cDNA.

Sequences of dT$_{20}$ were immobilized onto planar fused silica wafers (5 mm ×10 mm×1 mm) according to the protocols in examples 1 and 5. The immobilized dT$_{20}$ was hybridized with complementary dA$_{20}$ sequences by immersing the wafer in a 56.8 ng·ml$^{-1}$ solution of dA$_{20}$ at 85° C. and allowing the immersed wafer to cool to room temperature (25° C.). The wafer was then removed from the cDNA solution and washed with room temperature hybridization buffer solution. The wafer was then suspended in a quartz cuvette that was placed in the temperature controlled cuvette housing of the UV-vis spectrometer. The placement of the wafer was adjusted so that it rested in the path of the light beam. The dead volume beneath the wafer was taken up by inert packing material. Absorption spectra were collected at approximately 2° C. increments of temperature in the range from 29° C. to 76° C. The temperature in the cuvette was set by programming an external circulating bath to a specific temperature and the temperature of the buffer solution surrounding the fused silica wafer was quantitatively measured using a silanized glass encapsulated thermistor. Measurements of absorption at each temperature were done by integrating 100 spectra in the wavelength range between 220 nm and 320 nm.

iii) Hypochromicity and Melt-Curve Thermodynamics.

The transition between an ordered duplex state and the disordered denatured state for systems of complementary nucleotides can be monitored and analyzed by UV-Visible absorbance spectroscopy to determine the duplex melting temperature (T$_m$). The extent of hybridization (i.e. the number of base pairs formed per duplex) was determined by a comparison of melt profiles for the immobilized oligonucleotides to similar reported values and $dA_{20}+dT_{20}$ in solution.

The fraction of single strands present in the system at any temperature ($f_{ss}(T)$) may be determined through the use of the following equation:

$$f_{ss}(T) = \frac{A(T) - A_{ds}(T)}{A_{ss}(T) - A_{ds}(T)}$$

where $A(T)$, $A_{ss}(T)$, and $A_{ds}(T)$ are the absorbances of the experimentally obtained melting curve, the upper baseline (single stranded oligomers), and the lower baseline (double stranded oligomers) respectively at temperature T (Nelson, J. W.; Martin, F. H.; Tinoco Jr., I. *Biopolymers* 1981, 20, 2509–2531.). By plotting $f_{ss}$ against temperature, the duplex melting temperature can be obtained by determining the temperature at which $f_{ss}=0.5$.

iv) Melt-Curve Studies of Support Bound Duplex DNA and Aqueous Phase DNA.

Figure 12:
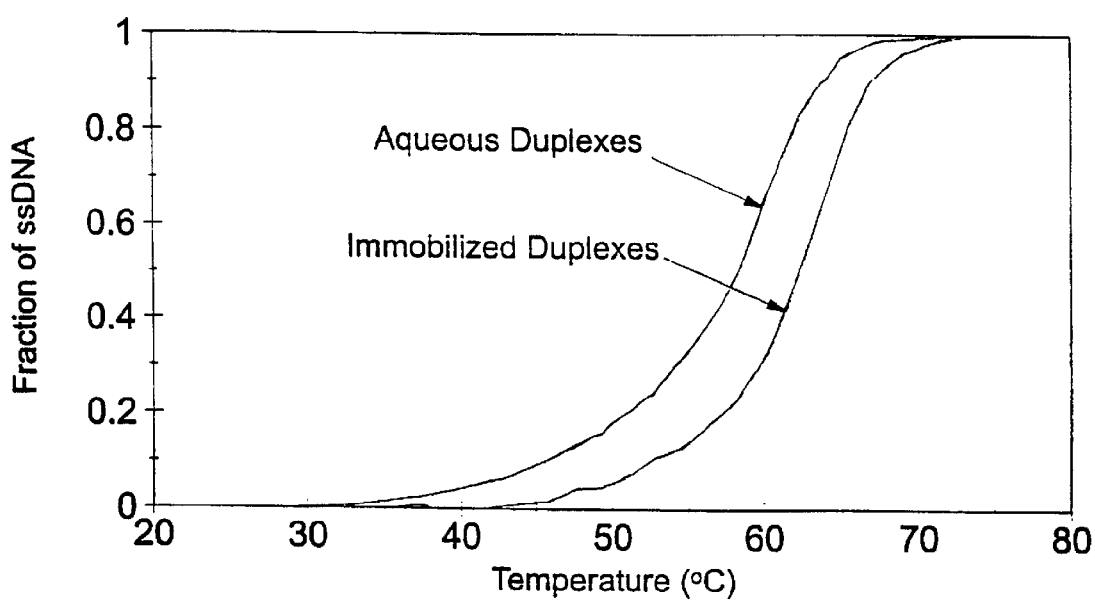
FIG. 12. Thermal denaturation profiles of aqueous $dA_2$+$dT_{20}$ and immobilized $dT_{20}$ with aqueous $dA_{20}$.

The purpose of the thermal denaturation studies was to examine whether linkage of an oligonucleotide to a solid support through a terminal nucleotide phosphate would cause the loss of degrees of freedom with respect to the availability of each nucleotide to partake in formation of the double stranded structure. Melt profiles for the thermal denaturation of dsDNA immobilized on the surface of a fused silica wafer and dsDNA in solution were obtained, and the results of these investigations are summarized in FIG. 12. The duplex melting temperature of the immobilized strands with aqueous phase complement strands was 62.4±0.3° C. The $T_m$ value for the aqueous phase $dA_{20}+dT_{20}$ duplex was determined to be 60.5° C. using the software supplied by Varian. Kibler-Herzog et. al. (Kibler-Herzog, L.; Zon, G.; Whittier, G.; Mizan, S.; Wilson, W. D. *Anti-Cancer Drug Design* 1993, 6, 65–79.) have reported the melting temperature of a $dA_{19}+dT_{19}$ duplex in 1.02 M NaCl to be 61.1° C. This suggests that for the immobilized oligomers investigated in this work, the extent of hybridization was complete with base pairing of 20 bases per strand. The small differences in the three $T_m$ values may be accounted for by the fact that each of these experiments was done on a different instrument at different times, and the salt concentration used in this work was slightly lower than that used by Kibler-Herzog et al. As the duplex stability in low ionic strength buffers is less than that in high ionic strength buffers, it would be expected that the melting temperature of the immobilized $dT_{20}+dA_{20}$ duplex would be higher in the buffer of lower stringency (Puglisi, J. D.; Tinoco Jr., I.; *Methods in Enzymology*, 1989, 180, 304–325.). In addition to this, a greater value of $T_m$ for the immobilized duplex over the aqueous phase duplexes should not be considered unusual as only one of the strands will experience a significant gain in entropy upon melting of the immobilized duplex. These factors lead to the conclusion that, within experimental uncertainty, the immobilized $dT_{20}+dA_{20}$ duplexes were more stable, if not as stable, as the aqueous phase $dA_{20}+dT_{20}$ and $dA_{19}+dT_{19}$ duplexes. This also suggests that no hindrance of duplex formation is observed with respect to the availability of the bases for hybridization. This result is in accord with the investigations of Wolf et al. (Wolf, S. F.; Haines, L.; Fisch, J.; Kremsky, J. N.; Dougherty, J. P.; Jacobs, K. *Nucleic Acids Research* 1987, 15, 2911–2926.), in which oligonucleotides bound to solid supports via a long chain aliphatic tether at the strand termini (3'-end) were not observed to be hindered with respect to hybridization efficiency Example 12

Detection of cDNA with and Optical Sensor functionalized with an Oligonucleotide Probe Sequence for *Candida albicans*

Figure 13:
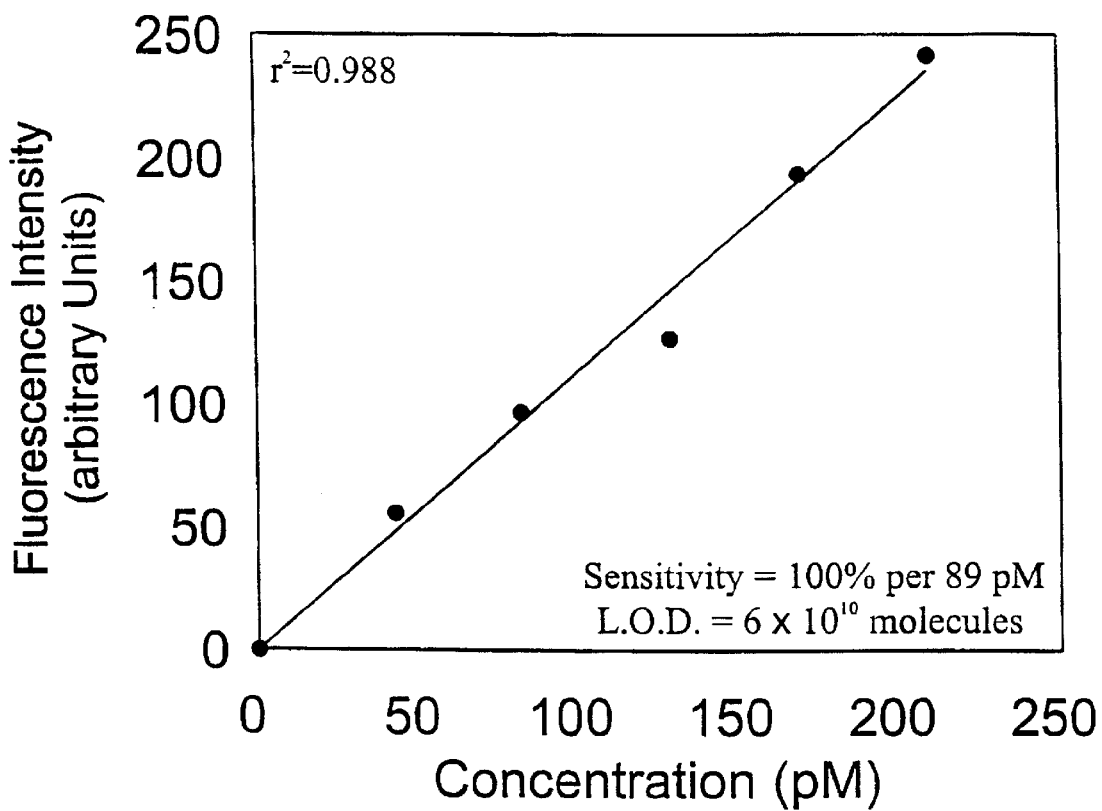
FIG. 13. Response of the optical sensor with immobilized nucleic acid probe for *Candida albicans* to complement DNA.

Optical Sensors were created by the protocols in examples 2 and 5 where the oligonucleotide sequence (5'-TAG GTG AGA CAT ATC ACA GA-3'SEQ ID NO: 1), which is a nucleic acid probe for the E03 forward sequence of the *Candida albicans* genome, was assembled onto the substrate linker functionalized fibers. Hybridization and staining protocols as reported in example 9 were followed. The response of the sensor to cDNA (20 nucleotides in length) is shown in FIG. 13. Linear calibration ($r^2=0.988$), good sensitivity (100% fluorescence intensity increase per 89 pM increase in concentration in the 4 ml of solution surrounding the optical sensor) and low detection limits ($6 \times 10^{10}$ molecules) were observed for the device.

Example 13

Fabrication of Optical Sensors with Immobilized Polythymidilic Acid Icosanucleotides Functionalized at the 5'-terminus with N5-Tethered 3,8-Diamino-6-phenylphenanthridium Cation i) Synthesis of Methyl-(12-hydroxy)dodecanoate.

12-hydroxydodecanoic acid (5 g) was dissolved in 100 ml of dry methanol to which was added a solution of p-toluenesulfonic acid (88 mg) in 5 ml of methanol dropwise over a 15 minute time-span. The solution was refluxed for 16 hours after which time the solvent was removed under reduced pressure. The product was then twice extracted into chloroform from a 5% aqueous solution of sodium bicarbonate. The organic phase was recovered, dried over $NaSO_4$, and the solvent removed under reduced pressure.

ii) Tosylation of Methyl-(12-hydroxy)dodecanoate

Methyl-(12-hydroxy)dodecanoate (1.6 g, 7 mmol) was placed in and oven dried flask cooled under anhydrous argon and treated with 3 ml of a solution of p-toluenesulfonyl chloride (1 eq., 7 mmol, 1.31 g) in dry pyridine. The solution was stirred at 25° C. under an inert atmosphere for 16 hours. The solvent was then removed under reduced pressure and the tosylated product was stored dry at −20° C. until needed.

iii) N-Alkylation of 3,6-dinitro-6-phenyl-phenanthridine with the Tosylate of Methyl-(12-hydroxy)dodecanoate.

3,8-Dinitro-6-phenyl-phenanthridine (3.5 mmol, 1.2 g) was combined with the tosylated methyl-(12-hydroxy) dodecanoate (7 mmol, 2.7 g) in dry nitrobenzene and the solution stirred for 6 hours at 160° C. under an argon atmosphere. The alkylated quaternary ammonium salt was precipitated from the mother liquor by addition of diethyl ether and collected by filtration. The product was further purified by silica gel column chromatography (25% methanol in chloroform) and recovered as a dark purple solid.

iv) Reduction of 3,8-dinitro-5-methyldodecanoate-6-phenyl-phenanthridium Chloride 3,8-Dinitro-5-methyldodecanoate-6-phenyl-phenanthridium chloride (1.3 mmol, 0.72 g) was dissolved in 10 ml of THF and stirred over $NiCl_2.6H_2O$ (10.68 g) and powdered Al (0.81 g). Water (0.3 ml) was then added to initiate the formation of the black Ni/Al catalyst and the reaction allowed to proceed for 15 minutes. The solution containing the reduced product was recovered by filtration, followed by removal of the solvent under reduced pressure. The product was purified by silica gel column chromatography (25% methanol in chloroform) and recovered as a dark purple solid (4%, 0.03 g).

v) Tritylation of 3,8-diamino-5-methyldodecanoate-6-phenyl-phenanthridium Chloride 3,8-diamino-5-methyidodecanoate-6-phenyl-phenanthridium Chloride (0.03 g, 62 μmol) was dissolved in dry pyridine and treated with dimethoxytrityl chloride (3 eq, 68 mg) suspended in dry pyridine (4 ml). The reaction was allowed to proceed for 16 hours at 25° C. with stirring under an inert atmosphere. The solvent was then removed under resuced pressure and the product purified (58%, 36 μmol) by reverse phase HPLC (isocratic elution with 1:1 methanol/water).

vi) Deprotection of the methyl-ester protecting group on 3,8-Bis(dimethoxytritylamino)-5-methyldodecanoate-6-phenyl-phenanthridium Chloride 3,8-Bis(dimethoxytritylamino)-5-methyldodecanoate-6-phenyl-phenanthridium chloride (36 μmol) was suspended in 80 ml of a solution of 1:3 water/methanol. The solution was degassed and treated with KOH (4 eq., 160 μmol) for 16 hours with stirring at 25° C. The reaction was quenched and the pH neutralized by treatment with HCl (1 eq, 15 μl of conc.).

vii) Synthesis of 5'-aminohexyl-dT$_{20}$ Functionalized Optical Sensors.

Figure 14:
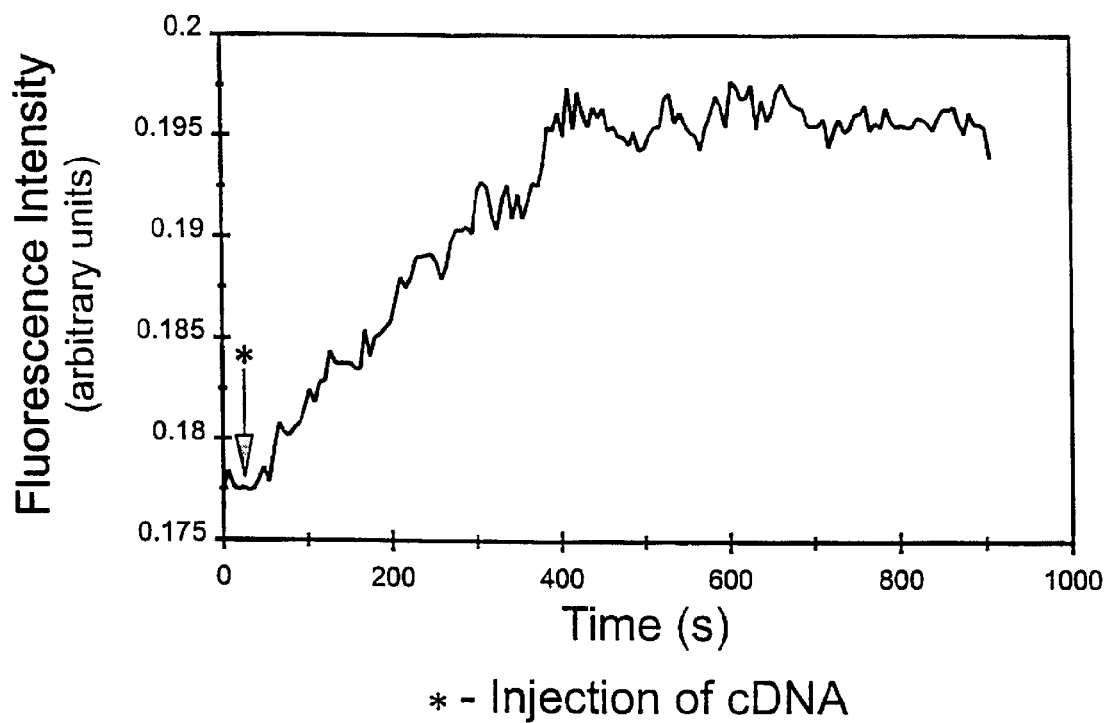
FIG. 14. Response of a reagentless biosensor as described in Example 14. The graph measures fluorescence from the tethered dye on the terminus of the immobilized nucleic acid as a function of time after exposure to a sample of 720 ng of cDNA.

DMT-HEG-GOPS functionalized optical fibers (prepared according to the method of Examples 2) were functionalized with polythymidilic acid icosanucleotide (according to the method of example 5) terminated an N-trifluoroacetamide protected aminohexyl moiety at the 5'-end by use of the commercially available Aminolink 2® phosphoramidite synthon from ABI. Deprotection of the phosphate blocking groups from the immobilized oligomers was achieved by standing the fibers in a solution of 2:3 (v/v) triethylamine/acetonitrile at room temperature for 1.5 hours. Removal of the trifluoroacetamide protecting group on the aminohexyl functionality located at the 5'-end of the immobilized strands was done by exposing the fibers to a $10^{-3}$ M solution of sodium borohydride in absolute ethanol for 1 hour at room temperature. The fibers were then washed once in a solution of $10^{-1}$ M HCl followed by washing with copious amounts of sterile water.

viii) Attachment of the Trityl-Protected Tethered Ethidium Analogue to the Aminohexyl Functionalized Optical Fibers:

The fully deprotected fused silica optical fibers functionalized with 5'-aminohexyl polythymidilic acid icosanucleotides were immersed in a solution containing 5 mg of the DMT-protected tethered ethidium analogue, 40 μl of 1-methylimidazole, and 1.91 g of 1-ethyl-3-(3-dimethylaminopropyl)carbodiimide in 50 ml of water. After a 7 day incubation period at room temperature, the fibers were washed five times each with 50 ml portions of water, ethanol, and dichloromethane, respectively. The proportion dye-functionalized oligonucleotides was determined by measurement of the amount of dimethoxytrityl released from each detritylation step during automated synthesis and that from the deprotection procedure used to restore the primary amine moieties on the dye. From these assays it was determined that 63% of the immobilized oligonucleotides were functionalized with tethered dye.

ix) Characterization of the Fluorescence Response of the Reagentless Sensors with Tethered Fluorophore:

The response of the reagentless sensor to 720 ng of complement DNA is shown in FIG. 14. Hybridization was done at 40° C. in a buffer consisting of 1 M NaCl and 50 mM phosphate (pH 7.0). It should be noted that this sensor has a significantly improved response time over the sensors without tethered dye. 99% of the full analytical signal was reached in c.a. 6 minutes after injection of the complementary strands for the reagentless system while 45 minutes was required for full signal generation by the sensors without tethered dye (see FIG. 10{a}).

Example 14

Detection of TAT Triple-Helical DNA Using a Fiber Optic Biosensor i) Background

One important avenue not yet explored by the fiber-optic nucleic acid biosensor community is the investigation of triple-stranded oligonucleotide formation. Typically, a number of spectroscopic techniques (CD, NMR, UV and fluorescence spectroscopy) in addition to gel mobility shift assays need to be implemented in order to study the formation of triple-helical nucleic acids. However, each of these methods have problems in terms of either the amount of material that is required for analysis (NMR, CD, and gel mobility assays), or that they are limited to investigations of only certain triplex systems (e.g. only TAT triplexes can be monitored by UV absorption spectroscopy at 284 nm).

Various groups have developed methods for triplex detection ({i} Geselowitx, D. A.; Neumann, R. D. *Bioconjugate Chem.*, 1995, 6, 502. {ii} Bates, P. J., Dosanjh, H. S.; Kumar, S.; Jenkins, T. C.; Laughton, C. A.; Neidle, S. *Nucleic Acids Res.*, 1995, 23, 3627.). The use of nucleic acid binding ligands to identify DNA structures and morphology is one such method. Many ligands are known to interact in a noncovalent manner with the target oligonucleotide. Binding modes can be characterized as: (i) intercalation of the ligand, in which typically a planar aromatic moiety slides between the DNA bases—stabilized by π-π stacking and dipole interactions, or (ii) minor or major groove interaction which is stabilized by hydrogen bonding, hydrophobic and/or electrostatic interactions (Long, E. C.; Barton, J. K. Acc. *Chem. Res.* 1990, 23, 273.). Ethidium bromide binds to both duplexes and triplexes via an intercalative mode (Waring, M. J. *Biochim. Biophys. Acta*, 1966, 114, 234.), and this has been studied extensively by fluorescence methods. The fluorescence quantum efficiency of the ethidium cation increases when intercalated into duplexes (LePecq, J. B.; Paoletti, C. *J. Mol. Biol.*, 1967, 27, 87.) and triplexes (Mergny, J. L.; Collier, D.; Rougée, M.; Montenay-Garestier, T.; Hélèn, C. *Nucleic Acids Research*, 1991, 19, 1521. , Scaria, P. V.; Shafer, R. H. *J. Biol. Chem*, 1991, 266, 5417), however, it has been shown that there is a marked difference in the binding efficiency and hence fluorescence intensity between the two types of complexes. LePecq and Paoletti were the first to observe that the fluorescence enhancement of ethidium during interaction with the duplex (poly rA)·(poly rU) was significantly greater than for binding to the triplex (poly rA)·(poly rU)$_2$ (LePecq, J. B.; Paoletti, C. C. R. *Acad. Sc. Paris* 1965, 260, 7033). More recent studies have confirmed that the fluorescence intensity of intercalated ethidium bromide is greater for duplexes than triplexes of ribonucleic acid, and that a temperature dependence exists for deoxyribonucleic acids (Mergny, J. L.; Collier, D.; Rougée, M.; Montenay-Garestier, T.; Hélène, C. *Nucleic Acids Res.*, 1991, 19, 1521., Scaria, P. V.; Shafer, R. H. *J. Biol. Chem.*, 1991, 266, 5417., Fang, Y.; Bai, C. L.; Zhang, P. C.; Cao, E. H.; Tang, Y. Q. *Science In China* (Ser. B), 1994, 37, 1306.). The results of molecular modeling studies suggest that a reduced binding affinity of ethidium for triplexes (relative to duplexes) exists due to the energetic cost of destacking base triplets as compared to successive base pairs (Sun, J. S.; Lavery, R.; Chomilier, J.; Zakrzewska, K.; Montenay-Garestier, T.; Hélène, C. *J. Biomol. Struct. Dynam.*, 1991, 9, 425.). This is partially offset by the quantum efficiency of ethidium bromide in triplex DNA which is greater than that for duplex DNA. Short homopolymeric T*AT triplexes have been the subject of seminal fluorescence studies. Letsinger et al. (Salunkhe, M., Wu, T. & Letsinger, R. L. (1992) *J. Am. Chem. Soc.* 114, 8768–8772.) have shown that for parallel T*AT triplexes, the fluorescence intensity of ethidium cation decreases dramatically in comparison to fluorescence intensity of the ligand bound to AT duplexes. Independent confirmation of decreased fluorescence intensity for ethidium bound to parallel T*AT triplexes (2xdT$_{10}$:dA$_{10}$) relative to duplexes (dT$_{10}$:dA$_{10}$) has appeared (Fang, Y.; Bai, C. L.; Zhang, P. C.; Cao, E. H.; Tang, Y. Q. *Science In China (Ser. B)*, 1994, 37,1306.).

We chose to investigate both parallel and antiparallel TAT triplexes as these sequences have been well documented in the literature (Plum, G. E.; Pilch, D. S.; Singleton, S. F.; Breslauer, K. *J. Annu. Rev. Biophys. Biomol. Struct.* 1995, 24, 319, and references therein). Branched nucleic acids as described by Damha et al. (Hudson, R. H. E.; Damha, M. *J. Nucleic Acids Res. Symp. Ser.* 1993, 29, 97., R. Hudson, A. Uddin, and M. Damha *J. Am. Chem. Soc.*, 1995, 117, 12470.) were used in this study as the unique architecture of bNAs has been utilized to stabilize reversed-Hoogsteen and Hoogsteen TAT triplexes. Investigations were also done to determine the best oligonucleotide orientation on the support for the detection of TAT triplexes. The motivation behind this research endeavor was then to create a rapid, reliable, reproducible assay for the detection of triple-helical nucleic acid formation. The development of a triple-helical assay, is an extension of work initiated for the detection of nucleic hybridization (Watson-Crick motif using fiber optic total internal reflection fluorecence (TIRF) sensors functionalized with single-stranded deoxyribonucleic acid (ssDNA) probes.

ii) Synthesis of Oligonucleotides on Optical Fibers.

Optical fibers were activated by protocols given in example 2 and polyadenilic decanucleotides were assembled onto the substrate linker molecules on the fiber surface as per the methods given in example 5. Two batches of fiber were created, the first using commercially available N$^6$-phenoxyacetyl-5'-O-DMT-2'deoxyadenosine-3'-O-[(β-cyanoethyl) N, N-diisopropyl]phosphoramidite from Millipore Inc. to assemble decanucleotides with the 5'-terminus oriented away from the fiber surface. N$^6$-phenoxyacetyl-3'-O-DMT-2'deoxyadenosine-5'-O-[(β-cyanoethyl)N,N-diisopropyl]phosphoramidite was prepared via standard protocols and used to grow oligonucleotide on the functionalized fibers in a reversed (fiber→substrate linker→5'-dA10-3') orientation.

iii) Synthesis of Branched Oligonucleotides.

The "V" branched sequence 1 (FIG. 15) was synthesized on an Applied Biosystems 381A instrument using a 1 μmol scale synthesis cycle and β-cyanoethylphosphoramidite chemistry. Purification, desalting, and analysis of the branched oligonucleotide 1 by polyacrylamide gel electrophoresis was accomplished by our detailed protocols (Damha, M. J., Ganeshan, K., Hudson, R. H. E., Zabarylo, S. V., (1992) *Nucleic Acids Res* 20, 6565–6573; Damha, M. J.; Ogilvie, K. K. In *Methods in Molecular Biology, Vol. 20: Protocols for Oligonucleotides and Analogs*; Agrawal, S., Ed.; Humana Press, Inc.: Totowa, N.J., 1993, pp 81–114). Typical yields of this branched oligomer were 5–15 A$_{260}$ units (15–25%). The complement dA$_{10}$ for thermal denaturation studies was obtained from Dalton Laboratories (Toronto, Canada).

iv) Thermal Denaturation Profiles.

Absorbance versus temperature profiles of the nucleic acid complexes were measured at 260 nm using a Varian Cary I UV-VIS spectrophotometer equipped with a variable temperature cell holder controlled by an external variable temperature circulating bath. Data were collected with the spectrophotometer set on dual beam optical mode to reduce optical drift. The data were collected at 260 nm at 0.5 ° C. intervals with an equilibration time of 60s for each measurement point. Absorption coefficients of the branched molecules were assumed to be similar to their corresponding linear sequences and were calculated from those of mononucleotides and dinucleotides according to the nearest-neighbor approximation (Puglisi, J. D.; Tinoco, I., Jr. In *Methods in Enzymology*; Dahlberg, J. E., Abelson, J. N., Eds.; Academic Press, Inc.: San Diego, 1989; Vol. 180, 304.). Samples for thermal denaturation analysis were prepared by mixing the pyrimidine containing strand with the target (2 mM), lyophilizing the solution to dryness, and dissolving the oligomers in 10 mM Tris, 50 mM MgCl$_2$, pH 7.3 adjusted with HCl. The mixtures were then transferred to Hellma QS-1.000-104 cells. Oligonucleotide solutions were heated to 80° C. for 15 min and then slowly cooled to room temperature prior to melting experiments. Normalized plots were constructed according to the method of Kibler-Herzog et al. (Kibler-Herzog, L.; Zon, G.; Whittierm, G.; Shaikh, M.; Wilson, W. D. *Anti-Cancer Drug Des.* 1993, 8, 65.) based on $\{(A_t-A_o)/(A_f-A_o)\}$: where $A_o$ is the initial absorbance, $A_f$ is the final absorbance and $A_t$ is the absorbance at any temperature. All complexes showed sharp melting transitions. The melting temperature ($T_m$) was determined from the first derivative of each thermal curve. A precision in $T_m$ values, determined from variance in repeated experiments, of ñ0.5° C. or better was obtained for all of the denaturation profiles investigated.

v) Instrument Setup and Fluorescent Measurements

Figure 4C:
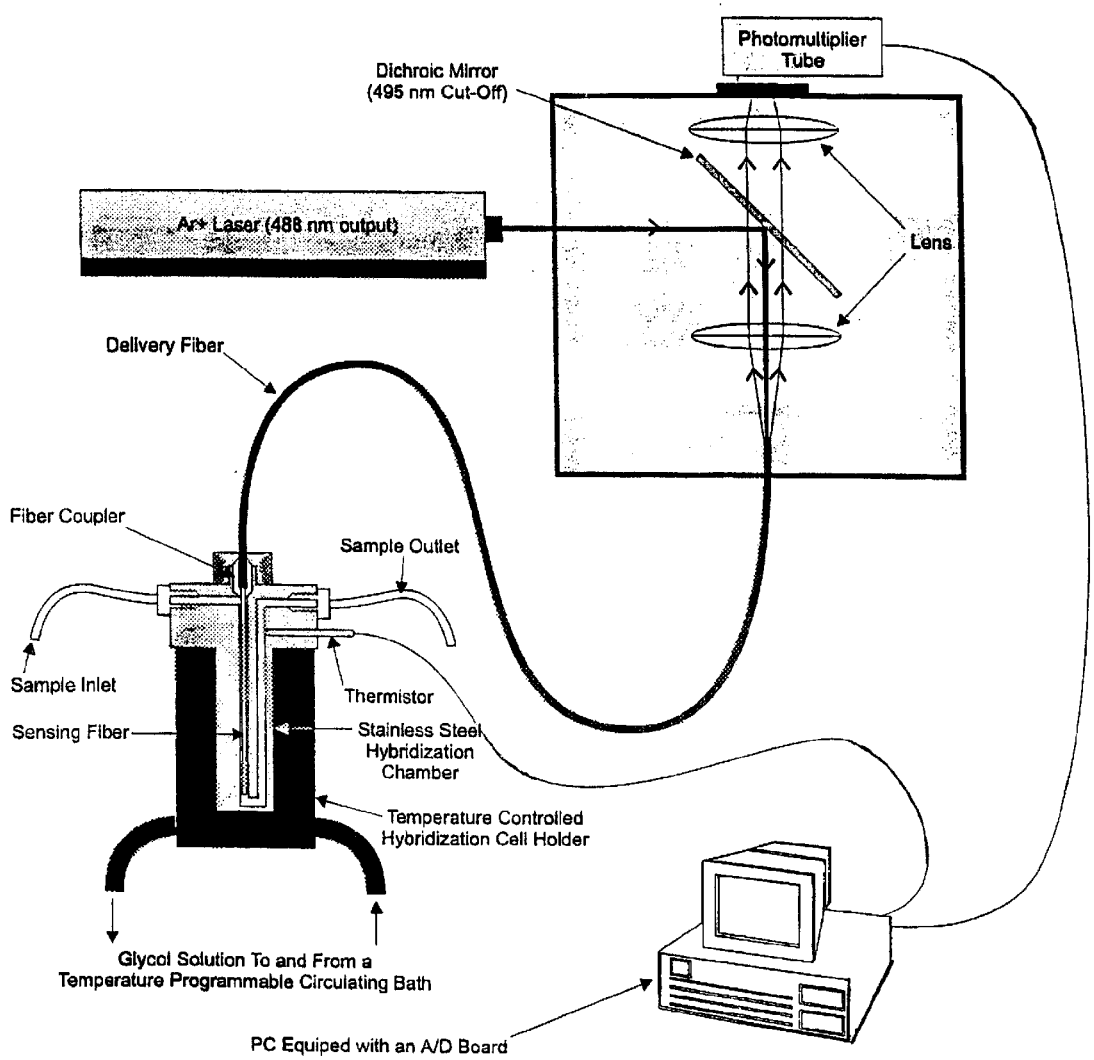

The laser radiation exiting the immersion lens of the fluorescence microscope (as described in Example 9) was coupled into a delivery fiber of similar numerical aperture (0.48) aligned beneath the objective, as illustrated in FIG. 4(c). The light was totally internally reflected along the delivery fiber to a sensing fiber functionalized with immobilized oligonucleotide. Coupling of the radiation between fibers was achieved by abutting the distal terminus of the delivery fiber to the proximal terminus of the sensing fiber. A loss in optical transmission of no greater than 2% was observed for the coupled system. The termini of the teflon fiber coupler were designed as compression-fit ends which provided a solution-tight seal that prevented contaminants from diffusing into the fiber coupler and causing drift in the analytical signal. The sensing fiber was placed in a small volume, stop-flow, stainless steel hybridization chamber (1.5 mm i.d.×48 mm) which provided a solution volume of 79 μl exposed to the sensing fiber. The temperature of the hybridization cell was controlled by placing the cell in a thermostated housing in which glycol solutions from external variable temperature circulating baths were made to flow. The temperature of the solutions in the hybridization cell were accurately determined (±0.2° C.) by use of a glass encapsulated thermistor incorporated into the hybridization cell and in contact with the solution at the exit of the hybridization chamber. Solutions containing hybridization buffer, ethidium bromide, and complementary nucleic acid sequences were delivered to the hybridization cell and sensing fiber by use of a peristaltic pump. Fluorescence emission from ethidium bromide that was intercalated into immobilized nucleic acid complexes was totally internally reflected within the sensing fiber. The portion of the light coupled back into the delivery fiber was directed towards the microscope objective where it was collimated and directed to the dichroic mirror. The fluorescence radiation was of longer wavelength ($\lambda_{max}$=595 nm) than the dichroic cut-off, and was transmitted through the mirror and directed towards a photomultiplier tube, where the fluorescence intensity could be quantitatively measured. Drift caused by variations in the efficiency of optical coupling, laser intensity and photomultiplier gain were obviated by normalization of all signals to that of a standard solution of ethidium bromide at 25° C. prior to and at the completion of each analysis.

vi) PAGE Mobility Retardation Assay.

The solutions of oligonucleotides were lyophilized to dryness, incubated in 10 μL of 30% sucrose with 50 mM MgCl$_2$ at 75° C. for 15 min., and then cooled to room temperature slowly. After a 4 day incubation at 4° C., the samples were loaded onto the gel. The running buffer contained 90 mM tris-borate buffer (pH 8.0). The non-denaturing 15% polyacrylamide gels contained 90 mM tris-borate (pH 8.0) and 50 mM MgCl$_2$. The native gels were run at 12.5 mA for 12 h. Following electrophoresis, the gels were covered with Saran Wraps and photographed with a Polaroid MP4 Land Camera over a fluorescent TLC plate (Merck, distributed by EM Science, Gibbstown, N.J.) illuminated by a UV lamp (Mineralight lamp, Model UVG-54, San Gabriel, Calif.). Instant Sheet Film (#52, medium contrast, ISO 400/21° C.) was used and the exposure (f4.5, 1.5s) made through a Kodak Wratten gelatin filter (#58). The gels were subsequently stained for 5 min in a 5 μg/ml solution of ethidium bromide and destained in distilled water for 30s. The gels were then covered with Saran Wrap®, illuminated by a UV lamp and photographed (f4.5, 2s) through a Hoya orange filter over a white background.

vii) Parallel and Antiparallel TAT Triplex Considerations.

In the formation of the intermolecular triplex 2×dT$_{10}$/dA$_{10}$ triplex, the third dT$_{10}$ strand interacts by means of Hoogsteen hydrogen bonds with the dA$_{10}$ strand in target Watson-Crick duplex, and is oriented parallel to it. In melting experiments (Mg$^{+2}$ buffer), the triplex 2×dT$_{10}$/dA$_{10}$ has two clearly resolved transitions, one for dissociation of the third strand from the duplex, i.e., dT$_{10}$*dA$_{10}$/dT$_{10}$→dT$_{10}$+dA$_{10}$/dT$_{10}$ (T$_m$ 18° C.), and one for dissociation of the duplex into its component strands, i.e., dA$_{10}$/dT$_{10}$→dA$_{10}$+dT$_{10}$ (T$_m$ 32° C.). Thus for this complex, association of the third (dT$_{10}$) strand with the duplex (dA$_{10}$/dT$_{10}$) is thermodynamically weaker than duplex formation itself.

Figure 15:
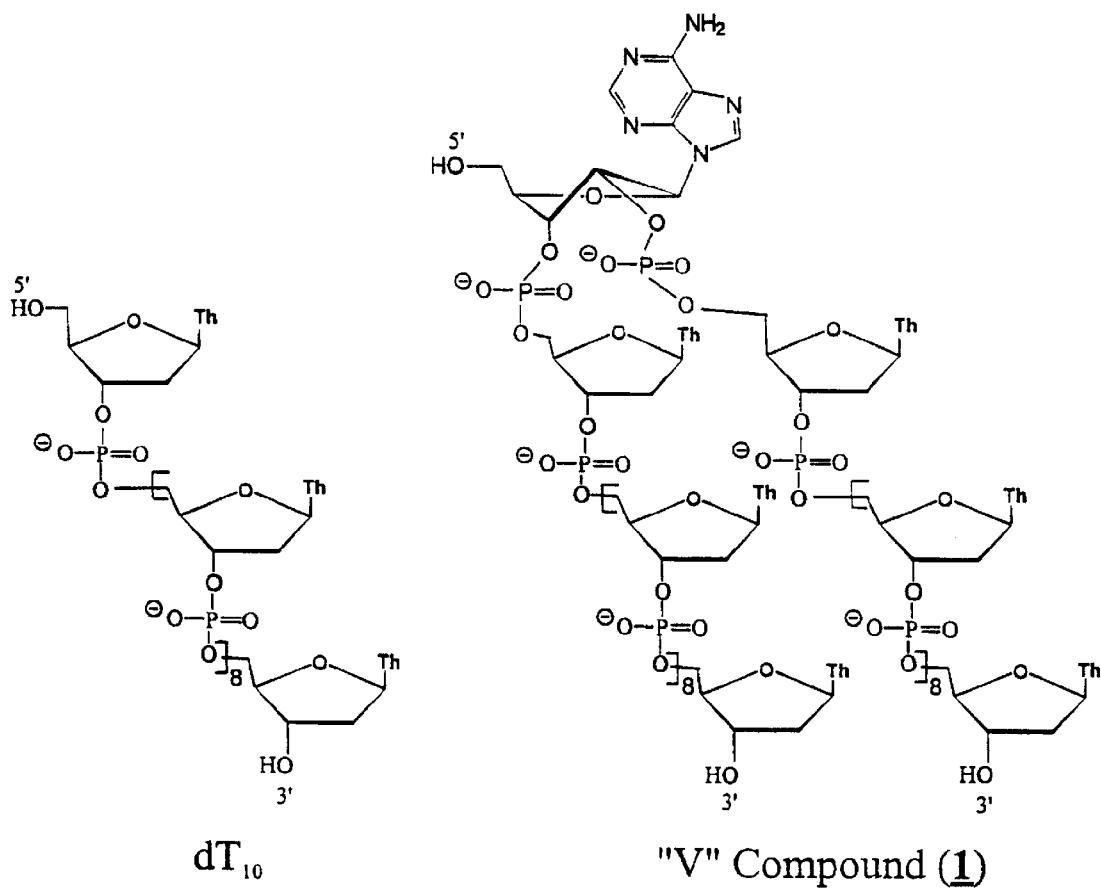
FIG. 15. The structures of $dT_{10}$ and compound 1, a branched oligonucleotide with identical oligo(thymidine) chains linked to the 2'- and 3'-positions of a ribose branch-point nucleoside i.e., $rA_{3' \to 5'\text{-}dT10}{}^{2' \to 5'\text{-}dT10}$ binds to $dA_{10}$ to yield a triple-stranded complex containing only T•AT (reverse Hoogsteen·Watson/Crick) base triplets.

Branched oligonucleotides are useful probes for stabilizing triplex DNA (R. Hudson, A. Uddin, and M. Damha *J. Am. Chem. Soc.*, 1995, 117, 12470.). The branched oligomer 1 (FIG. 15) for instance, binds to dA$_{10}$ to give a novel TAT triple-stranded complex in which both dT$_{10}$ strands are antiparallel to the purine (dA$_{10}$) strand. Although this motif had been observed for TAT bases in complexes dominated by pur·pur/py bonding (e.g. G·GC, A·AT) ({i} Moser, H. E.; Dervan, P. B. *Science*, 1987, 238, 645. {ii} Strobel, S. A.; Doucettestamm, L. A.; Riba, L.; Housman, D. E.; Dervan, P. B. *Science*, 1991, 254, 1639 {iii} Hoogsteen, K. *Acta Crystallogr*. 1959, 12, 822–823; (b) Felsenfeld, G.; Davies, D. R.; Rich, A. *J. Am. Chem. Soc.* 1957, 79, 2023–2024; {iv} R. Hudson, A. Uddin, and M. Damha *J. Am. Chem. Soc.*, 1995, 117, 12470.), it had not been observed previously for dT$_n$/dA$_n$ complexes. The formation of this triplex was induced by linkage of two dT$_{10}$ strands through their 5' ends via coupling to riboadenosine at the neighboring 2' and 3' oxygen atoms (FIG. 15). This arrangement causes the initial direction of the two dT$_{10}$ strands to be parallel, and forces the formation of a triplex in which the third dT$_{10}$ strand runs antiparallel to the dA$_{10}$ strand, and is bound to it via reversed-Hoogsteen interactions. Thermal denaturation profiles of a mixture of 1 and dA$_{10}$ (1:1) in Mg$^{+2}$ buffer, show a single transition from bound to unbound complex, consistent with its formation involving one rather than two bimolecular reaction steps, i.e., 1+dA$_{10}$→triplex 1/dA$_{10}$) (T$_m$ 35° C.).

viii) Triplex Studies Using Derivatized Optical Fibers with Normal (Fiber-3'-dA$_{10}$-5') Oligonucleotide Orientation.

Figure 16A:
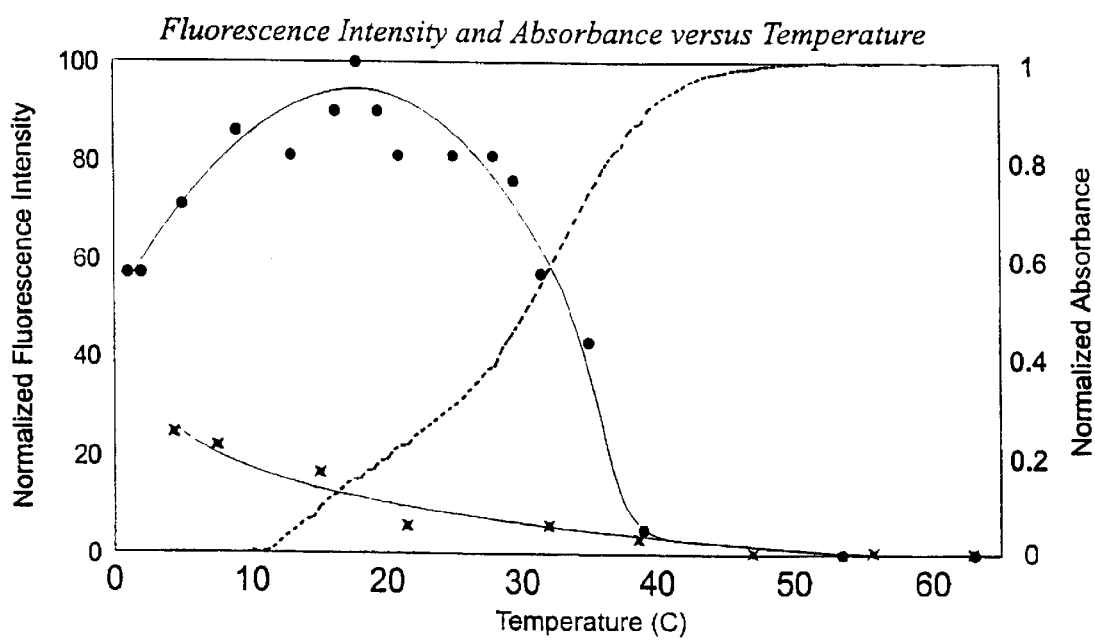
FIG. 16(a). Response (•) of the optical sensor with a 5'-end terminated recognition sequence to 40 pmol of linear $dT_{10}$ in the presence of $2.5 \times 10^{-8}$ M ethidium bromide. Response (X) of the optical sensor to $2.5 \times 10^{-8}$ M ethidium bromide and no $dT_{10}$. ··· Melting profile of the same nucleic acid system in bulk solution by measurement of absorbance (260 nm) in 10 mM TRIS and 50 mM $MgCl_2$ at pH 7.3.

Characterization of the triple-helical complexes via thermal denaturation studies were done. The dA$_{10}$ was grown in the conventional 3'-to-5' direction from the fiber surface. Solutions of ethidium bromide, ethidium bromide with dT$_{10}$, or ethidium bromide with 1, were heated in the hybridization chamber containing the decaadenylic acid functionalized optical fibers. Upon slow cooling, fluorescent measurements were taken at various temperatures. FIG. 16(a), illustrates that as the dT$_{10}$:dA$_{10}$ duplex was formed by lowering the temperature, there was an increase in the fluorescence intensity corresponding to ethidium bromide intercalation and quantum yield enhancement of the ligand in this complex. After further lowering of the temperature, we observed a decrease in the fluorescence intensity with decreasing temperature, indicative of exclusion of the ligand as a result of triplex formation (2×dT$_{10}$:dA$_{10}$). This process is illustrated in FIG. 7(a). In order to verify that triplex formation was alone responsible for the exclusion of the ethidium cation and hence the decrease in fluorescence intensity from the fiber, a control experiment was done using optical fibers functionalized with a twenty-nucleotide probe sequence of mixed base composition incapable of forming triplex structures. The hybridization experiment was done using the same methodology as for the decaadenylic acid functionalized fibers with the exception of the hybridization buffer (1M NaCl, 50 mM PO$_4$, pH 7.0). Having this nucleic acid sequence and buffer composition, only double-stranded complexes could form between the immobilized probe sequence and the complementary sequence. As can be seen in FIG. 6, a fluorescence intensity with a negative temperature coefficient was observed for the duplex system over the temperature range studied. The denaturation temperature for this system of nucleic acids and hybridization buffer was determined to be 73° C. by UV-visible thermal denaturation studies. Only double-stranded complexes existed over the temperature range investigated, as indicated by the enhanced fluorescence intensity for the experiment using the ethidium bromide and complementary oligonucleotide. The control experiment with ethidium bromide and no complementary oligonucleotide showed no such dramatic increase in intensity.

Upon exposure of the optical sensor to the reversed-Hoogsteen forming 1, no significant increase in fluorescence intensity over that of the ethidium bromide alone in solution was observed. The geometrical constraints of compound 1 are such that, if a complex is formed with the immobilized dA$_{10}$ strand in this particular (fiber-3'→5') orientation, the branch-point riboadenosine should be oriented toward the fiber surface thus presenting a steric barrier to triplex formation. In order to test whether steric interference surrounding the branch-point prevented triple-helical formation, an optical fiber having a dA$_{10}$ strand in the opposite orientation from the surface (i.e. fiber-5'→3') was synthesized.

ix) Triplex Studies Using Derivatized Optical Fibers with Reversed (Fiber-5'-dA$_{10}$-3') Oligonucleotide Orientation.

Figure 16B:
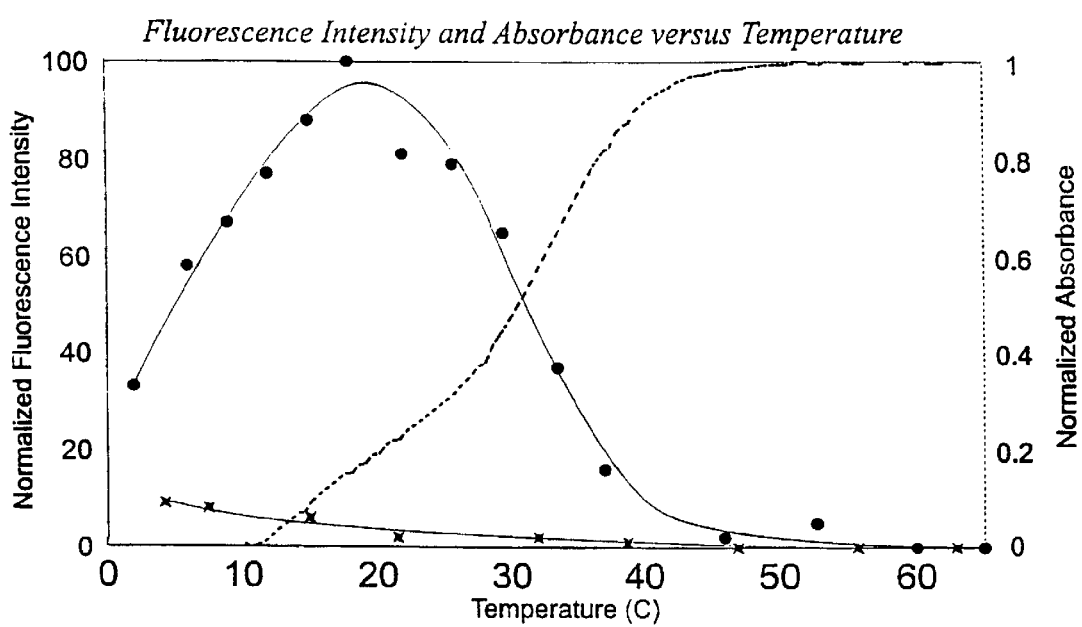
FIG. 16(b). Response (•) of the optical sensor with a 3'-end terminated recognition sequence to 40 pmol of linear $dT_{10}$ in the presence of $2.5 \times 10^{-8}$ M ethidium bromide. Response (X) of the optical sensor to $2.5 \times 10^{-8}$ M ethidium bromide and no $dT_{10}$. ··· Melting profile of the same nucleic acid system in bulk solution by measurement of absorbance (260 nm) in 10 mM TRIS and 50 mM $MgCl_2$ at pH 7.3.
Figure 16C:
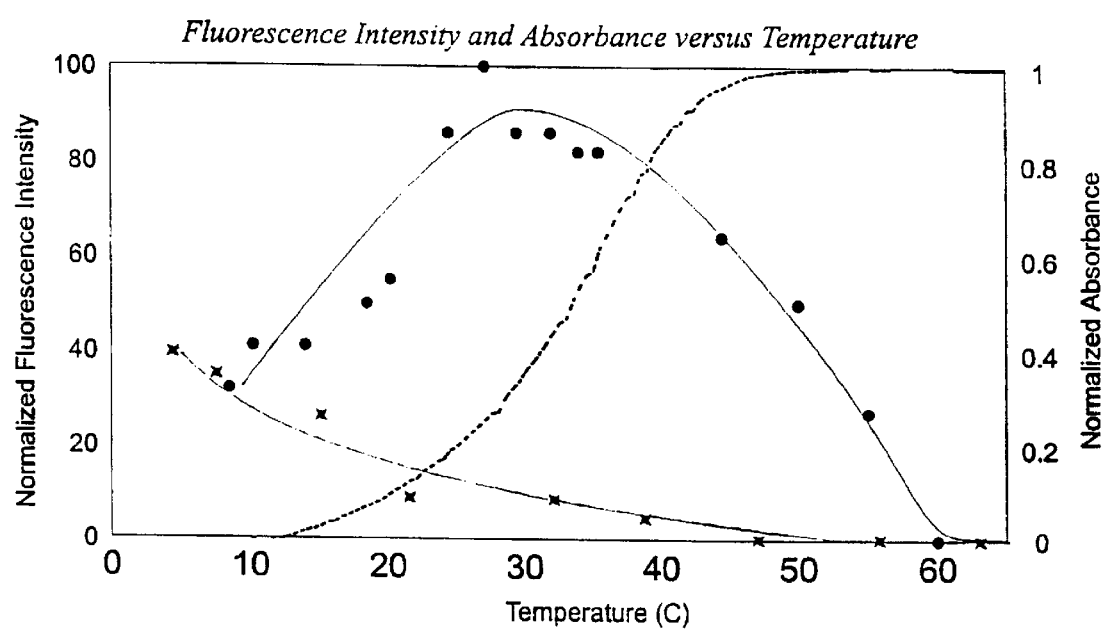
FIG. 16(c). Response (•) of the optical sensor with a 3'-end terminated Recognition Sequence to 40 pmol of 1 (see FIG. 15) in the presence of $2.5 \times 10^{-8}$ M ethidium bromide. Response (X) of the optical sensor to $2.5 \times 10^{-8}$ M ethidium bromide with no 1. ··· Melting profile of the same nucleic acid system in bulk solution by measurement of absorbance (260 nm) in 10 mM TRIS and 50 mM $MgCl_2$ at pH 7.3.

From FIG. 16(b), the fluorescent intensity versus temperature profile indicated that with dT$_{10}$ there was an initial increase in fluorescence indicative of duplex formation. This was followed by a decrease in the intensity which was indicative that triplex formation had occurred. Upon treatment of the optical sensor with 1, a decrease in fluorescence intensity for the reverse Hoogsteen complex at temperatures below the $T_m$ (35° C.) was observed FIG. 16(c), which is consistent with triplex formation. From the data of Scaria and Shafer (Scaria, P. V.; Shafer, R. H. *J. Biol. Chem.*, 1991, 266, 5417), it can be inferred that a temperature below 25° C. is required for the ethidium cation exclusion process to dominate the fluorescence intensity. Given that the quantity of ethidium cation that can be accommodated by triplexes is lower than that for duplexes (where intercalation occurs once every 2.8 base triplets and once per 2.4 base pairs at 25° C.) a 14% reduction in the amount of intercalated ethidium upon triple-strand formation results (Scaria, P. V.; Shafer, R. H. *J. Biol. Chem.*, 1991, 266, 5417). However, within the triplex structure the fluorescence quantum yield of the intercalated ethidium cation has been observed to increase by 19% for the $S_1 \rightarrow S_0$ transition, thereby resulting in an overall change in fluorescence intensity of +2.3%. Therefore, direct correlation between the $T_m$ for triplex formation and the onset of decreased fluorescence intensity from the optical sensor will be observed for systems of nucleic acids which have $T_m$ values at or below 25° C. This is consistent with our findings, FIGS. 16(a and b) where the decrease in fluorescence intensity from the sensor correlates well with the 17° C. $T_m$ for triplex formation. As can be seen in FIG. 16(c), although the transition for triple-strand formation between 1 and the immobilized $dA_{10}$ occurs at 35° C., a decrease in fluorescence intensity was not observed until the system was cooled to below 25° C. In this regard, our fluorescence studies involving ethidium bromide binding to triple-helices is in full agreement with several earlier findings. However, our system is then limited in terms of being able to identify only the duplex to triplex transition temperature for nucleic acid systems with $T_m$ values at or below 25° C.

x) PAGE Mobility Retardation Assay.

Figure 17A:
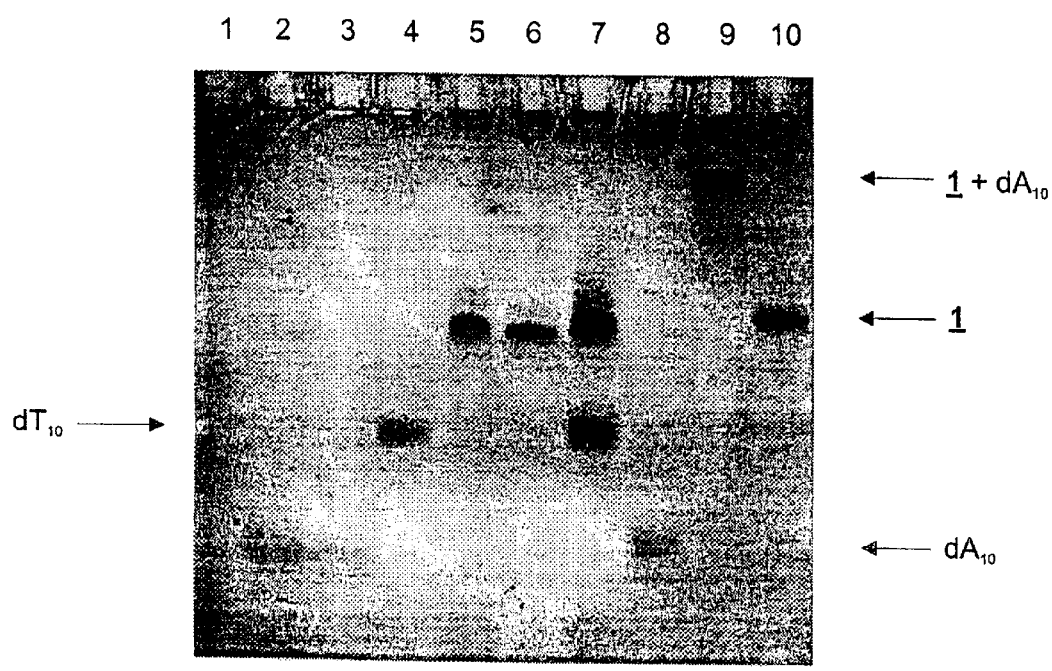
FIG. 17(a). Photograph of a UV-shadowed native polyacrylamide gel containing single strands, duplex and triple helical complexes of branched and linear controls. DNA samples were loaded in 50 mM $MgCl_2$, and 30% sucrose. Lanes 4–10 are $dT_{10}$, $dT_{10}{:}dA_{10}$ (1:1),. $dT_{10}{:}dA_{10}$ (2.5:1), $dT_{10}{:}dA_{10}$(4:1), $dA_{10}$, 1+$dA_{10}$, and 1, respectively. As can be noted the $dT_{10}{:}dA_{10}$ triplex (lane 7) showed a greater retardation in the mobility relative to the corresponding duplex (lanes 5 and 6). The slowest mobility was observed in lane 9 for 1: $dA_{10}$. Note: See FIG. 15 for the structure of 1.
Figure 17B:
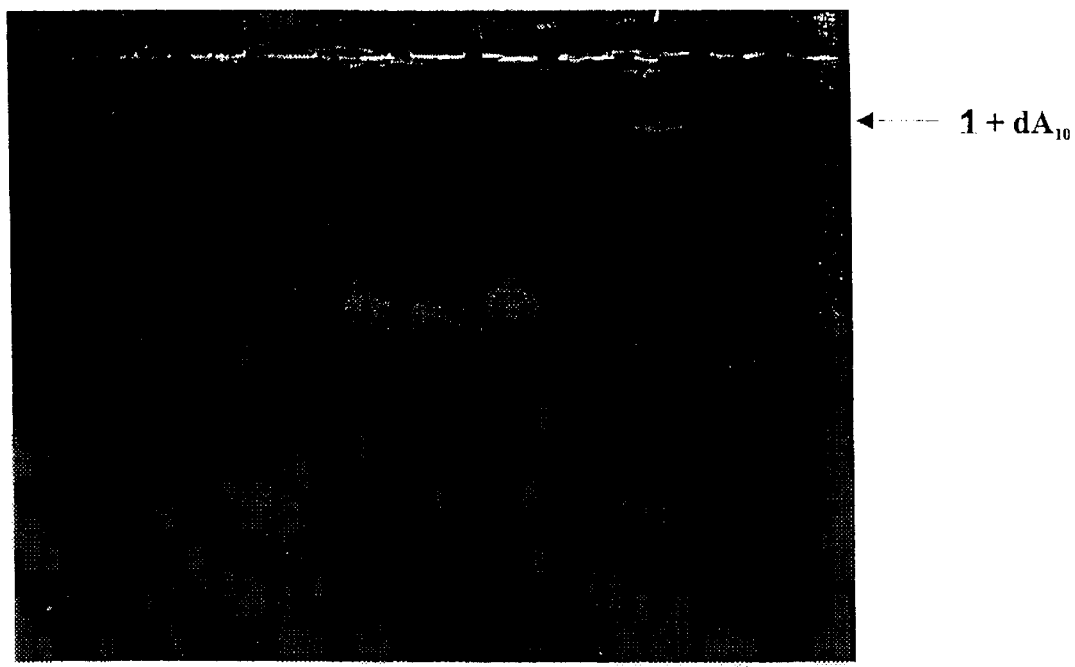
FIG. 17(b). Photograph of an ethidium bromide stained native polyacrylamide gel (same gel as FIG. 17{a}) containing single strands, duplex and triple helical complexes of branched and linear controls. DNA samples were loaded in 50 mM $MgCl_2$, and 30% sucrose. Lanes 4–10 are $dT_{10}$, $dT_{10}{:}dA_{10}$ (1:1), $dT_{10}{:}dA_{10}$ (2.5:1), $dT_{10}{:}dA_{10}$(4:1), $dA_{10}$, 1+$dA_{10}$, and 1, respectively. As can be noted the $dT_{10}{:}dA_{10}$ triplex (lane 7) showed a slight retardation in the mobility relative to the corresponding duplex (lanes 5 and 6). The slowest mobility was observed in lane 9 for 1: $dA_{10}$. Notice that only the duplexes and triplexes showed ethidium bromide fluorescence. Note: See FIG. 15 for the structure of 1.

Gel-shift experiments provided us with the opportunity to confirm the interaction of ethidium bromide with the complexes observed in these studies. The electrophoretic mobility of the Watson-Crick base paired $dT_{10}/dA_{10}$ duplex, (both the Hoogsteen and reverse-Hoogsteen paired TAT triplexes, and that of their component strands), was studied at 4° C. in a buffer containing magnesium. Following electrophoresis, the gels were visualized by UV shadowing, and by staining with ethidium bromide, as shown in FIGS. 17(a and b), respectively. The Hoogsteen triplex migrated more slowly than the duplex due to the presence of the third $dT_{10}$ strand. The reversed-Hoogsteen triplex has the slowest mobility of all, and is characteristic of branched nucleic acid structures [ref Hudson and Damha, JACS 1993; Wallace, J. C.; Edmons, M. PNAS vol. 80, 950–954, 1983). Association of 1 and $dA_{10}$ was quantitative as evidenced by the complete disappearance of compound 1 and $dA_{10}$, when mixed in equimolar amounts. The stoichiometry of interaction between $dT_{10}$ and $dA_{10}$ for the duplex and Hoogsteen triplex was also confirmed by studies at different concentrations of the two oligonucleotides. When the gel shown in FIG. 17(a) was stained with ethidium bromide and illuminated by a UV lamp, fluorescence was observed only in the bands corresponding to the complexes (not single strands). This is consistent with the well-known intercalation mechanism of ethidium bromide (Lim, C. S. *BioTechniques*, 1994, 17, 626.). As previously suggested by the biosensor studies, the $1/dA_{10}$ reverse Hoogsteen triplex gave the lowest fluorescence intensity, which could be related to the limited ability of ethidium to bind to this complex.

Example 15

Optical Sensors Which Function by the Intrinsic Mode of Operation

Background

Angularly dependent light scattering experiments were done to determine the refractive index of oligonucleotide monolayers covalently immobilized onto fused silica substrates. With knowledge of the refractive index of the immobilized oligonucleotide film, the mode of operation of the devices, namely, intrinsic or evanescent total internal reflection fluorescence, can be elucidated. The concept of the experiments done is based on classical optical theory with respect to how alterations in the direction of a ray or collimated beam of light traversing an interface between two dielectric materials may be predicted based on the difference in the refractive index of the two materials, and vice versa. In particular, Snell's law of refraction states that for a ray of light traveling in a plane normal to that defined by the interface between two materials of refractive index $n_1$ and $n_2$, the angular trajectory of the transmitted ray, $\theta_t$, from the normal to the interfacial plane will differ from that of the incident ray, $\theta_i$, by a quantity dependent on the difference in refractive index of the two materials. This can be solved for mathematically using the following equation (Ohanian, H. C.; Physics, W. W. Norton and Company, New York (1985) p. 837):

$$n_1 \cdot \sin(\theta_i) = n_2 \cdot \sin(\theta_t) \tag{4}$$

Figure 18:
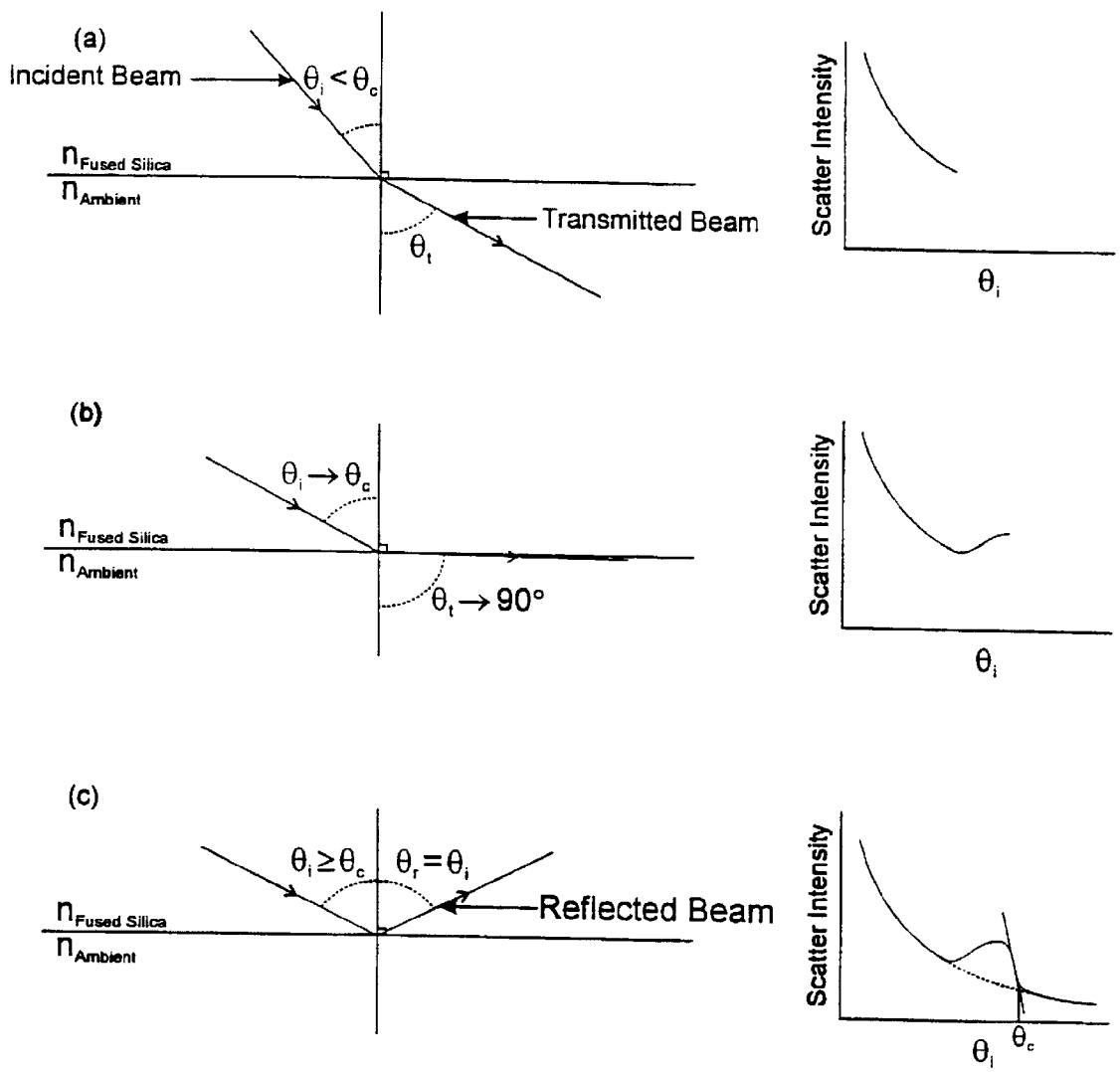
FIG. 18. Schematic diagram illustrating the experimental concept for light scattering investigations of a two-layer system with $n_{Fused\ Silica} > n_{Film}$.

FIG. 18(a) illustrates this concept for the case where the upper medium is fused silica and the lower medium is the ambient, as characterized by $n_{Fused\ Silica}$ and $n_{Ambient}$, respectively, where $n_{Fused\ Silica} > n_{Ambient}$. As shown in FIGS. 18(a) and 18(b), as the angle of incidence is increased, the angle of the refracted beam will be deflected by increasing amounts toward the interface, where at all times $\theta_i < \theta_t$. t. This trend is continued to the point where the refracted beam is directed into the interfacial plane (i.e. $\theta_t = 90°$). The angle of incidence for which this occurs is known as the critical angle, $\theta_c$, and can be calculated from the following relation:

$$\theta_c = \sin^{-1}\left(\frac{n_{Ambient}}{n_{Fused\ Silica}}\right) \tag{5}$$

For the case where $\theta_i \geq \theta_c$, the incident ray undergoes total internal reflection (TIR) at the interface. The angle of the reflected beam with respect to the normal to the interface is then equal to that of the angle of incidence for all $\theta_i \geq \theta_c$, as illustrated in FIG. 18(c).

If a detector for optical radiation was placed directly beneath the intersection point of the light ray with the interface and intensity was recorded as a function of incidence angle, a continuously decreasing intensity with increasing incidence angle would be observed. This observation is the result of the refracted beam being increasingly deflected out of the optical axis of the detector. An illustration depicting the trends in detector response is included on the right hand side of each ray diagram in FIGS. 18–20. As the refracted beam closely approaches the interface between the two dielectric materials, a local maxima in the detector response would be observed as a result of the beam being scattered by surface roughness and other imperfections at the interface. This would continue until $\theta_i = \theta_c$, after which point the incident beam would undergo TIR and hence provide negligible amounts of signal to the detector, with the exception of that which leaks out via scatter from imperfections at the interface and within the waveguiding media. As such, the critical angle for TIR can be determined directly from this point on the plot of scatter intensity versus incidence angle (FIG. 18(c)). For the case where the refractive index of one of the media is known, the refractive index of the other can be solved using equation (5).

Figure 19:
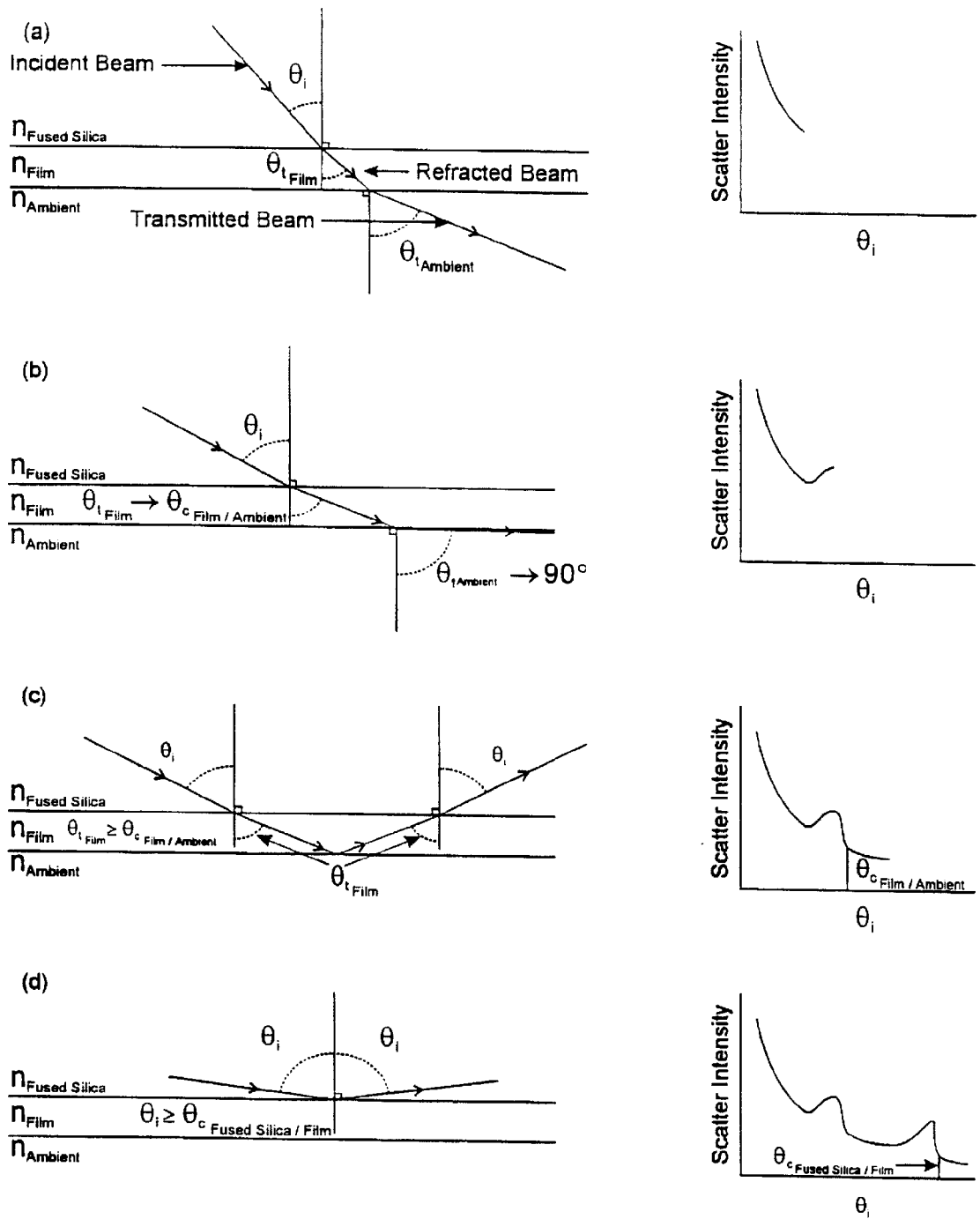
FIG. 19. Schematic diagram illustrating the experimental concept for light scattering investigations of a three-layer system with $n_{fused\ Silica} > n_{Film} > n_{Ambient}$.
Figure 20:
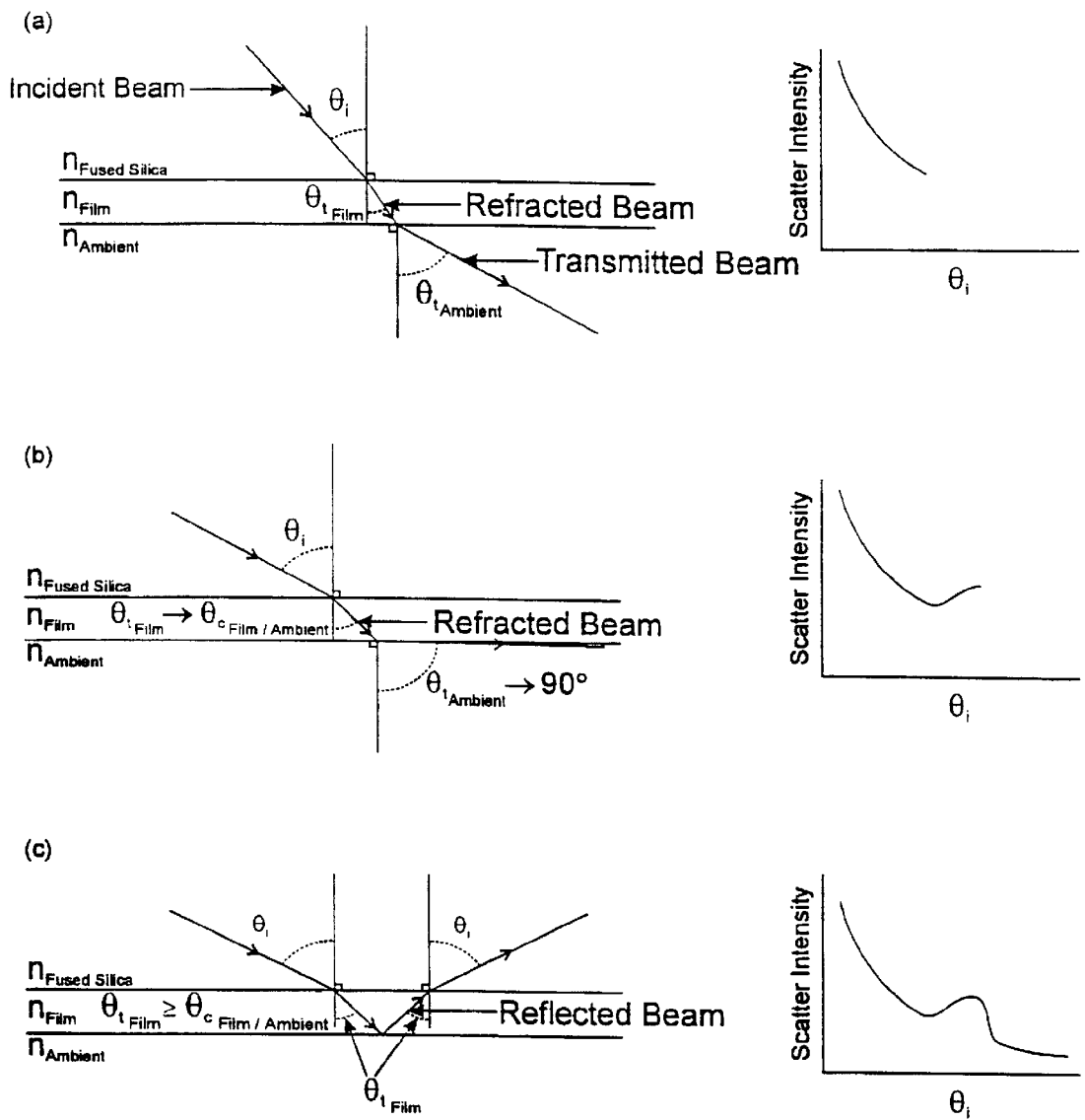
FIG. 20. Schematic diagram illustrating the experimental concept for light scattering investigations of a three-layer system with $n_{Fused\ Silica} < n_{Fim} > n_{Ambient}$.

A three-layer model must be considered for the case where a thin film of organic material is placed at the interface, as shown in FIGS. 19 and 20. Each medium type is herein characterized by the refractive index of the material, as given by $n_{Fused\ Silica}$, $n_{Film}$, and $n_{Ambient}$, respectively, for the fused silica, organic film, and ambient. The interaction of a light ray at each interface must be considered independently. An incident ray in the fused silica medium at an angle $\theta_i$, relative to the interfacial normal will be refracted to a differing angle after traversing each interface. The propagation angle of the ray will then be $\theta_{t_{film}}$, and $\theta_{t_{Ambient}}$ in the organic film and ambient media, respectively, relative to the interfacial normal.

For the case where $n_{Fused\ Silica} > n_{Film} > n_{Ambient}$, the reciprocal trend will be observed with respect to the propagation direction of the refracted rays, where $\theta_i < \theta_{t_{film}} < \theta_{t_{Ambient}}$, as shown in FIG. 19. As $\theta_i$ is increased, a local maxima in the detector response will be observed as $\theta_{t_{Film}}$ passes through the critical angle for TIR at the film-ambient interface. This is illustrated in FIG. 19(b and c). A second local maxima will be revealed as $\theta_i$ passes through the critical angle for TIR at the fused silica-film interface, as shown in FIG. 19(d). Given $n_{Fused\ Silica}$ and $n_{Ambient}$, the refractive index of the organic film can be directly determined from analysis of traces of scatter intensity versus $\theta_i$. The critical angle for the TIR at the fused silica-film interface can be directly obtained from the point where the second local maxima intersects the baseline scatter intensity, as described previously for the two-layer model and shown in FIG. 19(d). By substituting $\theta_{c_{Fused\ Silica/Film}}$ and $n_{Fused\ Silica}$ into equation 5, $n_{Film}$ can be solved for directly. Verification of this result can be acquired by substituting the calculated value of $n_{Film}$ and $n_{Ambient}$, and into equation 5 to determine the value of $\theta_{c_{Film/Ambient}}$. Using the value of $\theta_i$ from the point where the first local maxima intersects the baseline scatter intensity, $n_{Fused\ Silica}$, $n_{Film}$ and equation 4, a second method for calculating $\theta_{c_{Film/Ambient}}$ is provided. The goodness of agreement between the two values of $\theta_{c_{Film/Ambient}}$ would indicate the validity of the calculated value of $n_{Film}$.

For the case where $n_{Fused\ Silica} < n_{Film} > n_{Ambient}$, an estimate of the value for $n_{Film}$ may be attained provided the values of $n_{Fused\ Silica}$, $n_{Ambient}$ are known. A direct determination of $n_{Film}$ cannot be achieved in this case as TIR will not occur at the interface between the fused silica and organic film for light incident in the fused silica, yielding no mechanism for the determination of $\theta_{t_{Film}}$. The ray diagrams and detector response trends for this scenario are shown in FIG. 20. A slight underestimate for the value of $n_{Film}$ may be had by assuming that $\theta_{c_{Film/Ambient}}$ is equal to the value of $\theta_i$ at the termination point of the local maxima from the plot of scatter intensity versus incidence angle. This overestimate of $\theta_{c_{Film/Ambient}}$ and $n_{Ambient}$ can be used in equation 5 to provide an underestimate of the value of $n_{Film}$. This value of $n_{Film}$ along with those for $N_{Fused\ Silica}$ and $\theta_i$ can then be substituted into equation 4 to provide an underestimate of $\theta_{c_{Film/Ambient}}$. This underestimate of $\theta_{c_{Film/Ambient}}$ and $n_{Ambient}$ can again be used in equation 5 to provide an overestimate of $n_{Film}$. An average of these two values should provide a good estimate of the true value of $n_{Film}$ to within the uncertainty limits set by the low and high value extremes.

Materials and Methods

Planar Suprasil® fused silica wafers (Heraeus Amersil, Duluth, Ga., USA) with dimensions of 10×5×1 mm, a refractive index of 1.46008 and a surface flatness of 10 waves/inch, were functionalized with substrate linker molecules by the methods of examples 2 and 3. Similarly, silicon wafers (Heraeus Amersil, Duluth, Ga., USA) with dimensions of 10×5×1 mm were functionalized with substrate linker molecules by the methods of example 3. Polythymidilic acid icosanucleotides were then assembled onto the functionalized wafers by automated solid-phase oligonucleotide synthesis, as per the methods provided in example 5. All water used in the light scattering experiments was obtained from a Milli-Q 5 stage cartridge purification system (Millipore Corp., Mississauga, ON, Canada) and had a specific resistance not less than 18 MΩ·cm. The hybridization buffer was the same as that used for hybridization experiments on optical fibers and described in example 8. The refractive index of the hybridization buffer was determined by use of an Bausch & Lomb Abbe-3L Refractometer (Fisher Scientific, Nepean, ON, CA) to within the reported accuracy of 0.0001. Octadecyltrichlorosilane (OTS), ethylene glycol, hexadecane, carbon tetrachloride, chloroform and cyclohexane were of analytical grade or better from Aldrich Chemical Co. (St. Louis, Mo., USA) and used as received unless stated otherwise.

OTS functionalization of fused silica wafers

Fused silica wafers were cleaned by treatment with solutions of $NH_4OH/H_2O/H_2O_2$ and $HCl/H_2O/H_2O_2$ respectively, as per the method detailed in example 2 (i). Prior to use, carbontetrachloride and chloroform were dried by reflux over $P_2O_5$ under an argon atmosphere followed by distillation under the same conditions. Functionalization of the substrates with OTS monolayers was then done as per the methods of von Tscharner and McConnell (von Tschamer, V. and McConnell, H. M., *Biophys. J.*, 36 (1981) 421) and as described in the following. The cleaned substrates were treated with a solution of 80% hexadecane, 12% carbon tetrachloride, 8% chloroform and 0.1% OTS (v/v) for 15 minutes at 25° C. with stirring under an anhydrous argon atmosphere. The reaction mixture was then decanted and the functionalized fused silica wafers were then washed thrice with distilled chloroform and stored in-vacuo and over $P_2O_5$ until required.

Instrumentation used for Light Scattering Experiments

Figure 21:
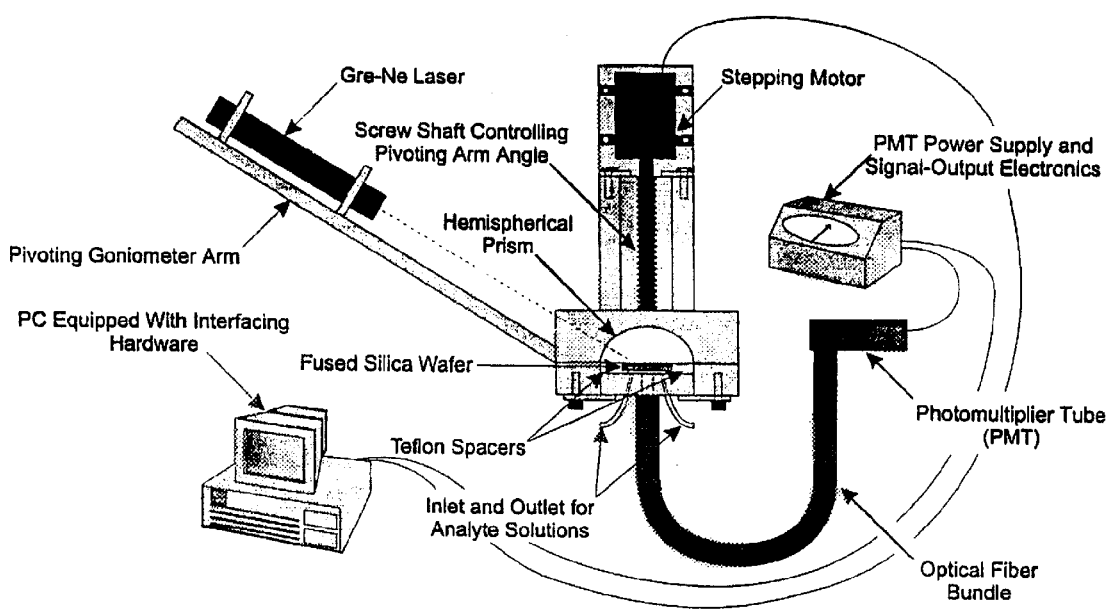
FIG. 21. Schematic diagram of the instrument used for investigations of angularly dependent light scatter.
Figure 22A:
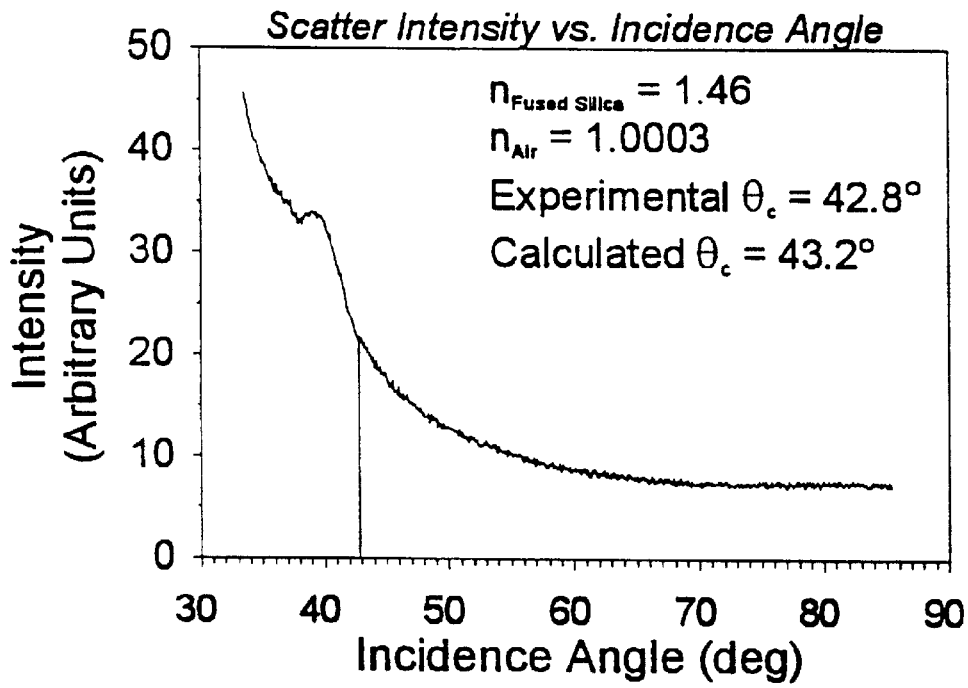
FIG. 22. Control experiments for the Angularly Dependent Light Scattering Technique Using Substances of Known Refractive Index.
Figure 22B:
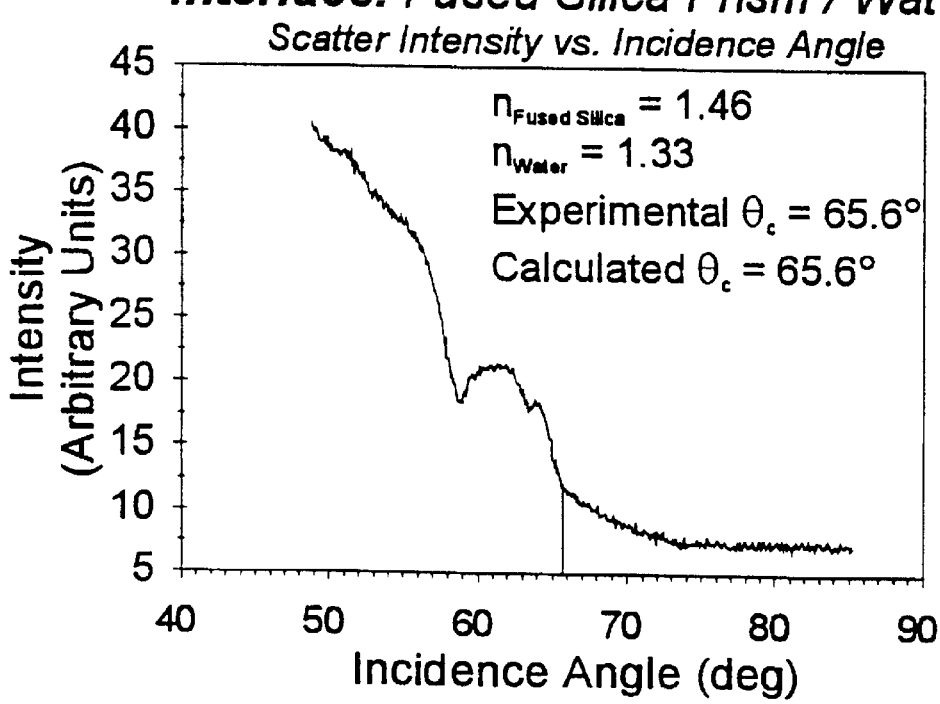
Figure 22C:
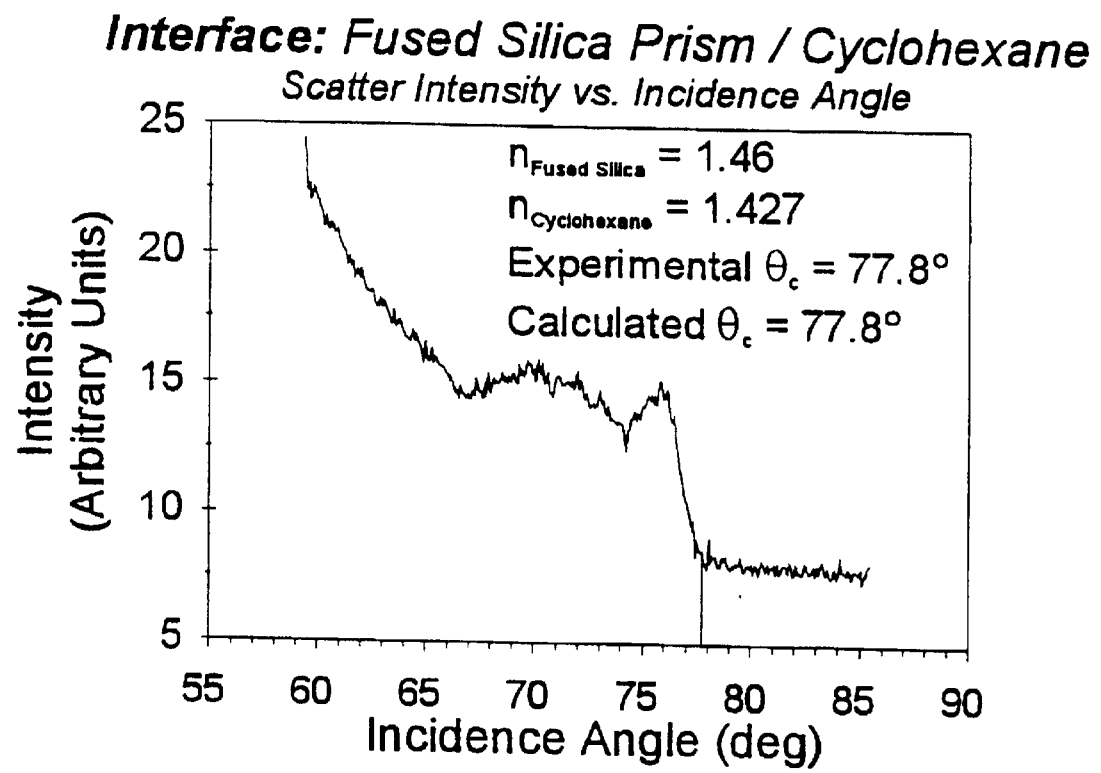
Figure 22G:
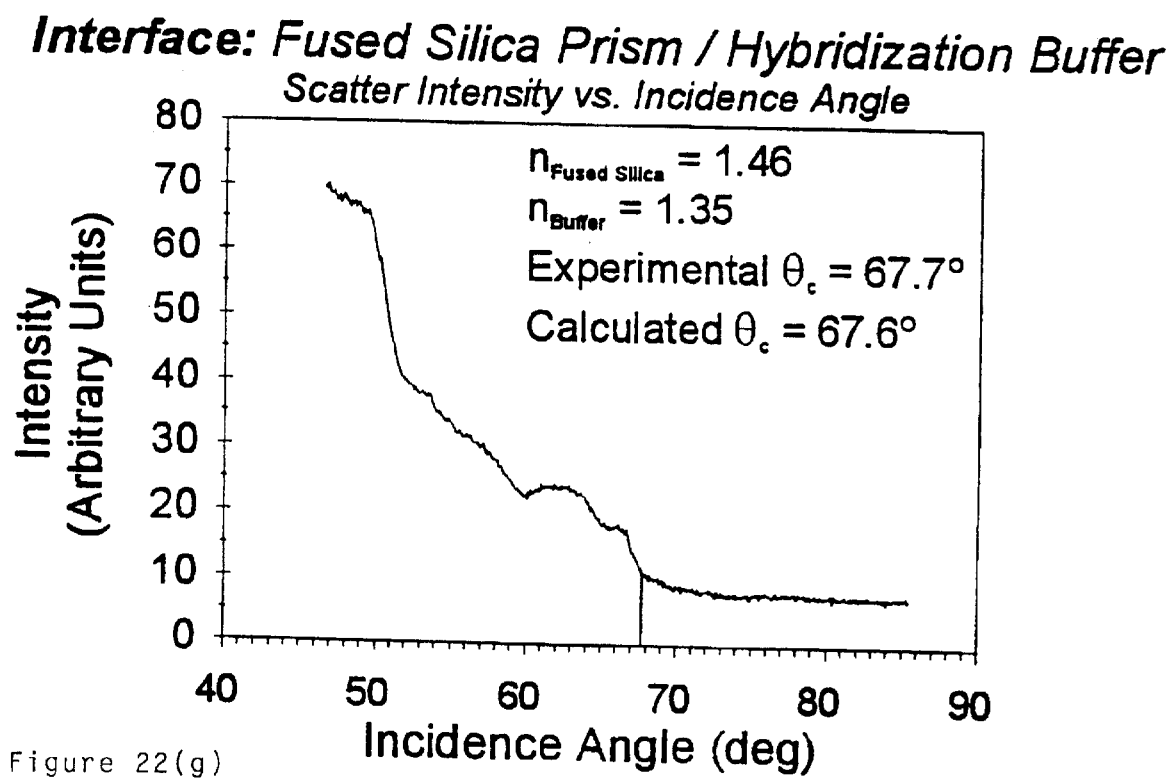
Figure 22D:
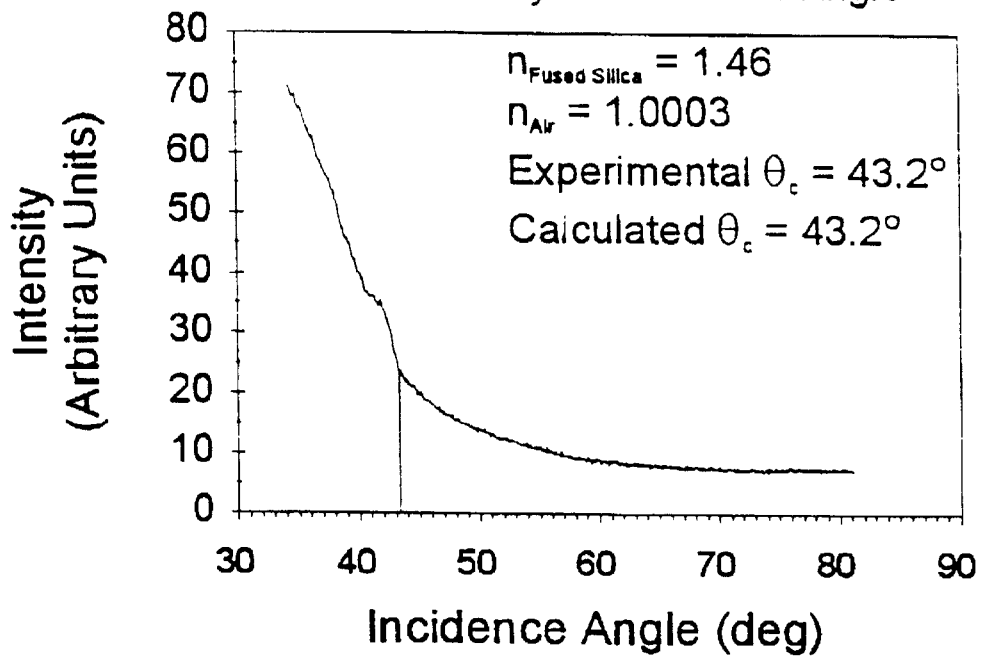
Figure 22E:
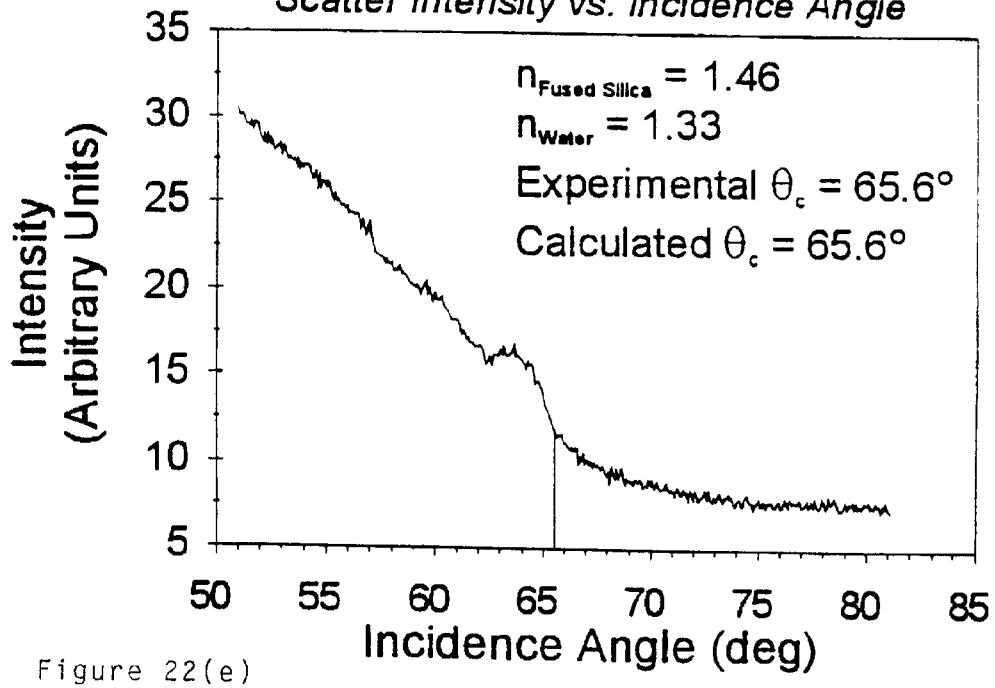
Figure 22F:
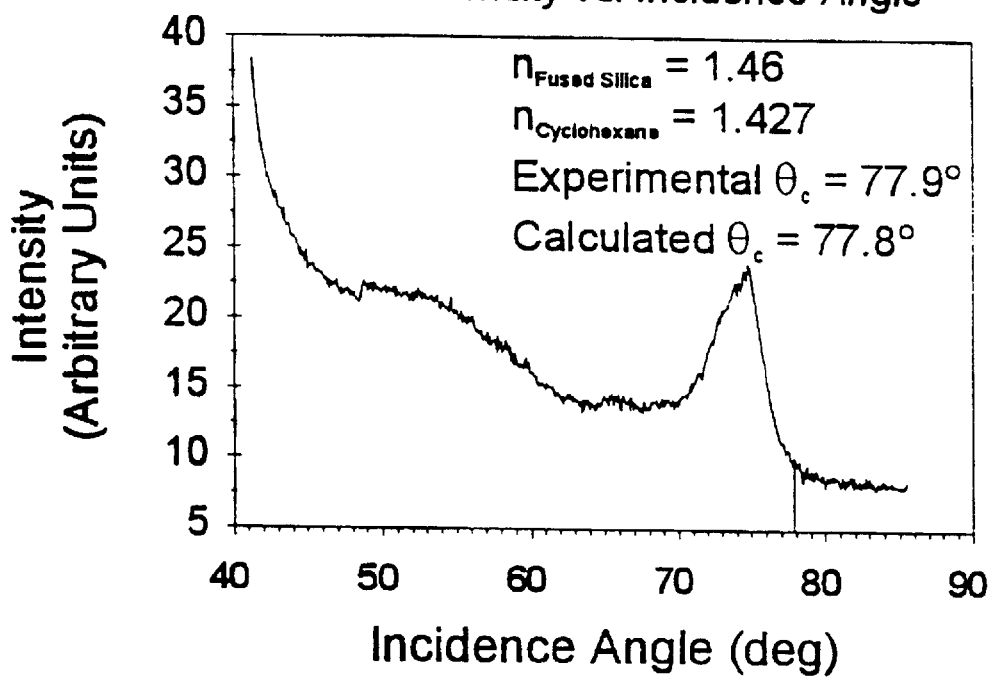

Wafers were placed in a custom-built stop-flow cell, beneath a Harrick EA 7×89 fused silica hemispherical prism with a radius of 8 mm (Harrick Scientific Corp., Ossington, N.Y., USA), as illustrated in FIG. 21. Optical contact between the fused silica hemispherical prism and fused silica wafer functionalized with an oligonucleotide monolayer was made by applying a thin film of fluorescence free Zeiss Immersionsoel 518C refractive index matching oil (n=1.515, Carl Zeiss Canada Ltd., Don Mills, ON, CA) at the interface between the two. The other face of the wafer was exposed to a solution compartment with dimensions of 9×2×1 mm (l×w×h). The flow cell was mounted at the vertex of a modified goniometer element obtained from a type 43702-200E Thin Film Ellipsometer (Rudolph Research Corporation, Flanders, N.J., USA) with an angular accuracy and precision of 0.005°. 543 nm optical radiation from a Gre-Ne™ Laser (Melles Griot, Carlsbad, Calif., USA, 1 mW output power, 1.5 mm beam diameter, 0.01 mrad beam divergence) mounted on one arm of the goniometer was passed through the hemispherical prism and impinged on the planar fused silica wafer. The hemispherical prism guaranteed that alterations in the incidence angle owing to refraction at the air-prism interface were eliminated as the beam invariably entered the prism normal to the prism/air interface. A M062-FC03 Slo-Syn stepping motor (Superior Electric Co., Bristol, Conn., USA, 200 steps per revolution) was coupled via a set of gears to the screw shaft of the goniometer used to drive the pivoting mechanism of the goniometer arms. The gear ratio used provided the motor with a 7× mechanical advantage so as to reduce the load on the motor and prevent it from slipping. TTL signals from a standard PC parallel interface were used to operate the advance mechanism of the stepper motor so as to offer accurate control of the angle of the goniometer arms and incidence of the laser beam. One end of a fiber-optic bundle (Oriel Corp, Stratford, Conn., USA, model no. 77533) was mounted in the base of the flow cell ca. 1 mm from the exposed face of the fused silica wafer. The other terminus of the fiber bundle was directed to a 630 nm long-pass colloidially-colored glass filter (Schott Glass Technologies, Duryea, Pa., USA) placed before the window of an R-928 photomultiplier tube (Hamamatsu Corp., Bridgewater, N.J., USA) operated using a DZ-112 Photoelectric Indicator (Rudolph Research, Flanders, N.J., USA). The long-pass filter provided for attenuation of the light intensity transmitted by the fiber bundle by a factor of $10^5$. This was done in order to prevent an overload condition in the PMT form occurring, guarantee the linearity of response and preserve the useful lifetime of the detector. The current from the PMT was converted to an analog voltage output (0–5 VDC) from the signal processing electronics contained within the Photoelectric Indicator and passed to a 12 bit analog to digital converter (Metra-Byte, Taunton, Mass., USA) for data acquisition on a PC computer using software created in-house to acquire plots of intensity versus incidence angle.

Results and Discussion

In order to test the validity of the light scattering approach for refractive index determination, samples of known refractive index were introduced into the flow cell beneath the hemispherical prism and analyzed by ramping the incidence angle of the laser mounted on the goniometer arm from low to high incidence angles while recording the observed scatter intensity. The results of experiments done using samples of air (n=1.0003), water (n=1.33), and cyclohexane (n=1.4266) are shown in FIG. 22(a–c), respectively and summarized in Table 2. Knowing the refractive index value of the prism material (fused silica, n=1.46) and the analyte, equation 5 was used to determine the critical angle values for TIR in each system. Good correlation with the predicted values was observed in all three cases with no more than 1% error between the experimental and theoretical values for $\theta_c$. An unmodified fused silica wafer was then coupled to the base of the prism and the same three control samples were again analyzed. Identical results within the resolution of the experimental technique were observed between the theoretical and observed values of critical angle for analyses done with and without the fused silica wafer. This indicated that no additional modifications to the instrument or correction factors would need be applied as a result of moving the intersection point of the laser beam 1 mm below the base of the prism. Hybridization buffer (n=1.35) was also analyzed by the light scattering method (FIG. 22(g)) and provided good agreement with the calculated value for $\theta_c$, based on the refractive index of the buffer as determined using a standard Abbe refractometer.

TABLE 2

Summary of the Results from the Angularly Dependent Light Scattering Experiments and Correlation with Controls of Known Refractive Index.

| Interface Type | $n_{Ambient}$ | Experimental $\theta_c$ | Calculated $\theta_c$ | % Error |
|---|---|---|---|---|
| Fused Silica Prism - Air | 1.0003 | 42.8° | 43.2° | 0.9 |
| Fused Silica Prism - Water | 1.33 | 65.6° | 65.6° | 0.0 |
| Fused Silica Prism - Cyclohexane | 1.427 | 77.8° | 77.8° | 0.0 |
| Fused Silica Prism - Hybridization Buffer | 1.35 | 67.7° | 67.6° | 0.1 |
| Fused Silica Wafer - Air | 1.0003 | 43.2° | 43.2° | 0.0 |
| Fused Silica Wafer - Water | 1.33 | 65.6° | 65.6° | 0.0 |
| Fused Silica Wafer - Cyclohexane | 1.427 | 77.9° | 77.8° | 0.1 |

Figure 23A:
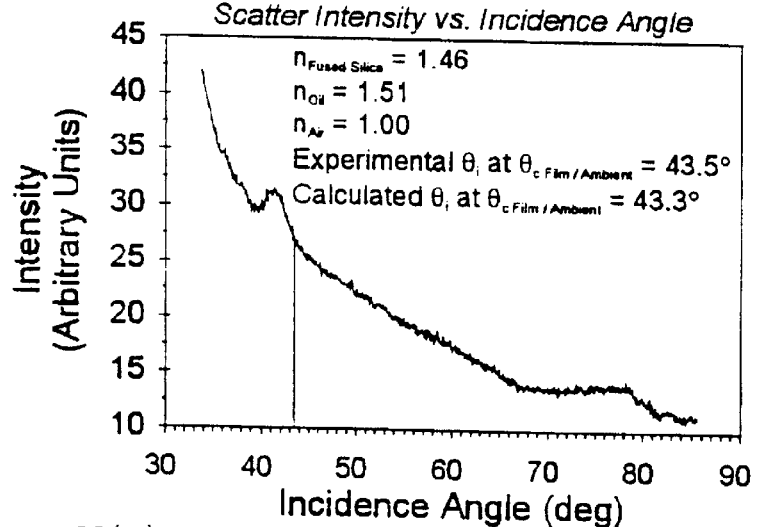
FIG. 23. Results of the light scattering experiments done with substrates coated with a thin organic films.
Figure 23B:
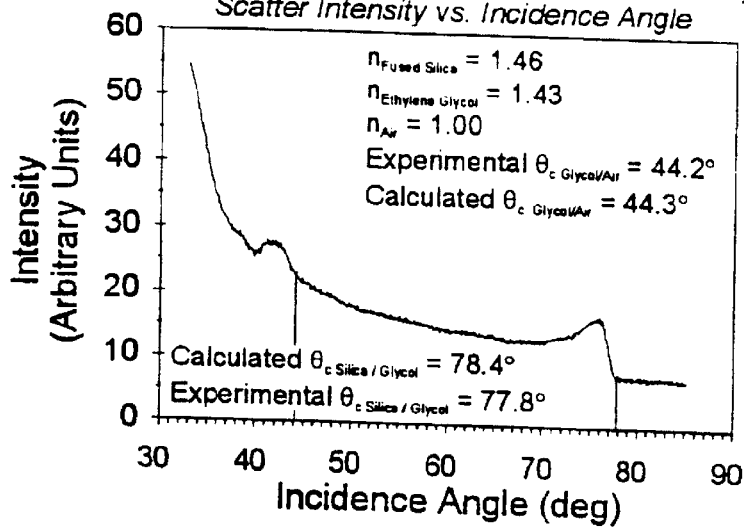

Experiments were then done using films of organic media of known refractive index in order to test the validity of the technique as applied to the previously described the three-layer model. Thin films (10–50 μm) of refractive index matching oil and ethylene glycol were applied to the exposed surface of the hemispherical prism and analysis was then done where air was used as the ambient in both cases. The results of the light scattering experiments for these samples are shown in FIGS. 23a and 23b, respectively. As can be seen in FIG. 23a, the experimentally determined value of $\theta_{c_{Film/Ambient}}=41.7°$ for the oil-air interface, based on a value of $\theta_i$ of 43.5°, and that predicted from theory, well agree after taking into account refraction of the beam upon traversing the fused silica—oil interface. However, for this particular example, the two-step approximation method for determination of $n_{Film}$ cannot be used in this example. The first assumption that $\theta_i=\theta_t$ used in this treatment leads to a first estimate of $n_{Film}$ which is lower than that of $n_{Fused\ Silica}$. This would lead to the result that the transmitted beam in the oil would be refracted away from the normal as opposed to towards the normal, as would be the case for $n_{Film}>n_{Fused\ silica}$. This causes the next approximation of $n_{Film}$ to be a more exaggerated underestimate of the true value. As such, films of refractive index slightly greater than that of the fused silica substrate cannot be solved for.

The results for the light scattering experiment using an ethylene glycol film provided very good agreement between the values of $\theta_c$ at each interface with respect to that calculated from theory. Of significance in this plot of scatter intensity versus incidence angle is the appearance of two distinct maxima. The observation of the two maxima concurs with that proposed for the three-layer model (FIG. 19) for the case where $n_{Fused\ silica}>n_{Film}>n_{Ambient}$. As such, information with regard to whether the refractive index of the organic film is greater than or less than that of the substrate material can be obtained by quick inspection.

Figure 23C:
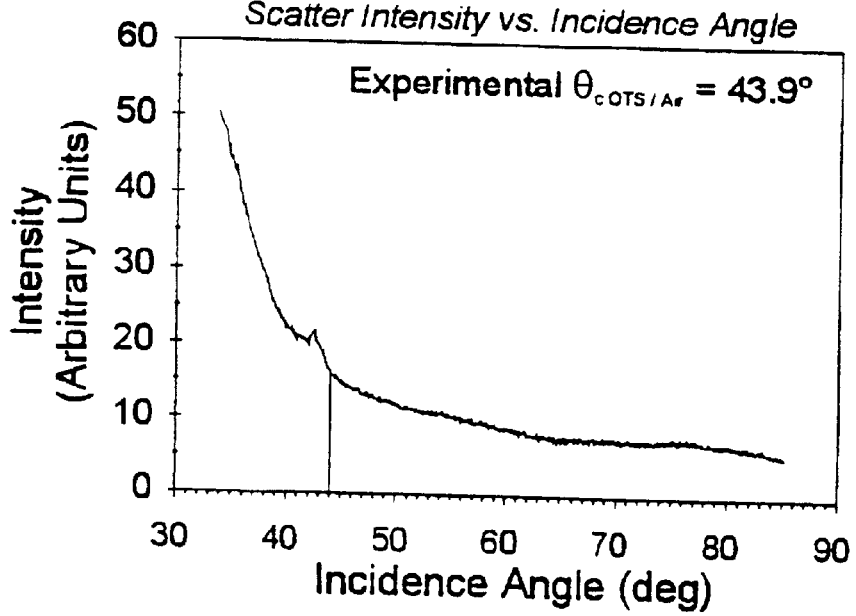
Figure 23D:
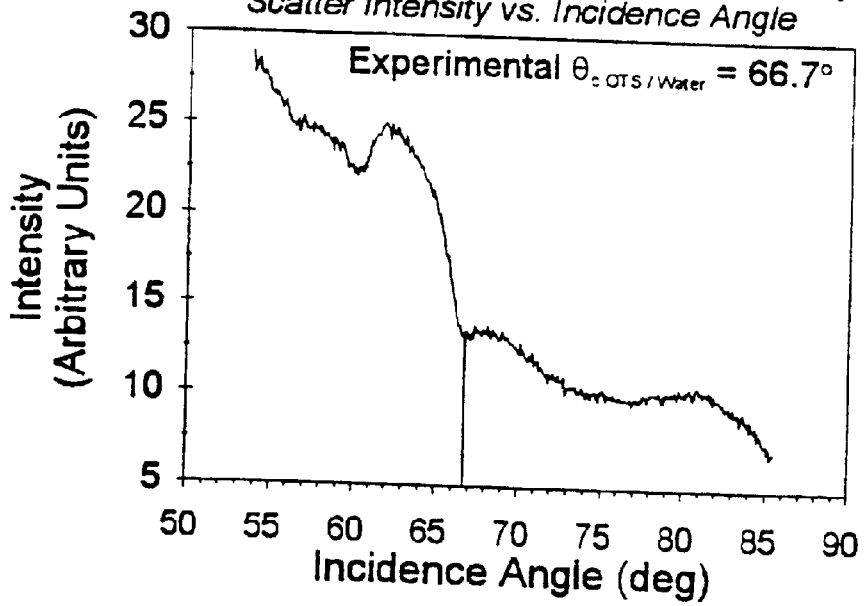

A monolayer film of OTS was covalently attached to the surface of a fused silica wafer by a method previously shown to provide dense surface packing and a theoretical refractive index in the range of 1.4–1.6. ({a}Ducharme, D. et al., J. Phys. Chem, 94 (1990) 1925. {b} von Tscharner, V. and McConnell, H. M.; Biophys J., 36 (1981) 421). The results of the light scattering experiments are shown in FIG. 23(c) and 23(d), respectively, for OTS functionalized fused silica wafers exposed to air and water as the ambient. Using the following rearrangement of equation 5:

$$n_{Film} = \frac{n_{Ambient}}{\sin\theta_{c_{Film/Ambient}}} \quad (6)$$

the value of the refractive index for the OTS monolayer could be solved for. Values of 1.44 and 1.45 for the refractive index of the monolayer were determined from the analyses using air and water as the ambient, respectively. Given that the refractive index values determined for the OTS monolayer differed by ~1% with that of the fused silica substrate, the same limitation as observed for the refractive index matching oil layer applies herein. As such, it can only be assumed that the refractive index of the OTS overlayer is only slightly greater than that of the fused silica. This is reinforced by the fact that of only one local maxima in the plot of scatter intensity versus incidence angle was observed. If the film refractive index was indeed less than that of the fused silica substrate then two local maximas should have been observed, in accord with the three-layer model concept and as clearly demonstrated by the experiment using ethylene glycol for the film (FIG. 23(b)).

Figure 24A:
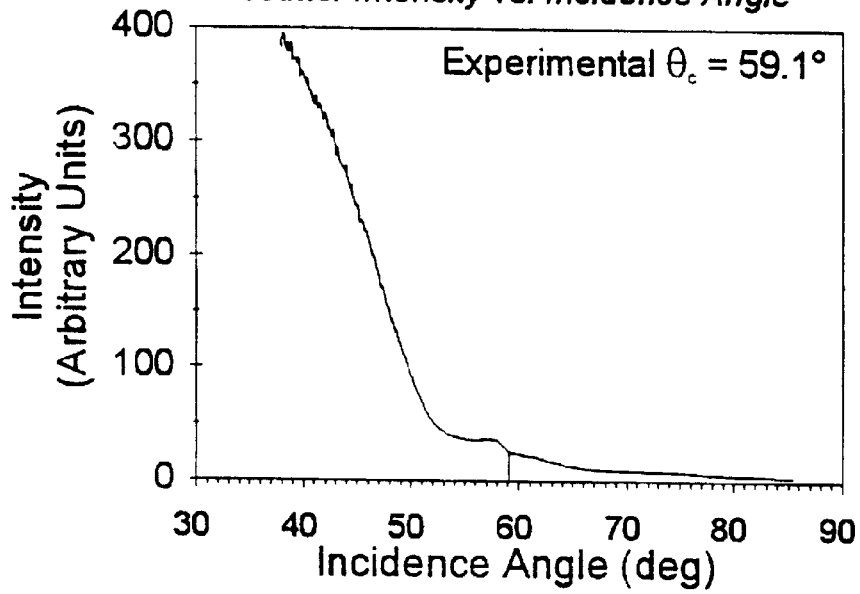
FIG. 24. Results of the light scattering experiments done with substrates coated with covalently immobilized oligonucleotides.
Figure 24B:
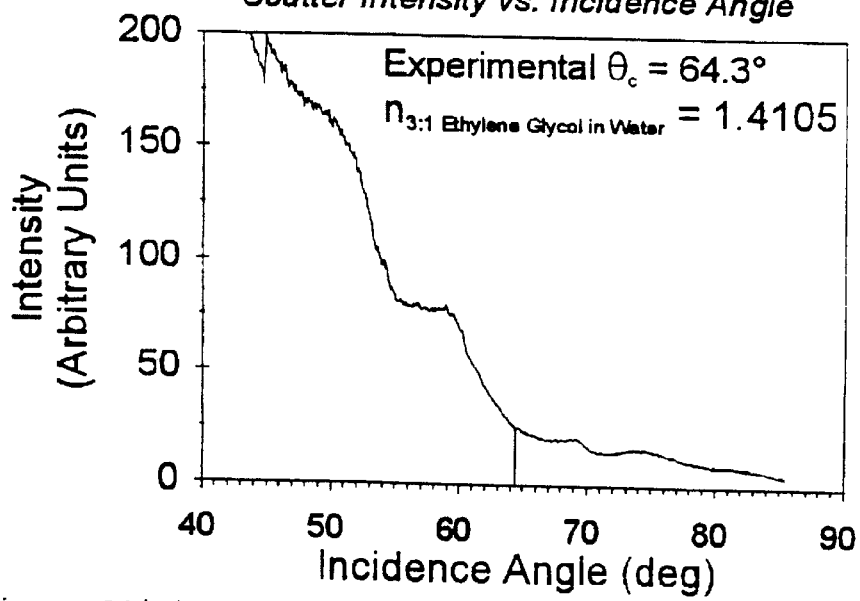
Figure 24C:
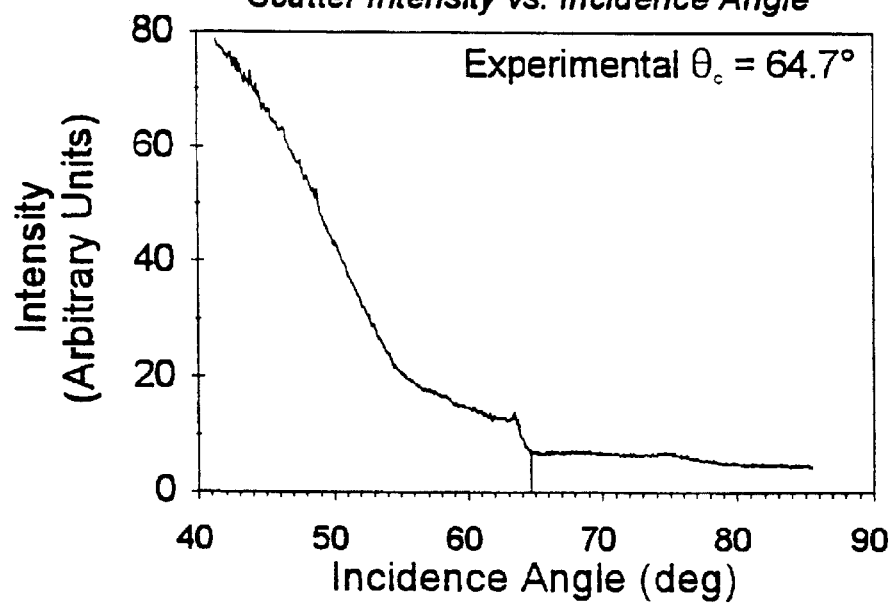

Samples of fused silica wafer functionalized with substrate linker molecules by the methods of example 2 and 3 onto which polythymidilic acid icosanucleotides were assembled by the method of example 5 were analyzed by the angularly dependent light scattering technique. The results of the analysis are shown in FIG. 24(a) and 24(b) for samples prepared by the mesylate activation scheme as detailed in example 3. The results for samples prepared by the GOPS-HEG protocol given in example 2 are shown in FIG. 24(c). For the samples prepared by mesylate activation for which water and 3:1 ethylene glycol in water solution was used as the ambient, a value of 1.57 was determined in both cases for the underestimate of $n_{film}$, based on the assumption that $\theta_{t_{Film}} = \theta_i$. Subsequent to the recalculation of $\theta_{t_{Film}}$ based on the underestimated value of $n_{Film}$, overestimates for $n_{Film}$ of 1.67 and 1.68, respectively, were determined from the cases where water and 3:1 ethylene glycol in water were used as the ambient. This provided an average value for $n_{Film}$ of 1.62±0.05. Similarly, analysis of the fused silica wafer functionalized with polythymidilic acid icosanucleotide on GOPS-HEG substrate linkers (example 2) yielded an average value for $n_{Film}$ of 1.48±0.01. The fact that estimates of $n_{Film}$ for both types of nucleic acid—substrate linker overcoating could be solved for strongly reinforces the fact that these overlayers on the fused silica substrates indeed possess a larger value of refractive index than that of the substrates onto which they are immobilized.

In addition to the light scattering experiments, ellipsometry was done in order to provide secondary confirmation of the experimentally determined values of the refractive index for the oligonucleotide monolayers. Ellipsometry was done on samples of silicon wafer functionalized with substrate linker molecules by the methods of example 3 onto which molecules of polythymidilic acid icosanucleotide were assembled by automated solid-phase oligonucleotide synthesis as detailed in example 5. Silicon wafers were necessarily used as the substrate material for these experiments as the fused silica substrates used for the light scattering experiments provide little reflection of the laser beam incident at an angle 70° in the ambient. The surface of the silicon wafers was made similar to that of fused silica via the cleaning procedure used prior to functionalization of the substrate. This cleaning procedure is known to provided a layer of oxidized silicon at the surface of the silicon wafers (Kern, W. and Puotinen, D. A.; RCA Review, 31 (1970) 187–206). As such, silanol moieties then present at the oxidized silicon-ambient interface provide attachment points for the substrate linker molecules.

McCracken (F. L. McCracken, NBS Technical Note 479, Washington D.C. (1969)) has developed software capable of providing values of thickness and refractive index from ellipsometric measurements of thin films using the exact Drude equations for ellipsometry. The Film 85 software provided with the AutoEL-II null reflection ellipsometer (Rudolph Research Corp., Flanders, N.J., USA) was based on that originally developed by McCracken and used for the analysis of ellipsometric data from the experiments described herein. Ellipsometric analysis of the cleaned substrate revealed the formation of a 20 Å thick layer of oxidized silicon on the surface of the wafers. Three silicon wafers functionalized with substrate linker and oligonucleotide where then analyzed. Ten different locations on the wafer surfaces were chosen at random and the results of the ellipsometric analysis are summarized below in Table 3.

TABLE 3

Results of Ellipsometric Analysis of Oxidized Silicon Substrates Functionalized with Substrate Linker Molecules by the Methods of Example 3 and Polythymidilic Acid Icosanucleotide by the Methods of Example 5.

| Sample Number | Film Thickness (Å) Estimated Using the Iterative Calculation Method of Program 12. | Film Refractive Index Estimated Using the Iterative Calculation Method of Program 12. | Corrected Refractive Index for a Film of 100Å Thickness. |
|---|---|---|---|
| 1 | 84 | 2.090 | 1.76 |
| 2 | 103 | 1.764 | 1.81 |
| 3 | 113 | 1.372 | 1.55 |
| 4 | 108 | 1.402 | 1.51 |
| 5 | 75 | 2.115 | 1.59 |
| 6 | 72 | 2.189 | 1.58 |
| 7 | 76 | 2.091 | 1.59 |
| 8 | 82 | 2.129 | 1.75 |
| 9 | 81 | 2.119 | 1.72 |
| 10 | 73 | 2.132 | 1.56 |
| | | Average Value ± σ | 1.6 ± 0.1 |

As can be seen by inspection of the data shown in Table 3, determination of thickness and refractive index concurrently via the iterative process provides a large degree of variation. This is based largely on the fact that the covalently immobilized nucleic acid membrane system is not ideal for ellipsometric analysis in that it violates many of the assumptions of the Drude equations. Of particular significance is the fact that a densely packed oligonucleotide film with the nucleic acid strands oriented perpendicular to the air-film boundary would be uniaxially anisotropic. This would cause alterations in the speed of the p- and s-polarized components of the light beams upon passage through the oligonucleotide film. This effect has been known to produce relative errors in thickness of up to 10% (R. M. A. Azzam and N. M. Bashara, *Ellipsometry and Polarized Light*, North Publishing Company, New York (1977)).

A better estimate of the refractive index of the immobilized nucleic acid films may be achieved by application of Maxwell-Garnet theory (R. M. A. Azzam and N. M. Bashara, *Ellipsometry and Polarized Light*, North Holland Publishing Company, New York (1977), p. 359). The concept of Maxwell-Garnet theory, as applied herein, is based on the notion that a partially formed monolayer film of coverage Θ is optically equivalent to a fully formed monolayer film of refractive index ($n_{Film}$) and relative thickness ($T_f$) such that the observed film thickness (T) is related to that of the fully formed film by:

$$T = \Theta T_f \qquad (7)$$

Likewise, the same scaling factor, Θ, can be applied to the refractive index value given from ellipsometric analysis so that values more representative of that for the actual immobilized layers can be obtained. The results after applying this correction are given in Table 3 and provided an average value of 1.6±0.1 for $n_{Film}$.

The good correlation between the result of the light scattering experiments and ellipsometry provides unequivocal evidence that monolayers of oligonucleotides can be assembled onto substrate linker functionalized fused silica substrates of higher refractive index than that of the substrate material. Oligonucleotides assembled onto fused silica wafers functionalized with substrate linker molecules via the mesylate activation scheme, as outlined in example 3 were observed to provide immobilized nucleic acid monolayers with a refractive index of 1.62±0.05 by light scattering investigations. This correlated well to the refractive index value of 1.6±0.1 obtained by ellipsometric investigations. Light scattering investigation of oligonucleotides assembled onto fused silica wafers functionalized with substrate linker molecules via the methods of example 2, revealed a nucleic acid film refractive index of 1.48±0.01, which also is higher than that of the fused silica substrates onto which they are covalently attached. As such, optical sensors created by the methods reported herein will then function by and provide the signal throughput advantages associated with the intrinsic TIRF motif described previously.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications, patents and patent applications are herein incorporated by reference in their entirety to the same extent as if each individual publication, patent or patent application was specifically and individually indicated to be incorporated by reference in its entirety. This application also claims priority from U.S. application Ser. No. 60/050,970 and Canadian application no. 2,208,165, both of which are incorporated by reference.

We claim:

1. A biosensor for detecting a target nucleic acid in the presence of a fluorophore by detection of fluorescence from the fluorophore which comprises:
    (a) an optical element having an index of refraction and which comprises an interaction surface;
    (b) an immobilized layer having an index of refraction which comprises a nucleic acid or nucleic acid analogue covalently attached to the interaction surface of the optical element, the nucleic acid or nucleic acid analogue capable of hybridizing to the target nucleic acid to form a hybridized nucleic acid complex;
    (c) a light source for introducing light capable of stimulating fluorescence of the fluorophore into the optical element in contact with the interaction surface; and
    (d) a detector for detecting fluorescence emitted by the fluorophore on binding to a hybridized nucleic acid complex;
wherein the index of refraction of the immobilized layer is equal to or greater than the refractive index of the interaction surface of the optical element such that direct excitation of the fluorophore in the immobilization layer to emit fluorescence results in the detection of the target nucleic acid.

2. The biosensor of claim 1 wherein the index of refraction of the immobilized layer is controlled by changing the density of molecules immobilized on the interaction surface of the optical element.

3. The biosensor of claim 2 wherein the index of refraction of the immobilized layer is controlled by changing the density of nucleic acids or nucleic acid analogs immobilized on the interaction surface.

4. The biosensor of claim 1 wherein the nucleic acid or nucleic acid analogue is attached to the interaction surface through a linker molecule.

5. The biosensor of claim 4 wherein the index of refraction of the immobilized layer is controlled by changing the density of linker molecules immobilized on the interaction surface of the optical element.

6. The biosensor of claim 4 wherein the index of refraction of the immobilized layer is increased by increasing the density of linker molecules immobilized on the interaction surface of the optical element.

7. The biosensor of claim 4 wherein the linker is at least about 25 Å in length.

8. The biosensor of claim 4 wherein the linker contains ethylene glycol subunits.

9. The biosensor of claim 4 wherein the linker is hexaethylene glycol.

10. The biosensor of claim 4 wherein the nucleic acid or nucleic acid analogue is attached to the linker by in situ synthesis.

11. The biosensor of claim 10 wherein the nucleic acid is attached to the linker by in-situ solid-phase oligonucleotide synthesis.

12. The biosensor of claim 11 wherein the nucleic acid is attached to the linker by in situ oligonucleotide synthesis using the β-cyanoethylphosphoramidite method.

13. The biosensor of claim 10 wherein the nucleic acid or nucleic acid analogue has 50 or fewer bases.

14. The biosensor of claim 4 wherein a free strand of nucleic acid or nucleic acid analogue is covalently attached to the linker.

15. The biosensor of claim 1 wherein the immobilization layer comprises a fluorophore.

16. The biosensor of claim 1 wherein the fluorophore is covalently tethered to the nucleic acid or nucleic acid analogue in the immobilization layer.

17. The biosensor of claim 1 wherein the fluorophore is provided in a solution into which the biosensor is immersed.

18. The biosensor of claim 1 wherein the index of refraction of the immobilized layer is in the range 1.4 to 1.6.

19. The biosensor of claim 1 wherein the index of refraction of the immobilized layer is 1.62.

20. The biosensor of claim 1 wherein the optical element is an optical waveguide.

21. The biosensor of claim 1 wherein the optical element is an optical fiber.

22. The biosensor of claim 21 wherein the optical fiber is a fused silica fiber.

23. The biosensor of claim 1 wherein the detection limit is below $10^6$ molecules of target nucleic acid.

24. The biosensor of claim 1 for detecting more than one different target nucleic acid wherein the immobilized layer includes, for each target nucleic acid, a nucleic acid or nucleic acid analogue capable of hybridizing to that target nucleic acid.

25. The biosensor of claim 24 wherein a fluorophore is covalently tethered to nucleic acids or nucleic acid analogues.

26. The biosensor of claim 25 wherein the fluorophores covalently tethered to different nucleic acids or nucleic acid analogues emit fluorescence at different wavelengths.

27. The biosensor of claim 1 wherein the index of refraction of the immobilized layer is in the range 1.4 to 1.6 and the nucleic acid or nucleic acid analogue is attached to the interaction surface through a linker molecule which contains an ethylene glycol subunit.

28. The biosensor of claim 27 wherein the linker molecule is hexaethylene glycol.

29. A method for detecting a target nucleic acid in a sample which comprises the steps:
    (a) contacting the immobilized layer of the biosensor of claim 1 with the sample such that target nucleic acids in the sample can hybridize to the nucleic acids or nucleic acid analogues of the immobilization layer;

(b) contacting the immobilization layer of the biosensor with a fluorophore and allowing the fluorophore to bind to hybridization complexes of the nucleic acids or nucleic acid analogues with the target nucleic acid in the immobilization layer;

(c) introducing light into the optical element of the biosensor in contact with the interaction surface of the optical element to stimulate emission from bound fluorophore; and (d) detecting the fluorescence emitted by bound fluorophore whereby the target nucleic acid is detected.

30. The method of claim 29 wherein the immobilization layer is contacted with the fluorophore by covalent bonding within the immobilization layer.

31. The method of claim 29 wherein the immobilization layer is contacted with the fluorophore by covalently tethering the fluorophore to nucleic acids or nucleic acid analogues of the immobilization layer.

32. The method of claim 29 wherein the target nucleic acid is a nucleic acid of bacteria, viruses, fungi, unicellular or multicellular organisms.

33. The method of claim 29 wherein the target nucleic acid is a nucleic acid of a cell, a cellular homogenate, a tissue or an organ.

34. The method of claim 29 wherein the biosensor is internally calibrated by comparing fluorescence emission from the fluorophore in the immobilization layer before and after the biosensor is contacted with the sample.

35. The method of claim 34 wherein the biosensor is internally calibrated using time-resolved fluorescence measurements.

36. A method for detecting more than one target nucleic acid in a sample which comprises the steps:

(a) contacting the immobilized layer of the biosensor of claim 24 with the sample such that target nucleic acids in the sample can hybridize to the nucleic acids or nucleic acid analogues of the immobilization layer;

(b) allowing the covalently tethered fluorophores of the immobilization layer to bind to hybridization complexes of the nucleic acids or nucleic acid analogues with the target nucleic acid in the immobilization layer;

(c) introducing light into the optical element of the biosensor in contact with the interaction surface of the optical element to stimulate emission from bound fluorophore; and (d) detecting the fluorescence emitted by bound fluorophore whereby the target nucleic acid is detected.

37. The method of claim 36 wherein the target nucleic acids are nucleic acids of a bacterium, a virus, a fungus, a unicellular or a multicellular organism.

38. A method for detecting triplex formation or multistranded nucleic acid formation between one or more target nucleic acids or nucleic acid analogues in a sample and an immobilized nucleic acid or nucleic acid analogue which comprises the steps:

(a) providing a biosensor which comprises
an optical element having an index of refraction and comprising an interaction surface, and an immobilized layer having an index of refraction and including a nucleic acid or nucleic acid analogue covalently attached to the interaction surface of the optical element, wherein the index of refraction of the immobilized layer is equal to or greater than the refractive index of the optical element;

(b) contacting the immobilization layer with a fluorophore;

(b) introducing light into the optical element in contact with the interaction surface such that fluorescence is stimulated and emitted from the fluorophore in the immobilization layer;

(c) detecting fluorescence emitted by the fluorophore in the immobilization layer;

(d) contacting the sample with the immobilization layer of the biosensor such that triplexes or multistranded nucleic acid complexes can be formed and such that fluorophores of the immobilization layer can bind to triplexes or multistranded nucleic acid complexes;

(e) introducing light into the optical element in contact with the interaction surface such that fluorescence is stimulated and emitted from bound fluorophore;

(f) detecting fluorescence emitted by the bound fluorophore;

(g) detecting the difference in fluorescence emitted by the fluorophore before and after triplex or multistranded nucleic acid complex formation to thereby detect triplex formation or multistranded nucleic acid formation.

39. The method of claim 38 wherein the immobilized layer is contacted with fluorophore by covalently tethering fluorophores to the nucleic acid or nucleic acid analogue in the immobilization layer.

40. The method of claim 38 wherein the optical element is an optical waveguide.

41. The method of claim 38 wherein the target nucleic acid or nucleic acid analogues in the sample is a branched nucleic acid.

42. A method for making a biosensor of claim 1 which comprises the steps of:

(a) activating the interaction surface of the optical element of the biosensor;

(b) attachment of nucleic acids or nucleic acid analogues, which can hybridize to the target nucleic acid, to the activated interaction surface;

(c) measurement of the refractive index of the immobilized layer by angularly dependent light scattering; and (d) adjusting the conditions of step b, if necessary, to obtain an immobilized layer having an index of refraction equal to or greater than the index of refraction of the optical element.

43. The method of claim 42 wherein the optical element is an optical fiber.

44. The method of claim 42 further comprising the step of covalently bonding a fluorophore in the immobilization layer.

45. The method of claim 42 wherein the fluorophore is covalently tethered to a nucleic acid or nucleic acid analogue in the immobilization layer.

46. The method of claim 42 wherein the optical element is a fused silica optical fiber.

47. The method of claim 42 wherein the interaction surface of the optical fiber is activated by treatment with methanesulfonyl chloride or an organosilane prior to attachment of the linker.

48. The method of claim 47 wherein the organosilanes are glycidoxypropyltrimethoxysilane or aminopropyltriethoxysilane.

49. The method of claim 42 wherein one terminus of the linker is protected prior to reaction with the activated interaction surface of the optical element.

50. The method of claim 42 wherein the nucleic acid or nucleic acid analogue is attached to the linker by in situ synthesis.

51. The method of claim 42 wherein free strands of nucleic acid or nucleic acid analogue are covalently attached to the linker.

```
                              SEQUENCE LISTING

<160> NUMBER OF SEQ ID NOS: 1

<210> SEQ ID NO 1
<211> LENGTH: 20
<212> TYPE: DNA
<213> ORGANISM: Candida albicans
<220> FEATURE:
<221> NAME/KEY: misc_feature
<222> LOCATION: (1)..(20)
<223> OTHER INFORMATION: Oligonucleotide probe

<400> SEQUENCE: 1
taggtgagac atatcacaga                                                   20
```

52. The biosensor of claim 1 which operates in the intrinsic mode.

53. The biosensor of claim 1 wherein emitted fluorescence is captured by the optical element and conveyed to the detector.

54. The biosensor of claim 53 wherein the optical element is an optical fiber.

55. The biosensor of claim 1 wherein the immobilized layer is formed on an interaction surface along the length of the optical element and not at an end of the optical element.

56. The biosensor of claim 55 wherein the optical element is an optical fiber.

57. A biosensor of claim 1 wherein the optical element is a single optical fiber.

58. The method of claim 42 wherein nucleic acids or nucleic acid analogues are attached to the activated interaction surface by in situ synthesis.

59. The method of claim 42 wherein nucleic acids or nucleic acid analogues are attached to the activated interaction surface by initial covalent attachment of linker molecules to the activated interaction surface followed by covalent attachment of the nucleic acids or nucleic acid analogues to the linker molecules.

60. The method of claim 59 wherein the linker molecules contain ethylene glycol subunits.

61. The method of claim 59 wherein the linker is hexaethylene glycol.

* * * * *

UNITED STATES PATENT AND TRADEMARK OFFICE
CERTIFICATE OF CORRECTION

PATENT NO.    : 6,503,711 B1
DATED         : January 7, 2003
INVENTOR(S)   : Krull et al.

It is certified that error appears in the above-identified patent and that said Letters Patent is hereby corrected as shown below:

Column 8,
Line 60, please replace "$10_8$" with -- $10^6$ --.

Column 10,
Line 14, please delete "of claim 2".
Line 54, please replace "3(b)" with -- 3(c) --.

Column 11,
Line 21, please replace "biosens" with -- biosensor --.

Column 13,
Line 21, please replace "consists" with -- consist --.

Column 19,
Line 67, please replace "compact an" with -- compact and --.

Column 21,
Line 54, please replace "yeilding" with -- yielding --.

Column 22,
Line 48, please replace "straight forward" with -- straightforward --.

Column 28,
Line 1, please replace "Gleaninq" with -- Cleaning --.

Column 32,
Line 37, please replace "sensor 30 ml" with -- sensor with 30 ml --.

Column 35,
Line 67, please insert a period after "efficiency".

UNITED STATES PATENT AND TRADEMARK OFFICE
CERTIFICATE OF CORRECTION

PATENT NO.    : 6,503,711 B1
DATED         : January 7, 2003
INVENTOR(S)   : Krull et al.

It is certified that error appears in the above-identified patent and that said Letters Patent is hereby corrected as shown below:

<u>Column 54,</u>
Line 1, please replace "(b)" with -- (c) --.
Line 5, please replace "(c)" with -- (d) --.
Line 7, please replace "(d)" with -- (e) --.
Line 12, please replace "(e)" with -- (f) --.
Line 15, please replace "(f)" with -- (g) --.
Line 17, please replace "(g)" with -- (h) --.
Line 48, please replace "42" with -- 44 --.

Signed and Sealed this

Eleventh Day of November, 2003

JAMES E. ROGAN
*Director of the United States Patent and Trademark Office*